(12) United States Patent
Vendely et al.

(10) Patent No.: US 10,390,828 B2
(45) Date of Patent: Aug. 27, 2019

(54) DEVICES AND METHODS FOR SEALING STAPLES IN TISSUE

(71) Applicant: Ethicon Endo-Surgery, Inc., Cincinnati, OH (US)

(72) Inventors: Michael J. Vendely, Lebanon, OH (US); Frederick E. Shelton, IV, Hillsboro, OH (US); Jason L. Harris, Lebanon, OH (US); Andrew Poskie, Chicago, IL (US)

(73) Assignee: Ethicon LLC, Guaynabo, PR (US)

( * ) Notice: Subject to any disclaimer, the term of this patent is extended or adjusted under 35 U.S.C. 154(b) by 111 days.

(21) Appl. No.: 14/300,807

(22) Filed: Jun. 10, 2014

(65) Prior Publication Data

US 2015/0351762 A1 Dec. 10, 2015

(51) Int. Cl.
*A61B 17/10* (2006.01)
*A61B 17/064* (2006.01)
(Continued)

(52) U.S. Cl.
CPC ...... *A61B 17/105* (2013.01); *A61B 17/00491* (2013.01); *A61B 17/068* (2013.01); *A61B 17/0644* (2013.01); *A61B 17/07207* (2013.01); *A61B 17/07292* (2013.01); *A61B 17/1155* (2013.01); *A61B 17/1114* (2013.01); *A61B 2017/00004* (2013.01); *A61B 2017/005* (2013.01); *A61B 2017/00495* (2013.01);
(Continued)

(58) Field of Classification Search
CPC ............... A61B 17/068; A61B 17/072; A61B 17/07292; A61B 17/0644; A61B 2017/07257; A61B 2017/07264; A61B 2017/07271; A61B 2017/00884
See application file for complete search history.

(56) References Cited

U.S. PATENT DOCUMENTS 4,548,202 A   10/1985   Duncan
4,617,928 A   10/1986   Alfranca
(Continued)

FOREIGN PATENT DOCUMENTS

CA   2834423 A1   11/2012
EP   1652481 A2    5/2006
(Continued)

OTHER PUBLICATIONS

Chen et al. "Elastomeric Biomaterials for Tissue Engineering." Prog. Polymer. Sci. 38(2013):584-671.
(Continued)

*Primary Examiner* — Shaun L David
(74) *Attorney, Agent, or Firm* — Mintz Levin Cohn Ferris Glovsky and Popeo, P.C.

(57) ABSTRACT

Devices and methods for sealing staples in tissue using adjuncts coupled to an individual staple are described herein. In one embodiment, a staple cartridge assembly is described that can include a cartridge body having a plurality of staple cavities, where each staple cavity has a surgical staple disposed therein. The assembly can also include a plurality of adjuncts, where each adjunct is disposed around at least one leg of a surgical staple such that each adjunct forms a seal around the at least one leg of the surgical staple upon deployment of the surgical staple from the cartridge body.

16 Claims, 80 Drawing Sheets

(51) Int. Cl.
*A61B 17/068* (2006.01)
*A61B 17/00* (2006.01)
*A61B 17/072* (2006.01)
*A61B 17/115* (2006.01)
*A61B 17/11* (2006.01)
*A61B 90/00* (2016.01)

(52) U.S. Cl.
CPC ........... *A61B 2017/00884* (2013.01); *A61B 2017/00893* (2013.01); *A61B 2017/00898* (2013.01); *A61B 2017/00942* (2013.01); *A61B 2017/07228* (2013.01); *A61B 2017/07257* (2013.01); *A61B 2017/07271* (2013.01); *A61B 2017/1132* (2013.01); *A61B 2090/037* (2016.02)

(56) References Cited

U.S. PATENT DOCUMENTS

| | | |
|---|---|---|
| 4,930,674 A | 6/1990 | Barak |
| 5,698,213 A | 12/1997 | Jamiolkowski et al. |
| 5,700,583 A | 12/1997 | Jamiolkowski et al. |
| 5,749,498 A | 5/1998 | Lavoie et al. |
| 5,882,133 A | 3/1999 | Chao et al. |
| 6,422,777 B1 | 7/2002 | Landrau et al. |
| 6,679,642 B1 | 1/2004 | Dillingham et al. |
| 7,143,924 B2 | 12/2006 | Scirica et al. |
| 7,143,925 B2 | 12/2006 | Shelton, IV et al. |
| 7,772,352 B2 | 8/2010 | Bezwada |
| 8,317,070 B2 | 11/2012 | Hueil et al. |
| 8,371,491 B2 | 2/2013 | Huitema et al. |
| 8,371,492 B2 | 2/2013 | Aranyi et al. |
| 8,388,633 B2 | 3/2013 | Rousseau et al. |
| 8,393,514 B2 | 3/2013 | Shelton, IV et al. |
| 8,540,131 B2 | 9/2013 | Swayze |
| 8,551,058 B2 | 10/2013 | Measamer et al. |
| 8,820,606 B2 | 9/2014 | Hodgkinson |
| 8,911,426 B2 | 12/2014 | Coppeta et al. |
| 9,615,826 B2 | 4/2017 | Shelton, IV et al. |
| 2005/0084514 A1 | 4/2005 | Shebuski et al. |
| 2006/0085032 A1 | 4/2006 | Viola |
| 2006/0108393 A1 | 5/2006 | Heinrich et al. |
| 2006/0257458 A1 | 11/2006 | Gorman et al. |
| 2007/0203510 A1 | 8/2007 | Bettuchi |
| 2008/0169333 A1 | 7/2008 | Shelton et al. |
| 2009/0001125 A1* | 1/2009 | Hess ............. A61B 17/105 227/176.1 |
| 2009/0234193 A1 | 9/2009 | Weisenburgh, II et al. |
| 2009/0270686 A1 | 10/2009 | Duke et al. |
| 2010/0087840 A1 | 4/2010 | Ebersole et al. |
| 2010/0147923 A1 | 6/2010 | D'Agostino et al. |
| 2010/0331880 A1 | 12/2010 | Stopek |
| 2011/0036888 A1 | 2/2011 | Pribanic et al. |
| 2011/0087279 A1 | 4/2011 | Shah et al. |
| 2011/0192882 A1 | 8/2011 | Hess et al. |
| 2012/0024934 A1 | 2/2012 | Shelton, IV et al. |
| 2012/0080335 A1 | 4/2012 | Shelton, IV et al. |
| 2012/0083835 A1 | 4/2012 | Shelton, IV et al. |
| 2012/0145767 A1 | 6/2012 | Shah et al. |
| 2012/0187179 A1* | 7/2012 | Gleiman ............. A61B 17/072 227/176.1 |
| 2012/0241493 A1* | 9/2012 | Baxter, III ....... A61B 17/07292 227/175.1 |
| 2012/0241498 A1 | 9/2012 | Gonzalez et al. |
| 2012/0241502 A1* | 9/2012 | Aldridge .......... A61B 17/07292 227/176.1 |
| 2013/0041406 A1* | 2/2013 | Bear ................. A61L 31/10 606/219 |
| 2013/0062391 A1 | 3/2013 | Boudreaux et al. |
| 2013/0068820 A1 | 3/2013 | Miller et al. |
| 2013/0075447 A1* | 3/2013 | Weisenburgh, II ........... A61B 17/00491 227/176.1 |
| 2013/0075450 A1 | 3/2013 | Schmid et al. |
| 2013/0112733 A1 | 5/2013 | Aranyi et al. |
| 2013/0146642 A1 | 6/2013 | Shelton, IV et al. |
| 2013/0153634 A1 | 6/2013 | Carter et al. |
| 2013/0153635 A1 | 6/2013 | Hodgkinson |
| 2013/0153641 A1 | 6/2013 | Shelton, IV et al. |
| 2013/0161374 A1 | 6/2013 | Swayze et al. |
| 2013/0256365 A1 | 10/2013 | Shelton, IV et al. |
| 2013/0256366 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256376 A1 | 10/2013 | Barton et al. |
| 2013/0256377 A1 | 10/2013 | Schmid et al. |
| 2014/0131418 A1 | 5/2014 | Kostrzewski |
| 2014/0131419 A1 | 5/2014 | Bettuchi |
| 2014/0158741 A1 | 6/2014 | Woodard, Jr. et al. |
| 2014/0224686 A1 | 8/2014 | Aronhalt et al. |
| 2015/0134076 A1 | 5/2015 | Shelton, IV et al. |
| 2015/0134077 A1* | 5/2015 | Shelton, IV ......... A61B 17/068 623/23.72 |
| 2015/0173756 A1 | 6/2015 | Baxter, III et al. |
| 2015/0238185 A1 | 8/2015 | Schellin et al. |
| 2015/0238188 A1 | 8/2015 | Vendely et al. |
| 2015/0239180 A1 | 8/2015 | Schellin et al. |
| 2015/0245835 A1 | 9/2015 | Racenet et al. |
| 2015/0272575 A1 | 10/2015 | Leimbach et al. |
| 2016/0128694 A1 | 5/2016 | Baxter, III et al. |
| 2017/0119390 A1 | 5/2017 | Schellin et al. |

FOREIGN PATENT DOCUMENTS

| | | |
|---|---|---|
| EP | 2397079 A1 | 12/2011 |
| EP | 2486860 A2 | 8/2012 |
| JP | 2009-201998 A | 9/2009 |
| JP | 20130075447 A | 4/2013 |
| WO | WO-9920328 A2 | 4/1999 |
| WO | WO-03088845 A2 | 10/2003 |
| WO | WO-03090630 A2 | 11/2003 |
| WO | WO-03094747 A1 | 11/2003 |
| WO | WO-2005048809 A1 | 6/2005 |
| WO | WO-2008039250 A1 | 4/2008 |
| WO | 14016819 A1 | 1/2014 |

OTHER PUBLICATIONS

Lim et al. "Fabrication and Evaluation of Poly(epsilon-caprolactone)/Silk Fibroin Blend Nanofibrous Scaffold." Biopolymers. 97(2012):265-275.
U.S. Appl. No. 13/763,192, filed Feb. 8, 2013.
U.S. Appl. No. 14/074,810, filed Nov. 8, 2013.
U.S. Appl. No. 14/074,884, filed Nov. 8, 2013.
U.S. Appl. No. 14/074,902, filed Nov. 8, 2013.
U.S. Appl. No. 14/075,438, filed Nov. 8, 2013.
U.S. Appl. No. 14/075,459, filed Nov. 8, 2013.
U.S. Appl. No. 14/300,793, filed Jun. 10, 2014.
U.S. Appl. No. 14/300,799, filed Jun. 10, 2014.
U.S. Appl. No. 14/300,801, filed Jun. 10, 2014.
U.S. Appl. No. 14/300,804, filed Jun. 10, 2014.
U.S. Appl. No. 14/300,811, filed Jun. 10, 2014.
U.S. Appl. No. 14/300,815, filed Jun. 10, 2014.
U.S. Appl. No. 14/300,817, filed Jun. 10, 2014.
U.S. Appl. No. 14/300,819, filed Jun. 10, 2014.
U.S. Appl. No. 14/300,820, filed Jun. 10, 2014.
U.S. Appl. No. 14/300,954, filed Jun. 10, 2014.
Zhao et al. "Biodegradable Fibrous Scaffolds Composed of Gelatin Coated Poly(?-caprolactone) Prepared by Coaxial Elecrospinning." J. Biomed. Mater. Res. 83A(2007):372-382.
European Search Report for Application No. 15171462.3 dated Oct. 12, 2015.
International Search Report and Written Opinion for Application No. PCT/US2015/030681 dated Jul. 22, 2015.
International Search Report and Written Opinion for Application No. PCT/US2015/029402 dated Sep. 21, 2015.
International Search Report and Written Opinion for Application No. PCT/US2015/030682 dated Jan. 28, 2016.

(56) References Cited

OTHER PUBLICATIONS

International Search Report and Written Opinion for Application No. PCT/US2015/030929 dated Sep. 18, 2015.

* cited by examiner

FIG. 12
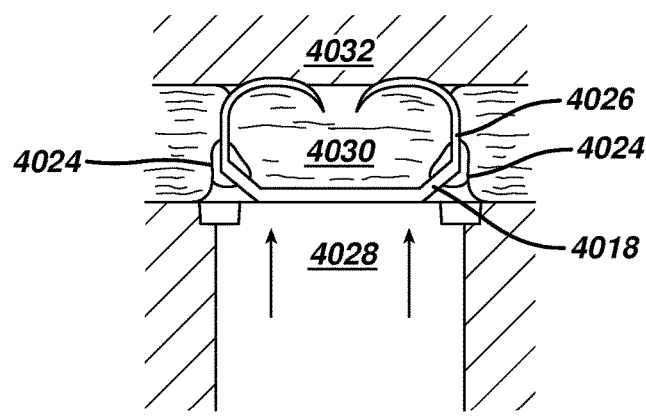
FIG. 13A    FIG. 13B
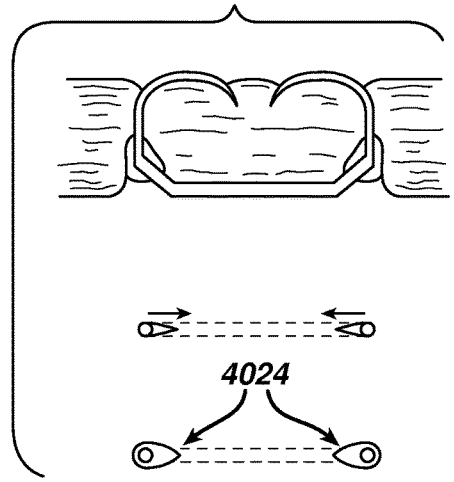 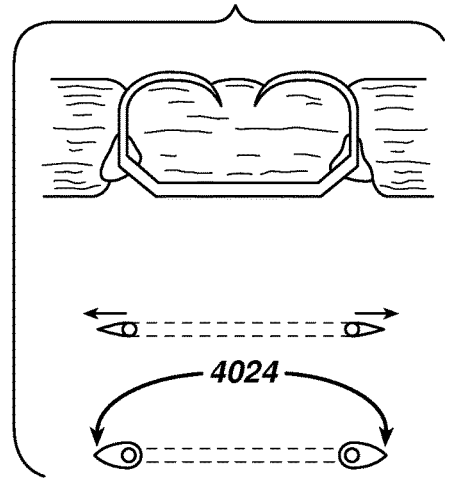

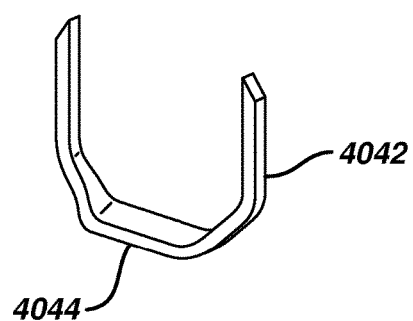
FIG. 16
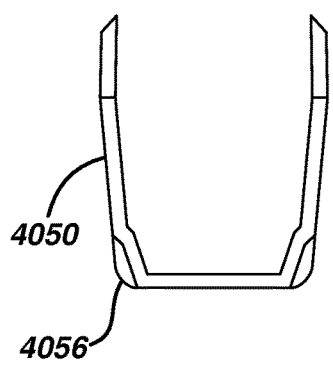 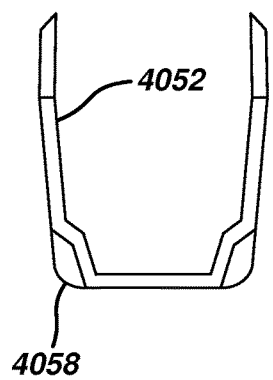 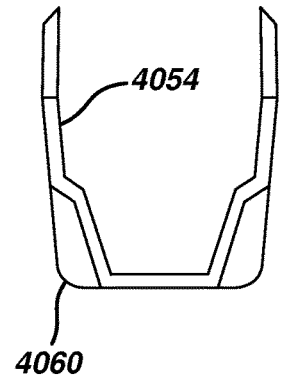
FIG. 17A  FIG. 17B  FIG. 17C

FIG. 20
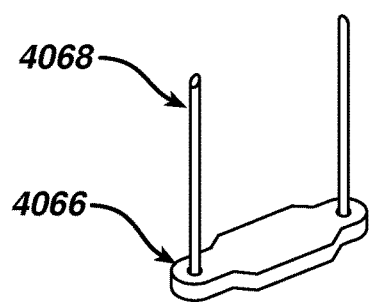
FIG. 21A          FIG. 21B
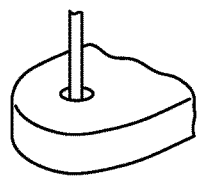   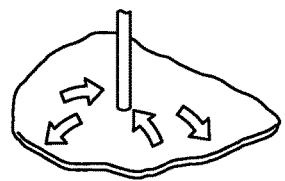

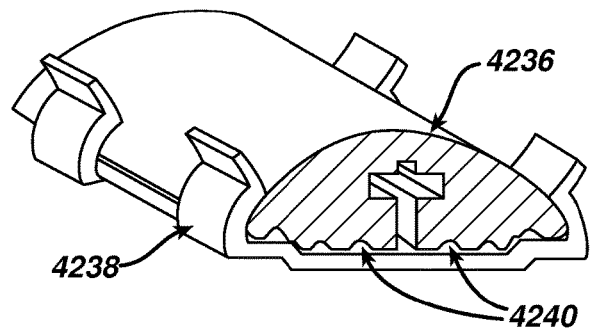
FIG. 51
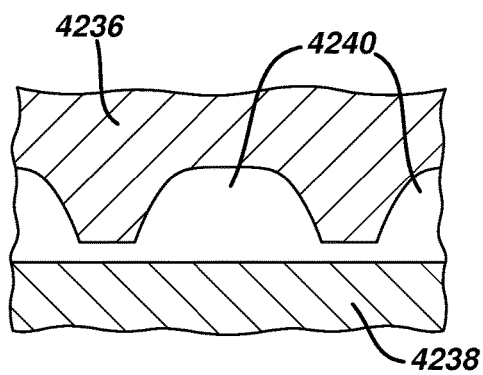 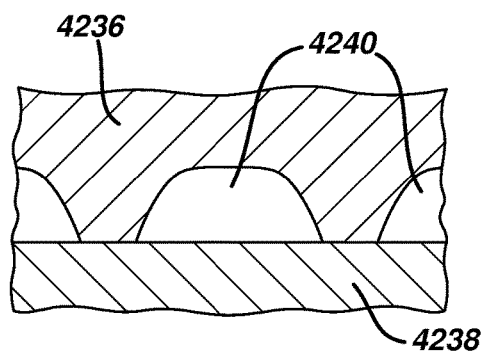
FIG. 52A     FIG. 52B

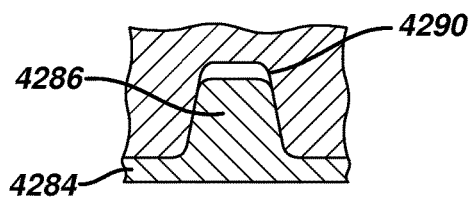
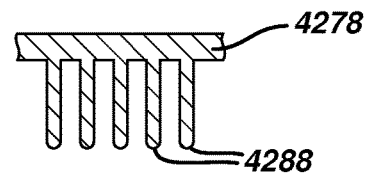
FIG. 61  FIG. 62
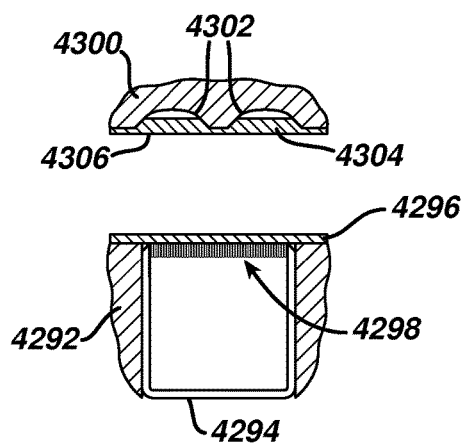
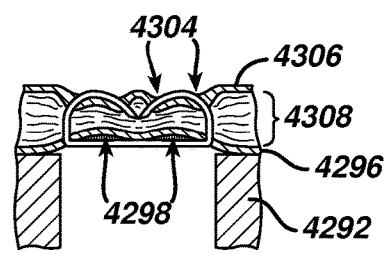
FIG. 63A  FIG. 63B

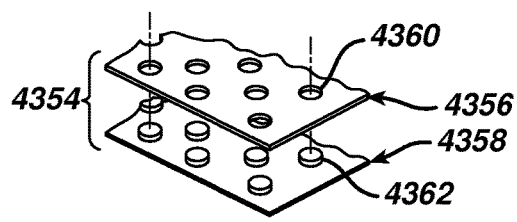 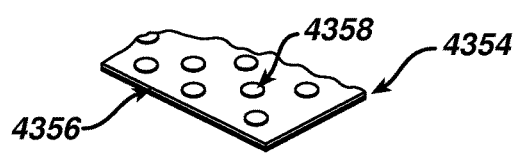
FIG. 68A  FIG. 68B
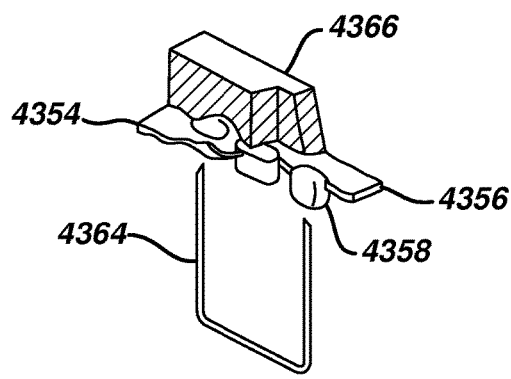 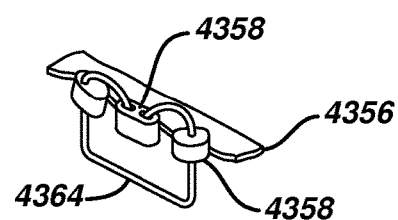
FIG. 69A  FIG. 69B

DEVICES AND METHODS FOR SEALING STAPLES IN TISSUE

FIELD

The subject matter disclosed herein relates to devices and methods for sealing staples deployed into tissue during surgical procedures.

BACKGROUND

Surgical staplers are used in surgical procedures to seal, divide, and/or transect tissues in the body by closing openings in tissue, blood vessels, ducts, shunts, or other objects or body parts involved in the particular procedure. The openings can be naturally occurring, such as passageways in blood vessels, airways or an internal lumen or organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate flexible or rigid shaft having a pair of opposed jaws formed on an end thereof for holding and forming staples therebetween. At least one of the opposed jaws is movable relative to the other jaw. In the case of laparoscopic surgery, often one jaw is fixed and the other is movable. In some devices (for example an open linear stapler), the opposed jaws can be separated by the operator and reassembled providing the relative motion needed for tissue placement. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut the stapled tissue between the stapled rows. Placement of the device, manipulation of components or systems of the device, and other actuations of the device such as articulation, firing, etc. can be accomplished in a variety of ways, such as electromechanically, mechanically, or hydraulically.

There are various types of staplers suited for particular surgical procedures. For example, linear staplers include a handle with an elongate shaft having a pair of opposed jaws formed on an end thereof for holding and forming staples therebetween. At least one of the opposed jaws is movable relative to the other. The staples are typically contained in a staple cartridge assembly, which can house multiple rows of staples and is often disposed in one of the two jaws for ejection of the staples to the surgical site. Circular staplers have a handle and an elongate shaft with an anvil and a cartridge assembly disposed on a distal end of the elongate shaft, the anvil axially movable relative to the cartridge assembly and configured to form staples therebetween and deploy the staples into tissue.

While surgical staplers have improved over the years, a number of problems can potentially arise. Although rare, as illustrated in FIG. 1, one problem is that leaks can occur due to staples S forming tears H when penetrating a tissue T or other object in which the staples S are disposed. Blood, air, gastrointestinal fluids, and other fluids can seep through the tears H formed by the staples S, even after the staples S are fully formed. The tissue T being treated can also become inflamed due to the manipulations and deformations that can occur during stapling. Still further, staples, as well as other objects and materials implanted during stapling procedures, generally lack the same characteristics as tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

In the particular case of stapling bronchial tubes, such as during lung resection, it is important for no leaks to be present after stapling so that air does not inappropriately enter or exit the lung and/or the thoracic cavity. Air escaping a stapled bronchial tube through a leak can interfere with breathing and lung function, such as by preventing full intake of air. Air exiting a stapled bronchial tube into the thoracic cavity through a leak is unsterile and can cause infection and/or other complications in the otherwise sterile environment of the thoracic cavity. However, it can be difficult to prevent leaks in bronchial tubes for a variety of reasons. The small size of bronchial tubes can make delivery of any sealing materials into bronchial tubes difficult, inflammation due to implanted staples and/or other objects and materials can cause bronchial tubes to close or nearly close since they have small diameters, and/or it can be difficult for sealing materials introduced into a bronchial tube to withstand the repeated expansion and contraction of the lung without failing and/or moving within the tube so as to break the seal of the bronchial tube.

In the particular case of stapling a colon, it is important that the staple line of the anastomosis is substantially sealed so that gastrointestinal solids and fluid remain in the organ. Leakage from the tubular body organ, e.g. a colon, can interfere with normal digestive function and can introduce bacteria into other portions of the body, causing infection. However, it can be difficult to prevent leaks in a tubular body organ for a variety of reasons. For example, it can be difficult for the tissue disposed near the staple line to withstand repeated expansion and contraction that occurs when solids and fluid passes through the colon. Additionally, it can be difficult to deliver sealant to the tubular body organ and control the position of the sealant when it is curing from a liquid state to a solidified state Accordingly, a need exists for improved devices and methods for sealing staples in tissue.

SUMMARY

Embodiments described herein address these and other challenges by providing, for example, adjunct materials that seal punctures made by surgical staples in tissue. The adjunct materials described herein have a number of embodiments, including embodiments in which an adjunct is disposed about a single staple or leg thereof, or about a group of staples. Various embodiments disclosed herein include adjuncts that seal staples in tissue from the crown, or staple cartridge, side, or from the anvil or staple leg side (or both).

In one aspect, for example, a staple cartridge assembly for use with a surgical stapler is provided that can include a cartridge body having a plurality of staple cavities, where each staple cavity has a surgical staple disposed therein. The assembly can further include a plurality of adjuncts, where each adjunct can be disposed around at least one leg of a surgical staple such that each adjunct forms a seal around the at least one leg of the surgical staple upon deployment of the surgical staple from the cartridge body.

The assembly can have a number of different features and/or modifications, all of which are considered within the scope of the invention. For example, the adjuncts can have a number of different shapes and sizes. In some embodiments, for example, each of the plurality of adjuncts can be in the form of a plug. In certain embodiments, for each surgical staple of the assembly, a first adjunct plug can be disposed around a first leg of the surgical staple and a second adjunct plug can be disposed around a second leg of the surgical staple such that the first and second adjunct plugs form a seal around the first and second legs of the surgical staple.

In other embodiments, each of the plurality of adjuncts can be in the form of a pledget configured to seal around both a first leg and a second leg of a surgical staple. The pledget itself can have a number of different shapes and sizes. For example, in some embodiments the pledget can be in the form of a rectangular box extending along a length of a crown of a staple. Any of a variety of other shapes are also possible.

In still other embodiments, each of the plurality of adjuncts can be in the form of a coating disposed around a leg of a surgical staple. The adjuncts can be disposed about solely the legs of a staple (or a portion thereof), or about the entirety of a staple.

In addition to shape and/or size, the plurality of adjuncts can also be formed from a variety of materials. For example, in some embodiments each of the plurality of adjuncts can be formed from a swellable material that expands upon contact with body fluids. Forming the adjuncts from such a material can enhance the adjuncts' ability to seal a puncture in tissue created by a staple leg. Any of a variety of biocompatible swellable materials can be employed. For example, in certain embodiments, the swellable material can be a hydrogel. In yet other embodiments, each of the plurality of adjuncts can be formed from other materials, such as a foam.

The plurality of adjuncts can be located at a variety of positions with respect to the plurality of staples, and can be configured in certain embodiments to move relative to a staple during implantation in tissue. For example, in certain embodiments each of the plurality of adjuncts can be positioned adjacent to a crown of a surgical staple prior to deployment from the cartridge body. In other embodiments, each of the plurality of adjuncts can be positioned at a distal end of the at least one leg of the surgical staple opposite a crown of the surgical staple prior to deployment from the cartridge body. In such an embodiment, for example, each of the plurality of adjuncts can be configured to slide over the at least one leg of the surgical staple. By way of further example, if an adjunct is positioned at a distal end of a staple leg, the action of forcing the staple leg through tissue can slide the adjunct toward a crown of the staple such that the adjunct is sandwiched between the tissue and the crown of the staple, thereby sealing the puncture created by the staple leg. In other embodiments, adjuncts can be positioned at other locations, such as on an anvil of a surgical stapler opposite the cartridge body, as described in more detail below.

In another aspect, a staple cartridge assembly for use with a surgical stapler is provided that can include a cartridge body having a plurality of staple cavities and a plurality of surgical staples disposed within the plurality of staple cavities and configured to be ejected therefrom into tissue. The assembly can also include a plurality of sealing adjuncts disposed within the plurality of staple cavities and configured to be ejected therefrom along with the plurality of surgical staples without contacting the cartridge body. By avoiding contact between the cartridge body and the sealing adjuncts, the adjuncts can be prevented from interfering with sliding movement of the staples relative to the cartridge body.

The adjuncts can be prevented from contacting the cartridge body in a number of different ways. For example, in some embodiments each of the plurality of sealing adjuncts can be positioned such that a surgical staple shields the sealing adjunct from contact with the cartridge body during ejection. This can be accomplished, for example, by coupling one or more sealing adjuncts to a staple so that the staple leads the adjunct as it is ejected from the cartridge body, thereby shielding the adjunct from contact with the cartridge body.

Other configurations for coupling adjuncts to a staple are also possible. For example, in certain embodiments, each of the plurality of sealing adjuncts can be positioned adjacent to a junction between a leg of a surgical staple and a crown of the surgical staple.

In still other embodiments, each of the plurality of staple cavities can be shaped to accommodate passage of at least one sealing adjunct coupled to a surgical staple. For example, each of the plurality of staple cavities includes at least one cut-out formed on opposing ends of the staple cavity to accommodate the at least one sealing adjunct.

As mentioned above, the adjuncts can be formed from a variety of biocompatible materials and have any of a variety of shapes and/or sizes. In some embodiments, each of the plurality of sealing adjuncts can be configured to expand in volume upon contact with tissue.

In another aspect, a method for stapling tissue is provided that can include engaging tissue between a cartridge assembly and an anvil on a surgical stapler, and actuating the surgical stapler to eject at least one staple from the cartridge assembly into the tissue. Further, at least one leg of the at least one staple can extend through a sealing adjunct such that the adjunct forms a seal between the tissue and the leg.

In some embodiments, the sealing adjunct can be coupled to a distal end of the at least one leg of the at least one staple. In such an embodiment, actuating the surgical stapler can cause the adjunct to slide toward a crown of the at least one staple and seal a hole formed in the tissue by the at least one leg. In other embodiments, however, the sealing adjunct can be coupled to a crown of the at least one staple and actuating the surgical stapler can cause the adjunct to eject from the cartridge assembly with the crown such that the sealing adjunct is disposed between the crown of the at least one staple and the tissue.

As mentioned above, various embodiments described herein can include sealing adjuncts positioned away from the crown of a surgical staple, such as on the opposite side of stapled tissue near staple legs that are deformed by an anvil of a surgical stapler. And, in some embodiments, adjuncts can be positioned at both locations to seal punctures from both sides of the tissue and/or staple.

In one aspect, a surgical device includes an end effector that can include first and second jaws, where the first jaw has a cartridge body removably attached thereto and the second jaw having an anvil. The cartridge body can have a plurality of staple cavities configured to seat staples therein and the anvil can have a plurality of staple forming openings formed therein. Further, at least one of the first and second jaws can be movable relative to the other jaw. The end effector can also include a plurality of sealing adjunct segments coupled to one another and at least one of the first and second jaws such that a staple ejected from the cartridge body passes through one of the plurality of sealing adjunct segments and tissue disposed between the first and second jaws.

In some embodiments, each of the plurality of sealing adjunct segments can span a plurality of staple forming openings. In other embodiments, however, each of the plurality of sealing adjunct segments can cover a single staple forming opening.

The plurality of sealing adjunct segments can be coupled to one another in a variety of manners. For example, in some embodiments each of the plurality of sealing adjunct segments can be coupled to one another by a plurality of connecting branches. Further, at least one of the first and second jaws can includes a plurality of features formed thereon that are configured to sever the plurality of connecting branches when deploying staples into tissue disposed between the first and second jaws. Destroying the connecting branches between sealing adjuncts can allow for greater compliance of tissue between adjacent staples, thereby reducing forces that can otherwise act to enlarge a puncture surrounding a staple leg.

In other embodiments, the plurality of sealing adjunct segments can be coupled to one another by a plurality of threads, or by a woven mesh. In still other embodiments, the plurality of sealing adjunct segments can be coupled to one another by a connective film extending over a surface of at least one of the first and second jaws. The connective film can, in some embodiments, have a first thickness and each of the plurality of sealing adjunct segments can have a second, greater thickness. In certain embodiments, the greater thickness of the sealing adjunct segments can extend into the plurality of staple forming openings. The plurality of sealing adjunct segments in such an embodiment does not significantly reduce the available clearance between the jaws of a surgical stapler, thereby allowing use with thicker tissue.

In addition to features that sever connections between sealing adjunct segments, at least one of the first and second jaws of the end effector can include one or more features formed thereon that are configured to at least one of align and secure the plurality of sealing adjunct segments thereto. Such features can be configured to mate with complementary features coupled to the plurality of sealing adjuncts such that the plurality of sealing adjuncts can be temporarily coupled to the end effector in a proper position and/or orientation. Examples of such features can include hooks and loops, plastic retainers, etc.

In certain embodiments, the plurality of sealing adjunct segments can have the same shape and can be arrayed in a repeating pattern over a length of the end effector. In other embodiments, the plurality of sealing adjunct segments can have a plurality of shapes and can be arrayed in an alternating pattern over a length of the end effector. Regardless, the plurality of sealing adjunct segments can cover each of the plurality of staple cavities such that each staple ejected into tissue passes through one of the plurality of sealing adjuncts.

In another aspect, an end effector for a surgical instrument is provided that includes first and second jaws, the first jaw having a cartridge body removably attached thereto and the second jaw having an anvil with a plurality of staple forming openings formed therein. The cartridge body can have a plurality of staple cavities configured to seat staples therein and at least one of the first and second jaws can be movable relative to the other jaw. The end effector can further include a viscous sealant disposed within the plurality of staple forming openings of the anvil, wherein the viscous sealant within each staple forming opening is retained therein by a film extending across the staple forming opening. In such an embodiment, the plurality of discrete pockets of viscous sealant can be the plurality of sealing adjunct segments described herein.

In some embodiments, the film extending across each staple forming opening can be formed from viscous sealant that is at least partially cured by exposure to any of a chemical, ultraviolet light, and heat. In other embodiments, however, the film extending across each staple forming opening can be formed from a second material overlaid on the viscous sealant.

In addition the film extending across each staple forming opening, in some embodiments each of the plurality of staple forming openings can include at least one retainer formed thereon to aid in retaining the viscous sealant within the opening. Further, while in some embodiments the film can extend solely across each staple forming opening of the anvil, in other embodiments the film can also extend between adjacent staple forming openings.

In another aspect, a surgical method is provided that can include filling a plurality of staple forming openings in an anvil of a surgical stapler with a viscous sealant, and forming a film over the plurality of staple forming openings in the anvil such that the film retains the viscous sealant within the staple forming openings.

As mentioned above, in certain embodiments forming the film can include at least partially curing the viscous sealant by exposure to any of a chemical, ultraviolet light, and heat. In other embodiments, however, forming the film can include overlaying a second material over the viscous sealant disposed within the staple forming openings.

In still other embodiments, the method can further include actuating the surgical stapler to drive a plurality of staples through tissue and into the plurality of staple forming openings such that the plurality of staples puncture the film and the viscous sealant forms a seal around the plurality of staples.

A surgical device is provided in the form of an applicator for coupling adjunct material to a surgical stapler. In one aspect, for example, a surgical device is provided that can include at least one nozzle formed at a proximal end of the device that is configured to receive a sealant, and an applicator formed at a distal end of the device that is configured to deliver the sealant received by the at least one nozzle. In one aspect, the applicator can be removably and replaceably attached to the nozzle. The applicator can be configured to interface with at least one of a first and second jaw of a surgical stapler such that the sealant delivered from the applicator can be deposited into a plurality of openings formed in the surgical stapler. The plurality of openings can be, for example, any of a plurality of staple cavities located in a cartridge body, or a plurality of staple forming openings formed in an anvil.

In some embodiments, it can be desirable to prevent adjunct material, such as the sealant, from being deposited in certain areas of a surgical stapler. For example, in some embodiments, it can be desirable to keep a cutting member guide path free from sealant. Accordingly, in some embodiments, the surgical device can include a shield disposed within the applicator such that the shield prevents the sealant delivered by the applicator from entering a cutting guide slot formed in at least one of the first and second jaw of the surgical stapler.

Still further, it can be desirable to remove any excess sealant from the surgical stapler prior to use. In some embodiments then, the surgical device can include a squeegee formed on a distal-most edge of the applicator to remove excess sealant.

There are a variety of biocompatible sealants that can be used with the devices and methods described herein. Certain of these sealants can be multi-part, such as two-part sealants that must be mixed before being coupled to the surgical stapler. Therefore, in some embodiments, the surgical device can include two nozzles formed at a proximal end thereof, and the applicator can include a common lumen extending therethrough to allow sealant received from each nozzle to mix before being delivered from a distal end of the applicator. In still other embodiments, the two nozzles can be configured to introduce sealant into the common lumen at different rates, e.g., for multi-part sealants that require components at various mixing ratios.

In some embodiments, the surgical device can further include a container of sealant coupled to the at least one nozzle. The container can be sealed for sterility purposes in certain embodiments, and the at least one nozzle can include a piercing tip configured to puncture a seal formed on the container. The container can have any of a variety of shapes and/or sizes. In some embodiments, however, the container can be a syringe.

In another aspect, a method for applying sealant to a surgical device is provided that can include applying a viscous sealant to a jaw member of a surgical stapler, wherein the jaw member includes a plurality of openings formed therein that can receive the sealant. The method can further include removing excess viscous sealant from the jaw member such that only sealant deposited within the plurality of openings remains.

The viscous sealant can be applied to the jaw member in a variety of manners. For example, in some embodiments applying the viscous sealant to the jaw member can include sliding an applicator along a length of the jaw member as sealant is introduced through the applicator. Further, in certain embodiments removing excess viscous sealant can include sliding a squeegee along a length of the jaw member. In some embodiments, the applicator can include a squeegee formed on a distal-most edge thereof to allow both sealant application and removal of excess sealant with a single pass over the jaw member.

In order to help retain the viscous sealant within the plurality of openings of the jaw member (e.g., staple cavity openings in a cartridge body or staple forming openings in an anvil), the method can further include at least partially curing the viscous sealant after application to the jaw member. At least partially curing the viscous sealant can create a hardened layer extending across the opening that can retain the uncured sealant within the opening until, for example, ejection of a staple from the surgical stapler punctures the hardened layer of the sealant. Curing the viscous sealant can be accomplished in a variety of manners, including, for example, by exposing the sealant to any of a chemical, ultraviolet light, and heat.

In a further aspect, a method for stapling tissue is provided that can include applying a non-compressible sealant into a plurality of staple forming openings formed in an anvil of a surgical stapler, and compressing tissue between the anvil and a cartridge body of the surgical stapler. The method can further include actuating the surgical stapler to deliver a plurality of staples from the cartridge body through the tissue and into the plurality of staple forming openings containing the non-compressible sealant. The non-compressible sealant can prevent tissue compressed between the anvil and the cartridge body from entering the plurality of staple forming openings upon actuation of the surgical stapler. This can be beneficial to prevent staples from being formed within tissue (i.e., without being passed completely through tissue).

As in the embodiments described above, applying the non-compressible sealant can, in certain embodiments, include sliding an applicator along a length of the anvil. In other embodiments, applying the non-compressible sealant can include mixing a multi-part sealant just prior to delivery into the plurality of staple forming openings. The multi-part sealant can be mixed at any of a variety of ratios, depending on the type of sealant used.

In other embodiments, the method can further include removing excess sealant from the anvil. This can be accomplished using a separate squeegee or other scraping implement, or it can be accomplished in a single pass if an applicator used to deposit the non-compressible sealant includes a squeegee or scraper thereon.

In still other embodiments, the method can further include at least partially curing the non-compressible sealant after application to the anvil. Such a curing process can harden at least a portion of the non-compressible sealant extending across the plurality of staple forming openings, thereby assisting in retaining the non-compressible sealant within the plurality of staple forming openings.

The devices and methods described herein can be utilized in a variety of different types of tissue throughout the body. Certain embodiments described herein can provide a more effective procedure for forming an anastomosis between two body lumens. Such a procedure is often employed when, for example, resecting a portion of a patient's colon.

A staple cartridge assembly for use with a surgical stapler is provided that can include a cartridge body having a plurality of staple cavities, where each staple cavity has a surgical staple disposed therein. The assembly can also include a plurality of sealing adjuncts coupled to the cartridge body such that a staple ejected from the cartridge body passes through one of the plurality of sealing adjuncts before entering into tissue adjacent to the cartridge body. Further, the plurality of staple cavities can be arranged such that a greater density of staple cavities is present at a proximal end and a distal end of the cartridge body than a density of staple cavities that is present in a middle portion extending between the proximal and distal ends. Further still, the plurality of sealing adjuncts can be positioned at the proximal and distal ends of the cartridge body. Positioning the plurality of sealing adjuncts at a proximal and distal end of the cartridge body can keep the sealing adjuncts from interfering with operation of a circular stapler that can resect tissue extending along the middle portion to form an anastomosis.

In some embodiments, however, the assembly can further include at least one suture thread coupled to and extending between the plurality of sealing adjuncts positioned at the proximal and distal ends of the cartridge body. Furthermore, to prevent interference of the at least one suture thread with any staples ejected from the cartridge body, the at least one suture thread can be offset from any staple cavity positioned in the middle portion of the cartridge body.

In other embodiments, the assembly can also include a washer disposed between the plurality of sealing adjuncts at the proximal and distal ends of the cartridge body and coupled to the at least one suture thread extending therebetween. More particularly, in certain embodiments, a first suture thread can extend between at least one sealing adjunct at a proximal end of the cartridge body and the washer, and a second suture thread can extend between the washer and at least one sealing adjunct at a distal end of the cartridge body. The first and second suture threads can have identical or different lengths, depending on the particular embodiment employed.

The washer can be formed from a variety of materials and can have a number of different sizes. In some embodiments, for example, the washer can be configured to elastically compress when the cartridge body is compressed against tissue. In other embodiments, the washer can be rigid and the cartridge body can include a depression formed therein to accommodate the washer during actuation of the surgical stapler. In still other embodiments, a compressible washer can be utilized in combination with a cartridge body having a recess formed therein such that a required amount of elastic compression can be reduced.

Including a connecting suture thread and washer in the assembly can allow for complete resection of the staple line including the sealing adjuncts when forming an anastomosis, as described in more detail below.

In a further aspect, a surgical method is provided that can include transecting a body lumen using a linear surgical stapler that delivers a plurality of sealing adjuncts in combination with a plurality of surgical staples at a proximal end and a distal end of a staple line formed by the surgical stapler. Further, the plurality of sealing adjuncts positioned at the proximal and distal ends of the staple line can be coupled to one another by at least one suture thread. The method can further include positioning a circular surgical stapler to create an anastomosis with a second body lumen across the staple line. The method can also include drawing the proximal and distal ends of the staple line into a central lumen of the circular stapler using the at least one suture thread extending between the plurality of sealing adjuncts positioned at the proximal and distal ends of the staple line, and actuating the circular stapler to form the anastomosis and resect the staple line.

In certain embodiments, the linear surgical stapler can also deliver a washer positioned at a mid-point between the proximal and distal ends of the staple line, and the washer can be coupled to the at least one suture thread.

In some embodiments, positioning the circular stapler to create an anastomosis can include passing a stapler trocar across the staple line and through the washer. Still further, in certain embodiments drawing the proximal and distal ends of the staple line into the central lumen of the circular stapler can include retracting the stapler trocar and the washer into the central lumen of the circular stapler. This can allow the circular stapler to completely resect the staple line including the sealing adjuncts when forming the anastomosis, thereby reducing the possibility of future leakage through the staple line formed by the linear surgical stapler.

In still other embodiments, positioning the circular stapler to create an anastomosis can further include mating an anvil to the stapler trocar such that the anvil prevents the stapler trocar from retracting through the washer. In such an embodiment, mating the anvil to the stapler trocar can trap the washer therebetween, such that retraction of the trocar into the central lumen of the circular stapler will pull the washer into the central lumen as well.

In another aspect, a surgical method is provided that can include transecting a body lumen using a linear surgical stapler that delivers a plurality of sealing adjuncts in combination with a plurality of surgical staples at a proximal end and a distal end of a staple line formed by the surgical stapler. Further, the plurality of sealing adjuncts positioned at the proximal and distal ends of the staple line can be coupled to a washer positioned at a midpoint of the staple line by a plurality of suture threads. The method can further include extending a trocar out of a central lumen of a circular stapler cartridge disposed within the body lumen such that the trocar crosses the staple line and passes through the washer. The method can also include coupling the trocar to an anvil positioned in a second body lumen such that a portion of the anvil receives the trocar and the washer is trapped between the anvil and the trocar. The method can further include retracting the trocar into the central lumen of the circular stapler cartridge to draw the anvil toward the circular stapler body while simultaneously drawing the proximal and distal ends of the staple line into the central lumen.

In certain embodiments, the method can also include actuating the circular stapler cartridge to resect the staple line and form an anastomosis between the two body lumens. As described above, actuation can resect the entirety of the staple line formed by the linear surgical stapler because the proximal and distal ends of the staple line are drawn into the central lumen of the circular stapler by their attachment to the washer via the plurality of suture threads.

BRIEF DESCRIPTION OF THE DRAWINGS

The invention will be more fully understood from the following detailed description taken in conjunction with the accompanying drawings, in which:

FIG. 12 is a cross-sectional view of the staple of FIG. 10 implanted in tissue;

FIG. 13A is an illustration of one embodiment of adjunct operation in non-thoracic tissue;

FIG. 13B is an illustration of one embodiment of adjunct operation in thoracic tissue;

FIG. 16 is a perspective view of the staple of FIG. 15;

FIG. 17A is a side view of one embodiment of adjuncts coupled to a staple;

FIG. 17B is a side view of an alternative embodiment of adjuncts coupled to a staple;

FIG. 17C is a side view of still another alternative embodiment of adjuncts coupled to a staple;

FIG. 20 is a perspective view of an alternative embodiment of an adjunct coupled to a staple;

FIG. 21A is a close perspective view of the adjunct of FIG. 20 before implantation in tissue;

FIG. 21B is a close perspective view of the adjunct of FIG. 20 after implantation in tissue;

FIG. 51 is a perspective cross-sectional view of one embodiment of a retainer to hold adjunct material against a surgical stapler anvil;

FIG. 52A is a cross-sectional view of the retainer and anvil of FIG. 51;

FIG. 52B is a cross-sectional view of an alternative embodiment of a retainer and anvil;

FIG. 61 is a close cross-sectional view of a staple forming opening of the surgical stapler of FIG. 59;

FIG. 62 is a cross-sectional view of one embodiment of a plurality of adjunct segments connected to one another by a film;

FIG. 63A is a cross-sectional view of the surgical stapler of FIG. 59 prior to actuation;

FIG. 63B is a cross-sectional view of the surgical stapler of FIG. 59 after actuation that delivers a staple into tissue;

FIG. 68A is an exploded view of one embodiment of a multi-material adjunct;

FIG. 68B is a perspective view of the adjunct of FIG. 68A;

FIG. 69A is a perspective cross-sectional view of the adjunct of FIG. 68A prior to actuation of a surgical stapler;

FIG. 69B is a perspective cross-sectional view of the adjunct of FIG. 68A after actuation of a surgical stapler;

FIG. 88B is a side view of the surgical staples and adjuncts of FIG. 87 in a tensioned state;

FIG. 89 is a top view of one embodiment of surgical staples and adjuncts extending between adjacent staples;

FIG. 90A is a top view of an alternative embodiment of surgical staples and adjuncts connected to one another by a serpentine carrier;

FIG. 90B is a side view of the surgical staples, adjuncts, and serpentine carrier of FIG. 90A;

FIG. 91A is a side view of one embodiment of an adjunct;

FIG. 91B is a front view of the adjunct of FIG. 91A;

FIG. 91C is a top view of the adjunct of FIG. 91A;

FIG. 91D is a perspective view of the adjunct of FIG. 91A;

FIG. 92A is a side view of an alternative embodiment of an adjunct;

FIG. 92B is a front view of the adjunct of FIG. 92A;

FIG. 92C is a top view of the adjunct of FIG. 92A;

FIG. 92D is a perspective view of the adjunct of FIG. 92A;

Figure 93:
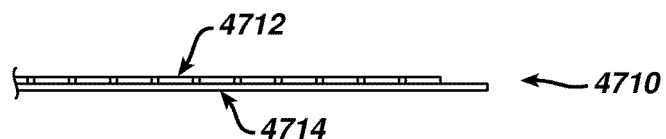
Figure 94A:
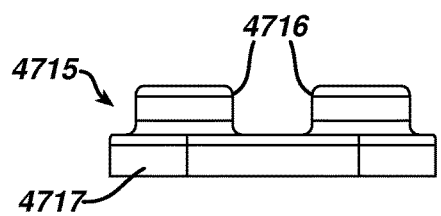
Figure 94B:
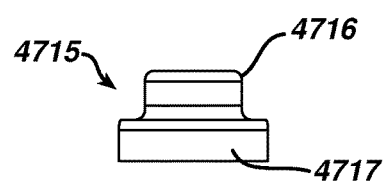
Figure 94C:
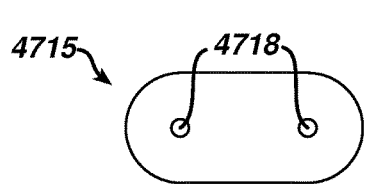
Figure 94D:
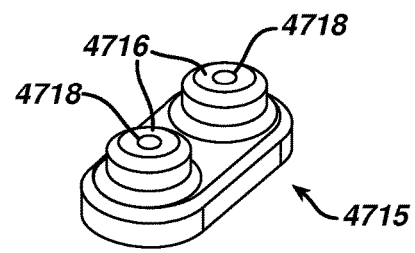
Figure 95A:
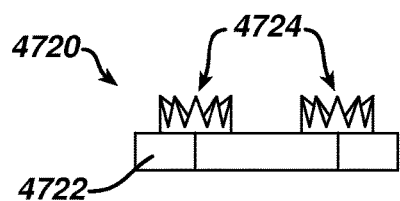
Figure 95B:
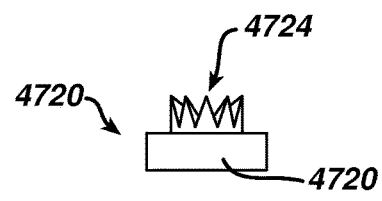
Figure 95C:
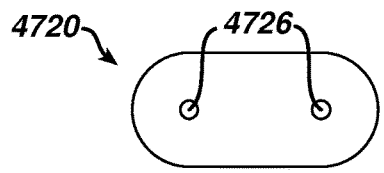
Figure 95D:
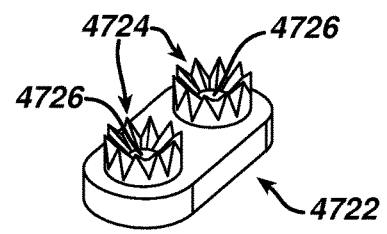
Figure 96:
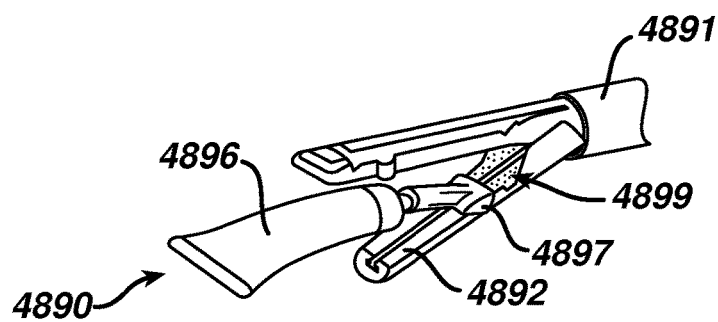
Figure 97:
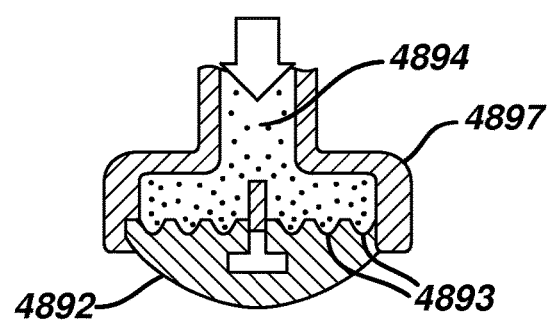
Figure 98:
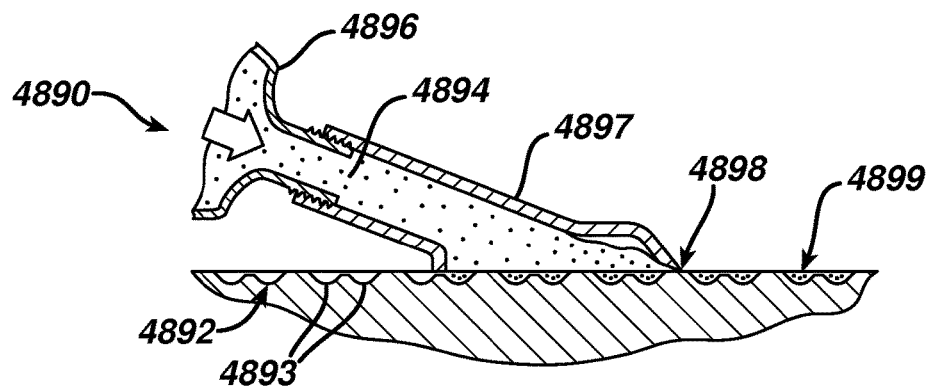
Figure 99A:
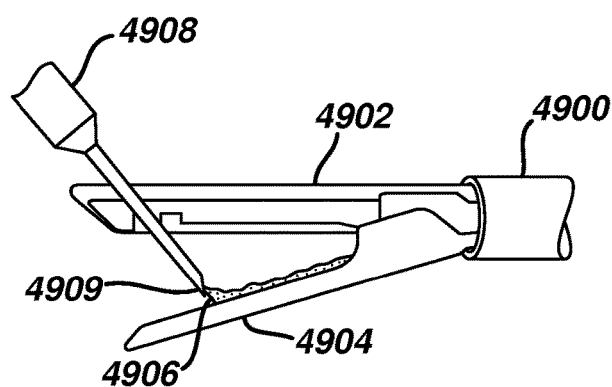
Figure 99B:
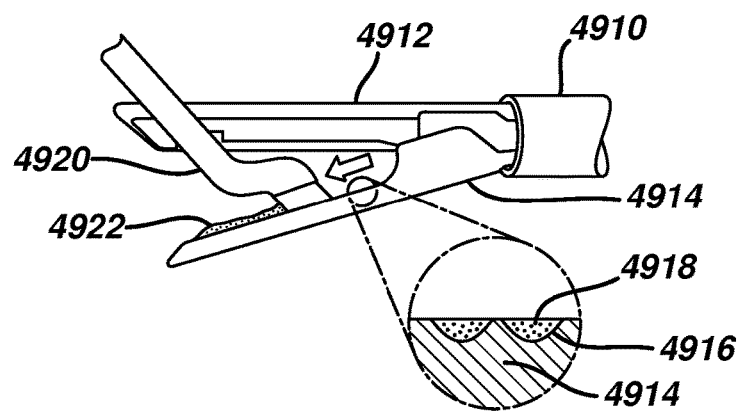
Figure 99C:
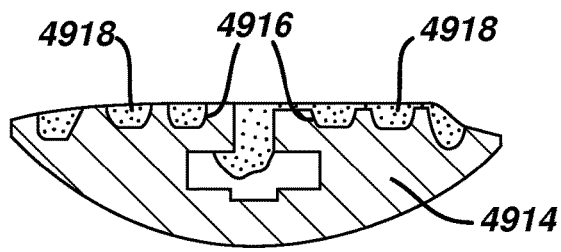
Figure 100:
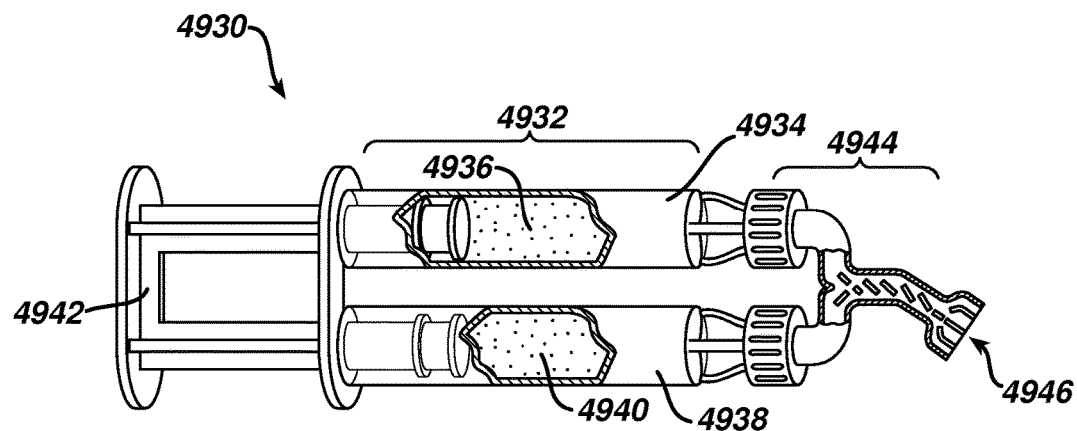
Figure 101:
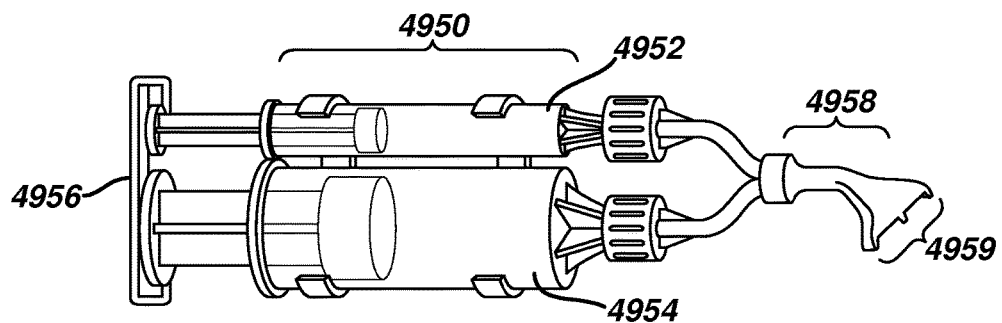
Figure 102A:
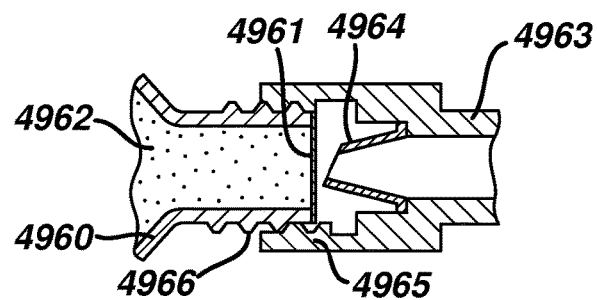
Figure 102B:
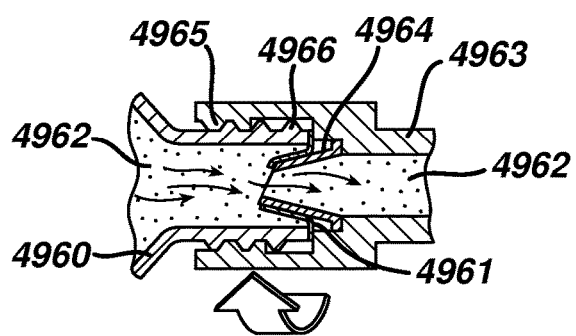
Figure 103:
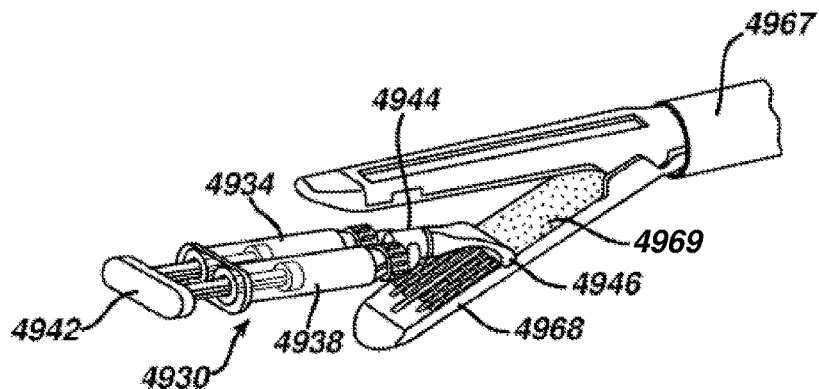
Figure 104:
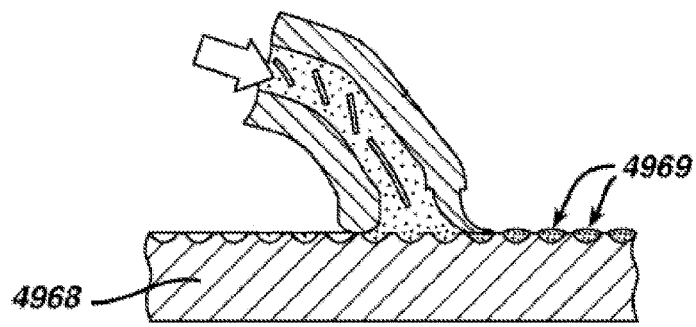
Figure 105:
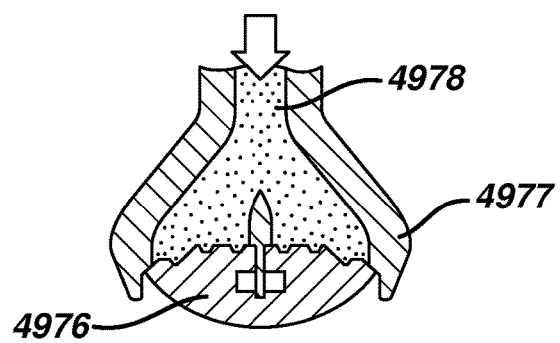
Figure 106:
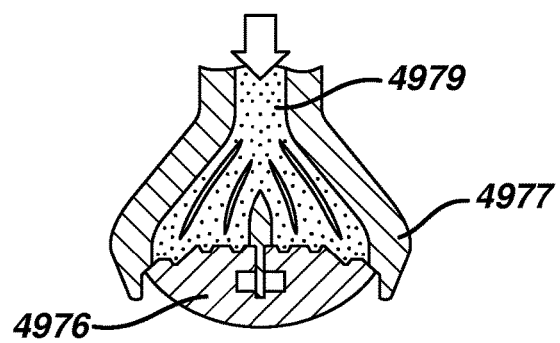
Figure 107:
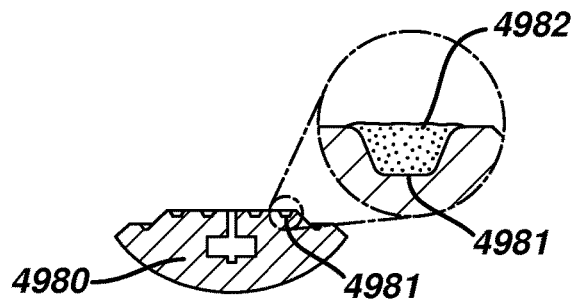
Figure 108:
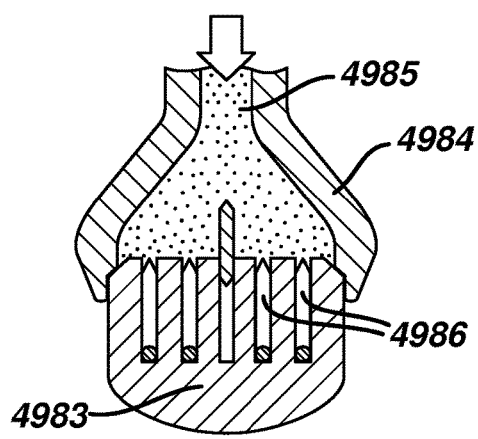
Figure 109:
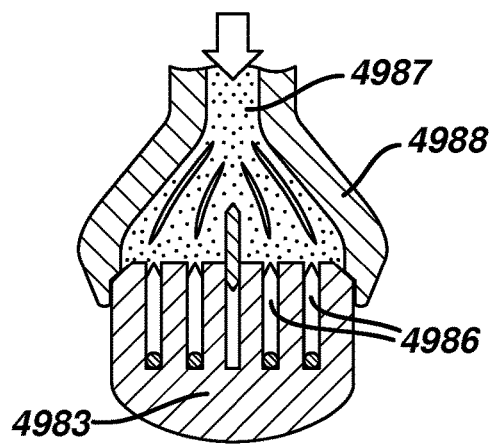
Figure 110:
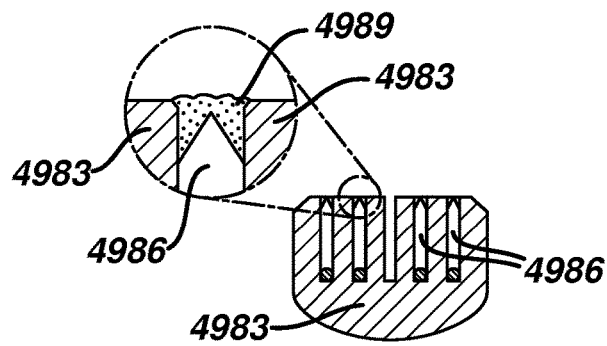
Figure 111:
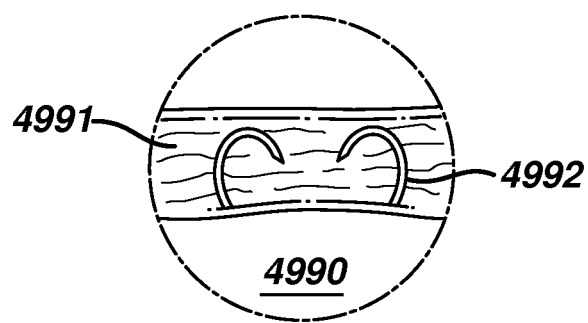
Figure 112:
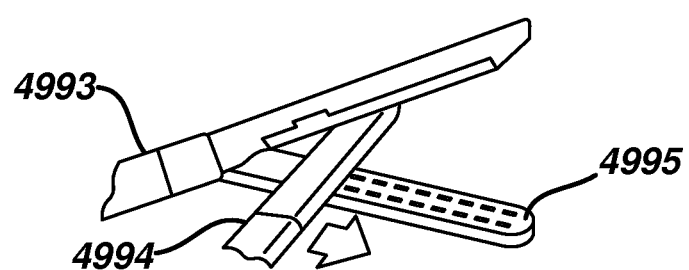
Figure 113:
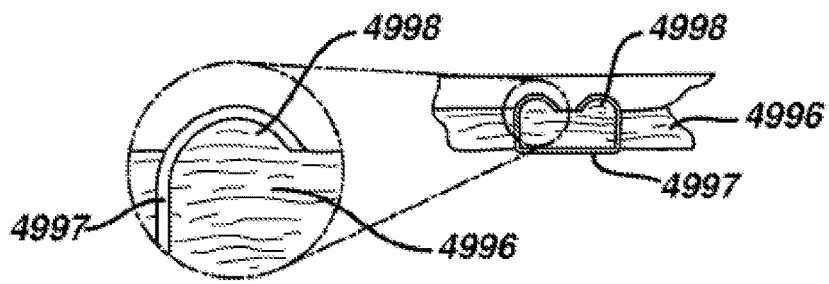
Figure 114A:
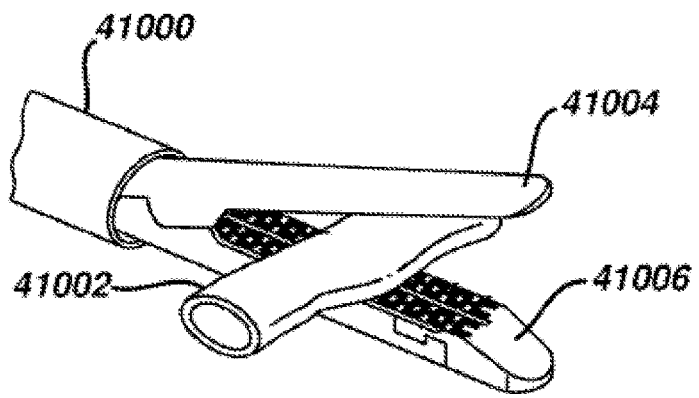
Figure 114B:
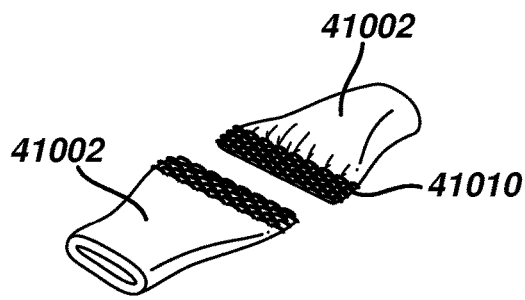
Figure 114C:
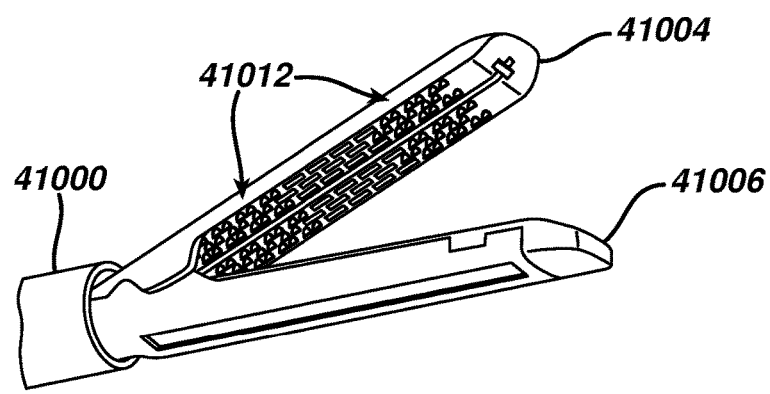
Figure 115:
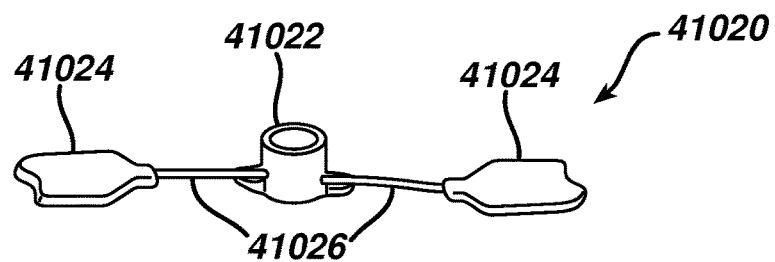
Figure 116:
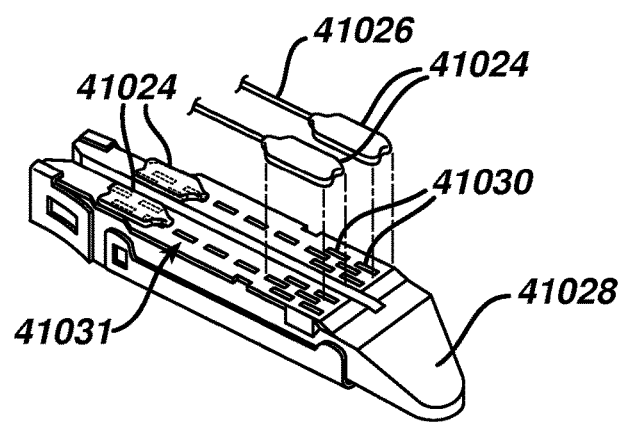
Figure 117:
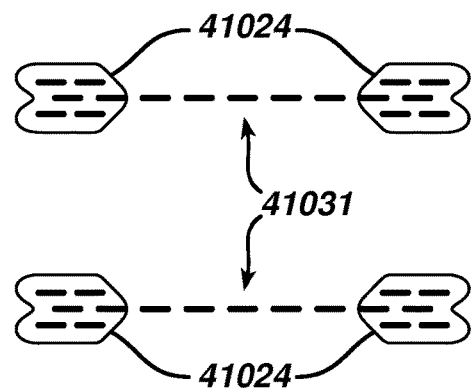
Figure 118:
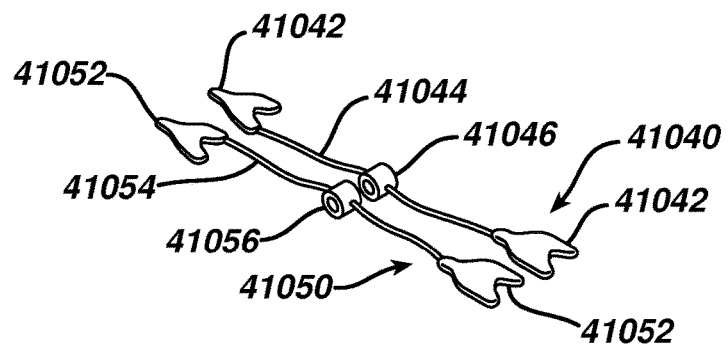
Figure 119:
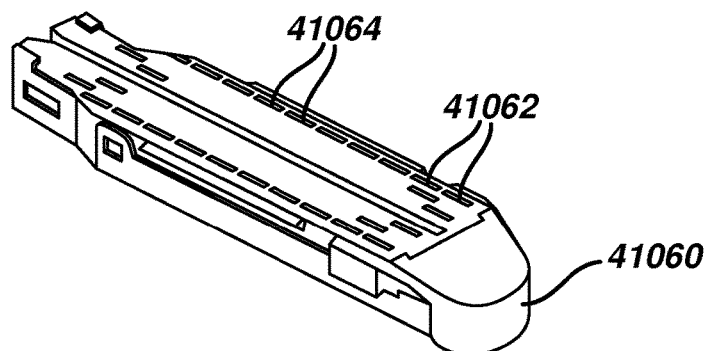
Figure 120:
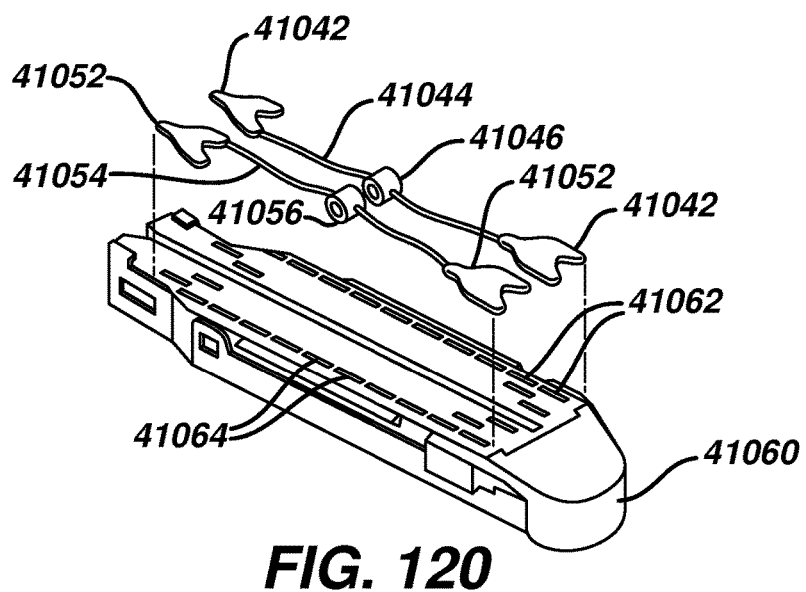
Figure 121:
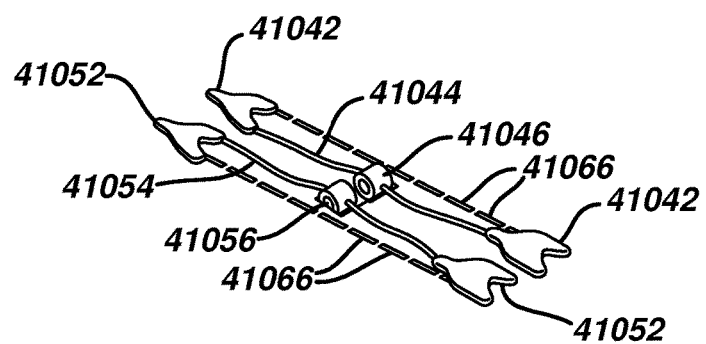
Figure 122:
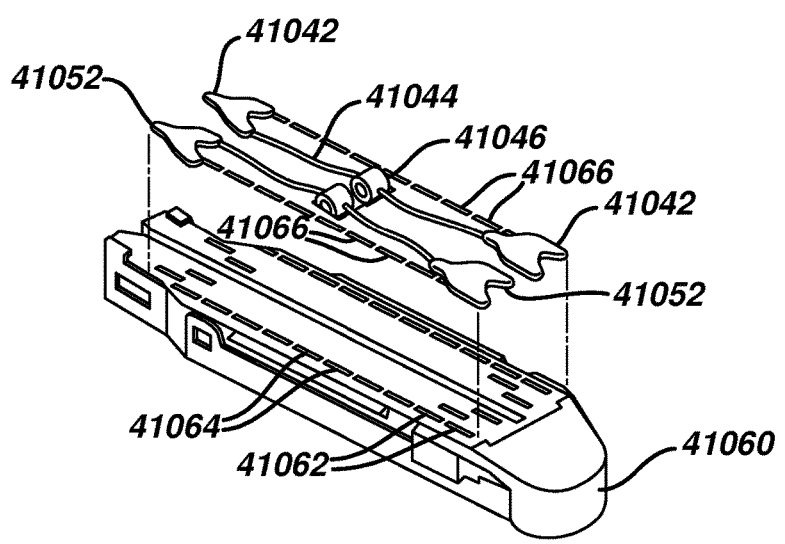
Figure 123:
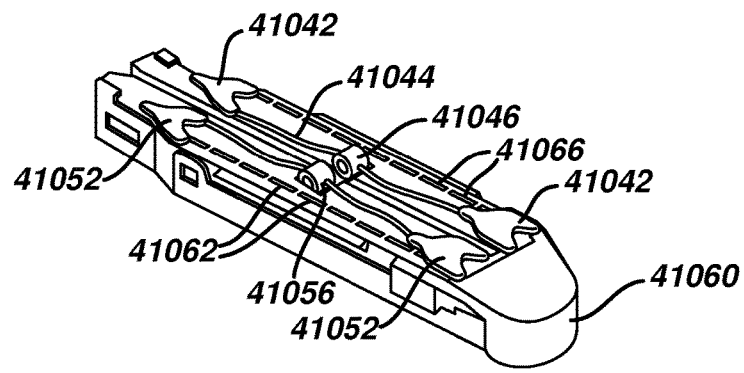
Figure 124:
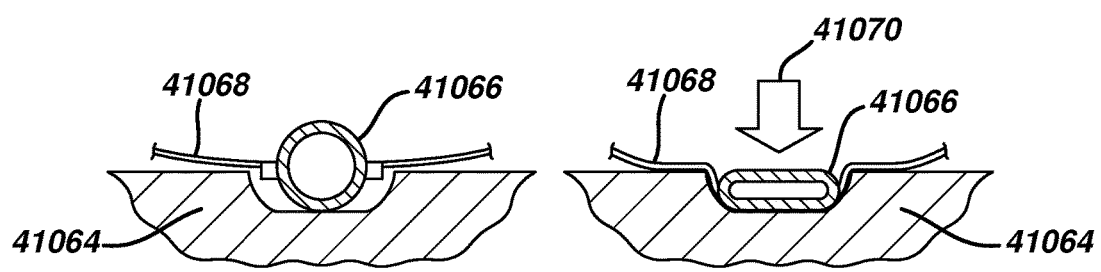
Figure 125:
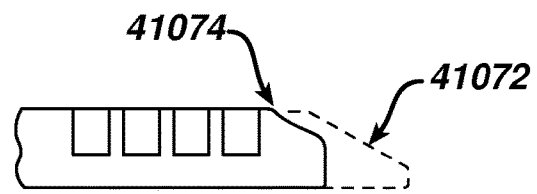
Figure 126:
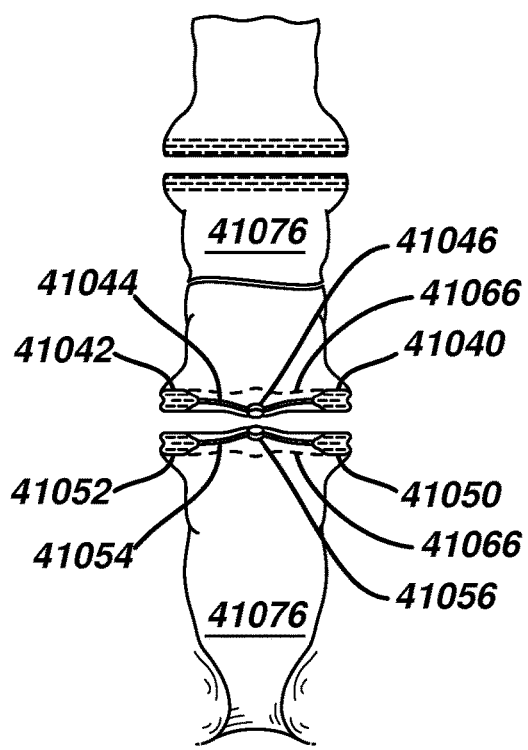
Figure 127A:
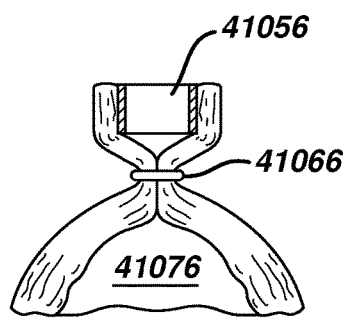
Figure 127B:
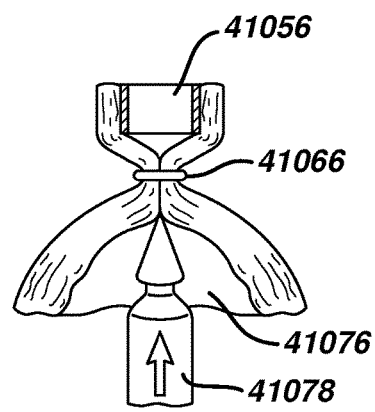
Figure 127C:
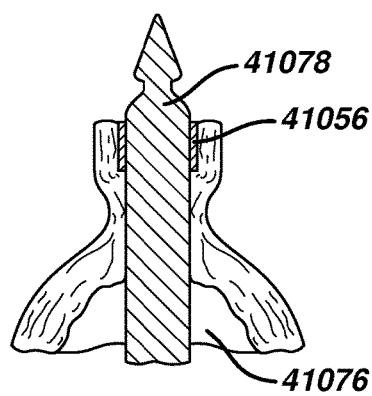
Figure 128:
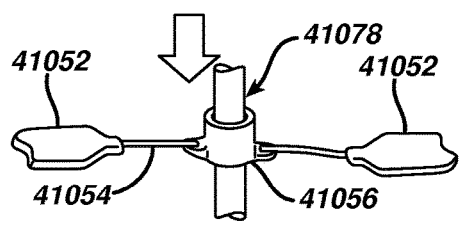
Figure 129:
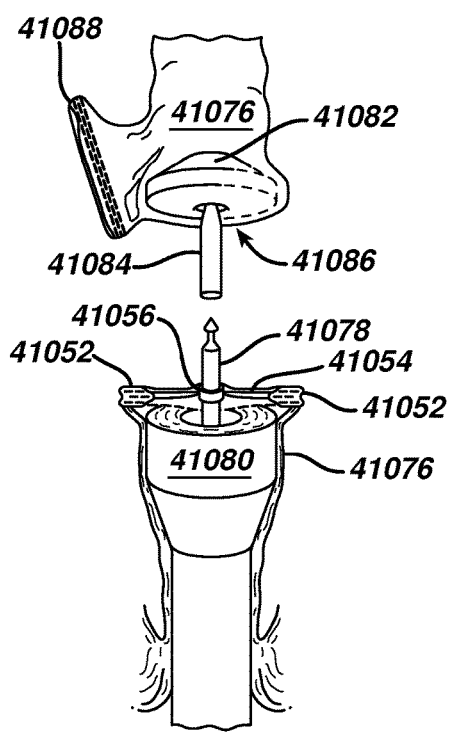
Figure 130:
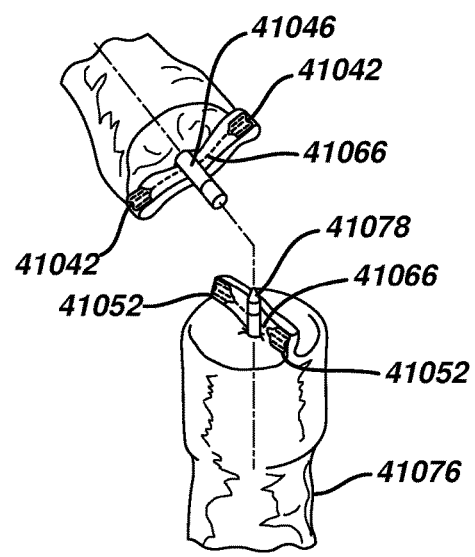
Figure 131:
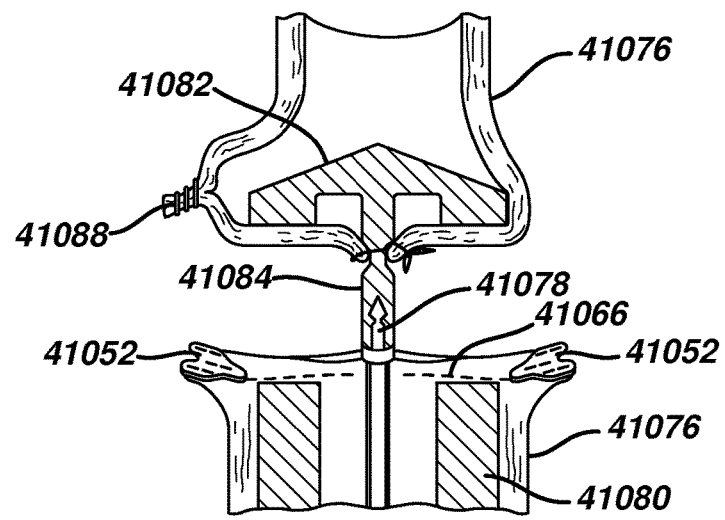
Figure 132:
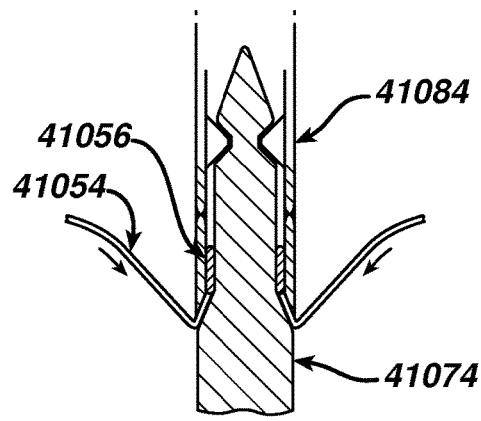
Figure 133:
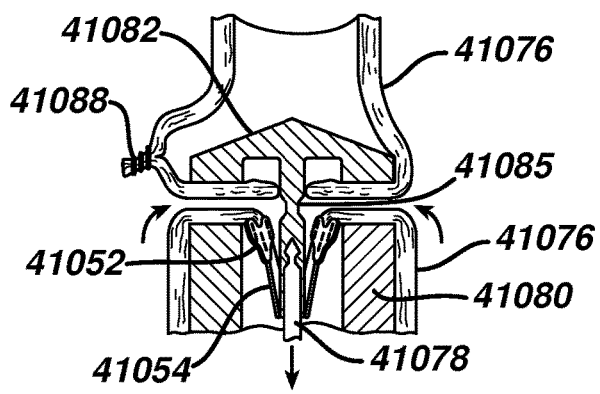
Figure 134:
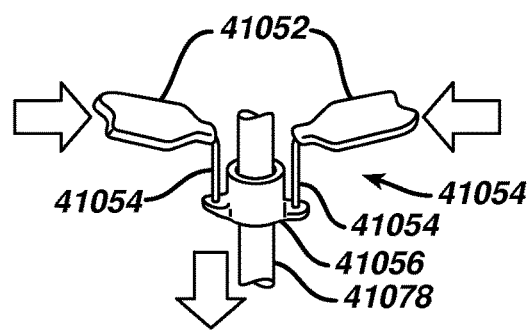
Figure 135:
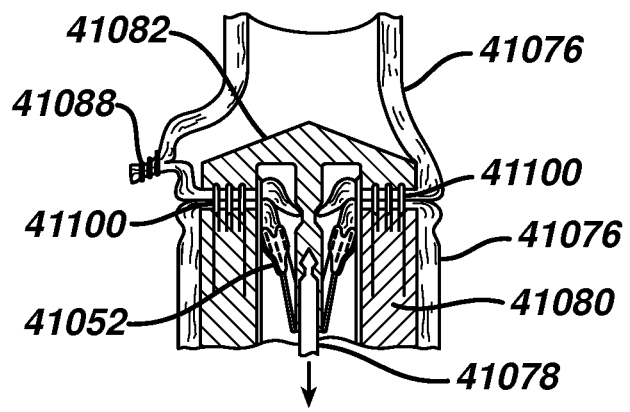
Figure 136:
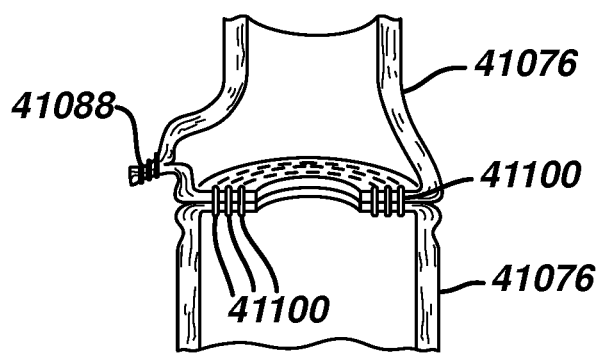

FIG. 93 is a side view of one embodiment of a plurality of adjuncts coupled to a backing material;

FIG. 94A is a side view of one embodiment of an adjunct;

FIG. 94B is a front view of the adjunct of FIG. 94A;

FIG. 94C is a top view of the adjunct of FIG. 94A;

FIG. 94D is a perspective view of the adjunct of FIG. 94A;

FIG. 95A is a side view of an alternative embodiment of an adjunct;

FIG. 95B is a front view of the adjunct of FIG. 95A;

FIG. 95C is a top view of the adjunct of FIG. 95A;

FIG. 95D is a perspective view of the adjunct of FIG. 95A;

FIG. 96 is an illustration of one embodiment of an adjunct applicator;

FIG. 97 is a cross-sectional view of the applicator of FIG. 96 applying an adjunct to a surgical stapler anvil;

FIG. 98 is a side view of the applicator of FIG. 96 applying an adjunct to a surgical stapler anvil;

FIG. 99A is an illustration of an alternative embodiment of an adjunct applicator;

FIG. 99B is an illustration of one embodiment of a squeegee that can remove excess adjunct applied to a surgical stapler;

FIG. 99C is a cross-sectional view of a surgical stapler anvil having an adjunct applied thereto;

FIG. 100 is an illustration of one embodiment of a two-part adjunct applicator;

FIG. 101 is an illustration of an alternative embodiment of a two-part adjunct applicator;

FIG. 102A is a cross-sectional view of one embodiment of an applicator nozzle coupled to an adjunct container;

FIG. 102B is a cross-sectional view of the applicator nozzle of FIG. 102A piercing a seal formed on the adjunct container;

FIG. 103 is an illustration of the applicator of FIG. 100 applying an adjunct to a surgical stapler;

FIG. 104 is a side cross-sectional view of one embodiment of an applicator applying an adjunct to a surgical stapler;

FIG. 105 is a front cross-sectional view of one embodiment of an applicator applying an adjunct to a surgical stapler anvil;

FIG. 106 is a front cross-sectional view of one embodiment of an applicator applying a two-part adjunct to a surgical stapler anvil;

FIG. 107 is a cross-sectional view of one embodiment of an adjunct disposed within a staple forming opening of a surgical stapler anvil;

FIG. 108 is a front cross-sectional view of one embodiment of an applicator applying an adjunct to a surgical stapler cartridge;

FIG. 109 is a front cross-sectional view of one embodiment of an applicator applying an adjunct to a surgical stapler cartridge;

FIG. 110 is a cross-sectional view of one embodiment of an adjunct disposed within a surgical stapler cartridge cavity;

FIG. 111 is a cross-sectional view of one embodiment of a surgical staple formed within tissue;

FIG. 112 is an illustration of one embodiment of an adjunct applicator and surgical stapler;

FIG. 113 is a cross-sectional view of one embodiment of a surgical staple formed so as to trap adjunct material;

FIG. 114A is an illustration of one embodiment of a surgical stapler positioned to transect tissue;

FIG. 114B is an illustration the tissue of FIG. 114A transected with staples and adjunct segments coupled thereto;

FIG. 114C is an illustration of the surgical stapler of FIG. 114A having excess staples and adjuncts coupled thereto;

FIG. 115 is an illustration of one embodiment of a non-continuous adjunct for use in forming an anastomosis;

FIG. 116 is an illustration of one embodiment of a surgical stapler cartridge for use with the adjunct of FIG. 115;

FIG. 117 is an illustration of one embodiment of a staple pattern for use with the adjunct of FIG. 115;

FIG. 118 is an illustration of an alternative embodiment of a non-continuous adjunct for use in forming an anastomosis;

FIG. 119 is an illustration of one embodiment of a surgical stapler cartridge for use with the adjunct of FIG. 118;

FIG. 120 is an exploded view of the adjunct of FIG. 118 and surgical stapler cartridge of FIG. 119;

FIG. 121 is an illustration of one embodiment of a staple pattern and the adjunct of FIG. 118;

FIG. 122 is an exploded view of the surgical stapler cartridge of FIG. 119 and the adjunct of FIG. 121;

FIG. 123 is an illustration of the surgical stapler cartridge of FIG. 119 and the adjunct of FIG. 121;

FIG. 124 is a cross-sectional view of one embodiment of an adjunct washer before and during actuation of a surgical stapler;

FIG. 125 is an illustration of one embodiment of a surgical stapler cartridge for use in forming an anastomosis;

FIG. 126 is an illustration of one embodiment of a body lumen transected by a surgical stapler;

FIG. 127A is a cross-sectional view of a staple line including an adjunct with a washer;

FIG. 127B is a cross-sectional view of a circular stapler trocar advancing toward the staple line of FIG. 127A;

FIG. 127C is a cross-sectional view of the circular stapler trocar of FIG. 127B crossing the staple line of FIG. 127A;

FIG. 128 is an illustration of a circular stapler trocar passing through a washer of the non-continuous adjunct of FIG. 115;

FIG. 129 is an illustration of a circular stapler anvil being positioned over the circular stapler trocar of FIG. 127B;

FIG. 130 is an illustration of an alternative embodiment of a circular stapler anvil being positioned over the circular stapler trocar of FIG. 127B;

FIG. 131 is a cross-sectional view of one embodiment of a circular stapler anvil trapping an adjunct washer over a circular stapler trocar;

FIG. 132 is a close cross-sectional view of the circular stapler anvil, adjunct washer, and circular stapler trocar of FIG. 131;

FIG. 133 is a cross-sectional view of the circular stapler trocar of FIG. 131 being withdrawn into a central lumen of the circular stapler;

FIG. 134 is an illustration of one embodiment of forces exerted on a non-continuous adjunct upon withdrawal of a circular stapler trocar coupled thereto;

FIG. 135 is a cross-sectional view of the circular stapler of FIG. 131 being actuated to resect the staple line including the non-continuous adjunct; and FIG. 136 is a cross-sectional view of an anastomosis produced by actuation of the circular stapler of FIG. 131.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of such devices and methods is defined solely by the claims. The features illustrated or described in connection with one exemplary embodiment may be combined with the features of other embodiments. Such modifications and variations are intended to be included within the scope of the devices and methods described herein. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments,"

"in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the methods, apparatus, devices, and systems described herein.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

It can be desirable to use one or more biologic materials and/or synthetic materials, collectively referred to herein as "adjunct materials," in conjunction with surgical instruments to help improve surgical procedures. These biologic materials may be derived from human and/or animal sources. A person skilled in the art may refer to these types of materials as buttress materials as well as adjunct materials.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

End effectors of the surgical instruments as described herein can be configured to deliver one or more synthetic materials and/or biologic materials, collectively referred to herein as "adjunct materials," to a surgical site to help improve surgical procedures. These biologic materials may be derived from human and/or animal sources. While a variety of different end effectors can benefit from the use of adjunct materials, in some exemplary embodiments the end effector can be a surgical stapler. When used in conjunction with a surgical stapler, the adjunct material(s) can be disposed between and/or on jaws of the stapler, incorporated into a staple cartridge disposed in the jaws, or otherwise placed in proximity to the staples. When staples are deployed, the adjunct material(s) can remain at the treatment site with the staples, in turn providing a number of benefits. In some instances, the adjunct material(s) can be used to help seal holes formed by staples as they are implanted into tissue, blood vessels, and various other objects or body parts, and/or can be used to provide tissue reinforcement at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct material(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct material(s) can be configured to wick or absorb beneficial fluids, e.g., sealants, blood, glues, that further promote healing, and in some instances, the adjunct material(s) can be configured to degrade to form a gel, e.g., a sealant, that further promotes healing. In some instances, the adjunct may carry materials that when placed into a wet environment (e.g., blood, water, saline, or other bodily fluids) form a sealant to create a seal (e.g., human or animal derived fibrinogen and thrombin can be lyophilized into a powder form that when mixed with water creates a sealant). Still further, the material(s) can help reduce inflammation, promote cell growth, and otherwise improve healing.

Figure 1:
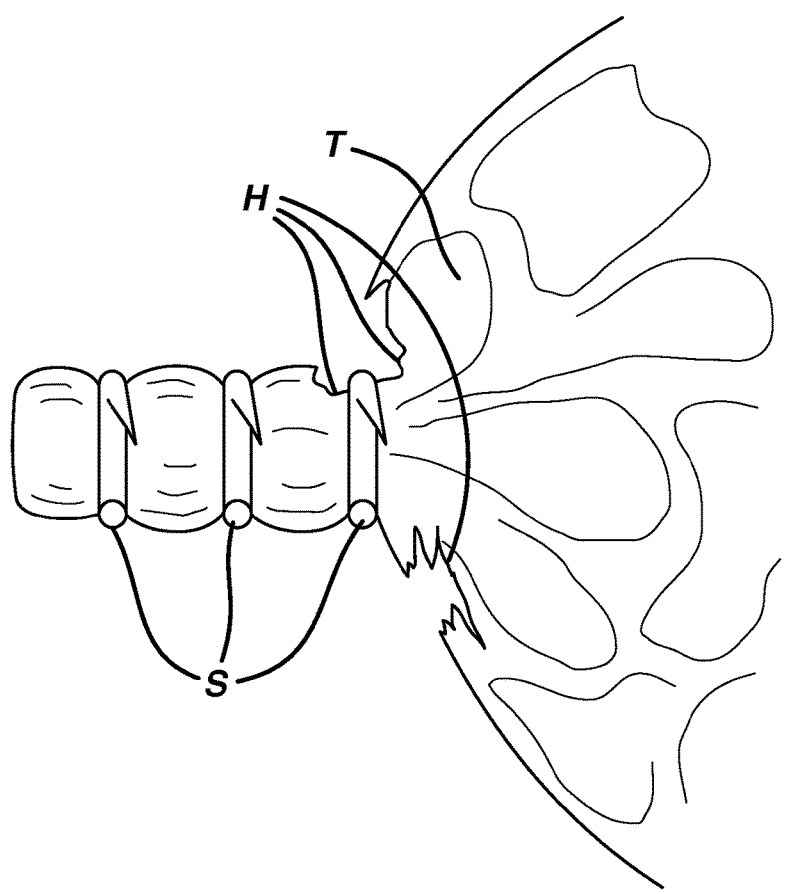
FIG. 1 is a side view of damaged stapled tissue.
Figure 2:
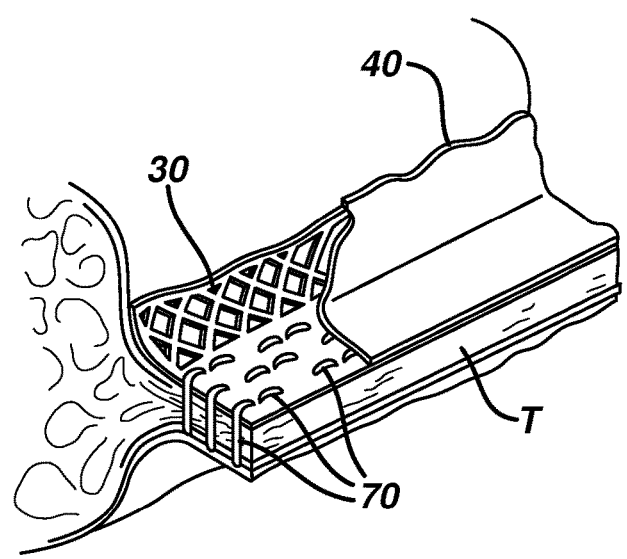
FIG. 2 is a perspective view of one embodiment of an adjunct material as described herein that is fixed to stapled tissue.

FIG. 2 illustrates one embodiment of an adjunct material that includes a porous buttress 30 that can be fixed to a tissue T to be treated by a surgical stapler and that remains at the treatment site with staples 70. The buttress 30 can be made from one or more absorbent materials and can be stamped, pressed, cut, molded, woven, melted, blown, comprised from composite structures and/or methods or otherwise shaped to facilitate absorption, reinforcement, delivery and/or retention of beneficial fluids such as sealants, glues, blood, etc. The absorption and/or retention of beneficial fluids, for example a fibrin sealant 40, at the treatment site can further help to prevent leaks and to reinforce the buttress 30.

In use, the adjunct material can come pre-loaded onto the device and/or the staple cartridge, while in other instances the adjunct material can be packaged separately. In instances in which the adjunct material comes pre-loaded onto the device and/or the staple cartridge, the stapling procedure can be carried out as known to those skilled in the art. For example, in some instances the firing of the device can be enough to disassociate the adjunct material from the device and/or the staple cartridge, thereby requiring no further action by the clinician. In other instances any remaining connection or retention member associating the adjunct material with the device and/or the staple cartridge can be removed prior to removing the instrument from the surgical site, thereby leaving the adjunct material at the surgical site. In instances in which the adjunct material is packaged separately, the material can be releasably coupled to at least one of a component of the end effector and the staple cartridge prior to firing the device. The adjunct material may be refrigerated, and thus removed from the refrigerator and the related packaging, and then coupled to the device using a connection or retention member as described herein or otherwise known to those skilled in the art. The stapling procedure can then be carried out as known to those skilled in the art, and if necessary, the adjunct material can be disassociated with the device as described above.

Adjunct materials described herein may be used in any surgery where a surgical stapler or other instrument creating tissue punctures is utilized. In some embodiments, adjunct materials described herein may be used for sealing staple punctures created when a surgical stapler is used in lung surgery. When surgery is performed on a lung (e.g., lobectomy, segmentectomy, wedge resection, lung volume reduction surgery, etc.), the lung is typically collapsed, and the required procedure, including application of the stapler to tissue to be removed, is then performed on the collapsed lung. After the procedure is completed, the collapsed lung is re-inflated. The re-inflation of the lung stretches the lung parenchyma, which may result in increased stress at a junction between the stapled tissue and surrounding tissue that was not punctured. Furthermore, airtight sealing is required for the staple punctures of the lung. Such airtight sealing may be difficult to achieve due to lung tissue movement. While leaks around staple punctures typically heal within approximately five days, in some cases, staple punctures may persist for longer periods of time, such as, for example, up to six months.

Accordingly, some embodiments provide adjunct material that may be used to seal staple punctures created by a surgical stapler used to secure lung tissue. However, it should be appreciated that the adjunct materials can also be used to seal punctures created by surgical staplers used to secure any other type of tissue, such as, for example, blood vessels, intestinal, stomach and esophageal tissue.

Surgical Stapling Instrument

Figure 3:
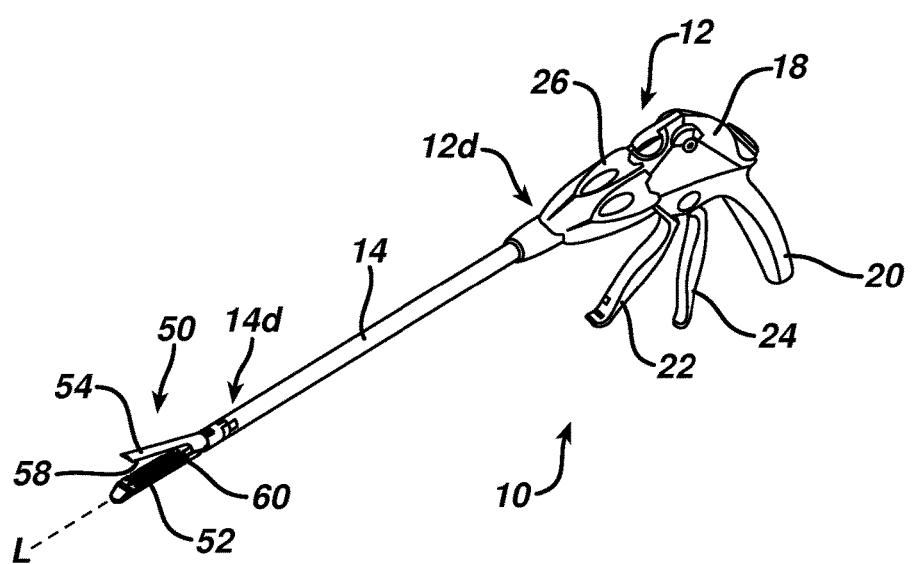
FIG. 3 is a perspective view of a prior art surgical instrument which can be used with one or more adjunct materials.

While a variety of surgical instruments can be used in conjunction with the adjunct materials disclosed herein, FIG. 3 illustrates one, non-limiting exemplary embodiment of a surgical stapler 10 suitable for use with one or more adjunct materials. The instrument 10 generally includes a handle assembly 12, a shaft 14 extending distally from a distal end 12d of the handle assembly 12, and an end effector 50 at a distal end 14d of the shaft 14. Because the illustrated embodiment is a surgical stapler, the end effector 50 has jaws 52, 54, although other types of end effectors can be used with the shaft 14, handle assembly 12, and components associated with the same. The surgical stapler 10 includes opposed lower and upper jaws 52, 54 with the lower jaw 52 including a staple channel 56 (FIG. 4) configured to support a staple cartridge 60, and the upper jaw 54 having an inner surface 58 that faces the lower jaw 52 and that is configured to operate as an anvil to help deploy staples 70 of the staple cartridge 60. The jaws 52, 54 are configured to move relative to one another to clamp tissue or other objects disposed therebetween, and components of a firing system can be configured to pass through at least a portion of the end effector 50 to eject the staples into the clamped tissue. In various embodiments a knife blade 81 can be associated with the firing system to cut tissue during the stapling procedure. At least one of the opposed lower and upper jaws 52, 54 will be moveable relative to the other lower and upper jaws 52, 54. At least one of the opposed lower and upper jaws 52, 54 may be fixed or otherwise immovable. In some embodiments, both of the opposed lower and upper jaws 52, 54 will be movable.

Operation of the end effector 50 can begin with input from a clinician at the handle assembly 12. The handle assembly 12 can have many different configurations designed to manipulate and operate the end effector 50 associated therewith. In the illustrated embodiment, the handle assembly 12 has a pistol-grip type housing 18 with a variety of mechanical and/or electrical components disposed therein to operate various features of the instrument. For example, the handle assembly 12 can include a rotation knob 26 mounted adjacent a distal end 12d thereof which can facilitate rotation of the shaft 14 and/or the end effector 50 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 52, 54 to collapse towards each other and to thereby clamp tissue therebetween. Movement of the firing trigger 24 can actuate the firing system, described below, which can cause the ejection of staples from a staple cartridge disposed therein and/or the advancement the knife blade 81 to sever tissue captured between the jaws 52, 54. A person skilled in the art will recognize that various configurations of components for a firing system, mechanical, hydraulic, pneumatic, electromechanical, robotic, or otherwise, can be used to eject staples and/or cut tissue, and thus a detailed explanation of the same is unnecessary.

Figure 4:
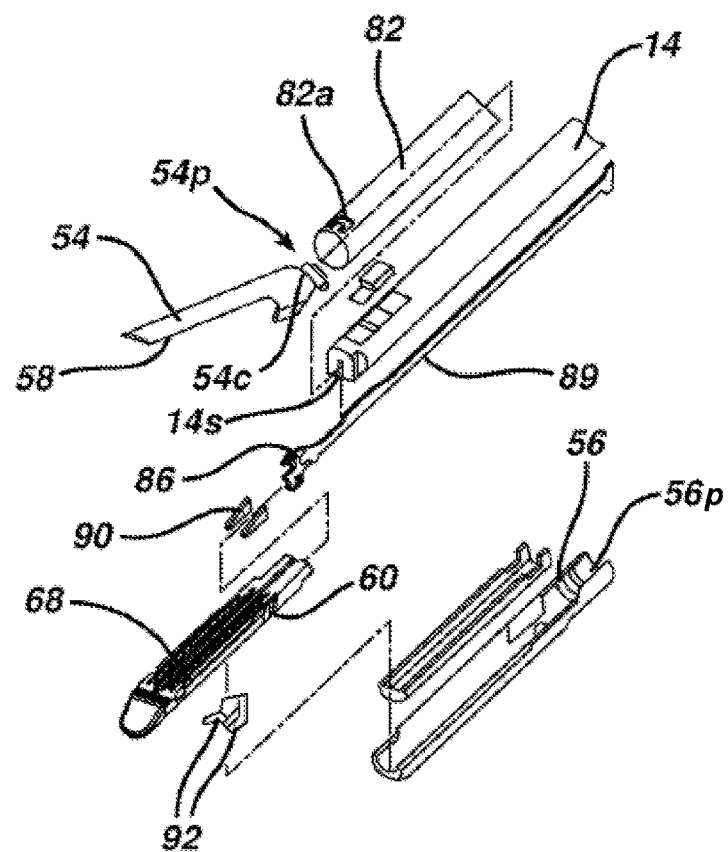
FIG. 4 is an exploded perspective view of an end effector and a distal end of a shaft of the instrument of FIG. 3.

As shown in more detail in FIG. 4, the end effector 50 of the illustrated embodiment is a surgical stapling tool having a lower jaw 52 that serves as a cartridge assembly or carrier and an opposed upper jaw 54 that serves as an anvil. The staple cartridge 60, having a plurality of staples 70 therein, is supported in a staple tray 57, which in turn is supported within the cartridge channel of the lower jaw 52. The upper jaw 54 has a plurality of staple forming pockets, each of which is positioned above a corresponding staple from the plurality of staples 70 contained within the staple cartridge 60. The upper jaw 54 can be connected to the lower jaw 52 in a variety of ways, although in the illustrated embodiment the upper jaw 54 has a proximal pivoting end 54p that is pivotally received within a proximal end 56p of the staple channel 56, just distal to its engagement to the shaft 14. When the upper jaw 54 is pivoted downwardly, the upper jaw 54 moves the anvil surface 58 and the staple forming pockets formed thereon move toward the opposing staple cartridge 60.

Various clamping components can be used to effect opening and closing of the jaws 52, 54 to selectively clamp tissue therebetween. In the illustrated embodiment, the pivoting end 54p of the upper jaw 54 includes a closure feature 54c distal to its pivotal attachment with the staple channel 56. Thus, a closure tube 82, whose distal end includes a horseshoe aperture 82a that engages the closure feature 54c, selectively imparts an opening motion to the upper jaw 54 during proximal longitudinal motion and a closing motion to the upper jaw 54 during distal longitudinal motion of the closure tube 82 in response to the clamping trigger 22. It will be appreciated by a person skilled in the art that opening and closure of the end effector 50 may be effected by relative motion of the lower jaw 52 with respect to the upper jaw 54, relative motion of the upper jaw 54 with respect to the lower jaw 52, or by motion of both jaws 52, 54 with respect to one another.

Figure 5:
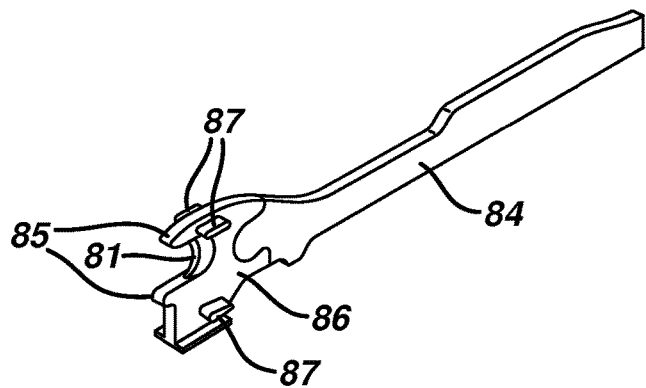
FIG. 5 is a perspective view of an E-beam component of the instrument of FIG. 3.

The firing components of the illustrated embodiment can include a firing bar 84, as shown in FIG. 5, having an E-beam 86 on a distal end thereof. The firing bar 84 is encompassed within the shaft 14, for example in a longitudinal firing bar slot 14s of the shaft 14, and guided by a firing motion from the handle 12. Actuation of the firing trigger 24 can affect distal motion of the E-beam 86 through at least a portion of the end effector 50 to thereby cause the firing of staples 70 contained within the staple cartridge 60. In the illustrated embodiment, guides 85 projecting from a distal end of the E-Beam 86 can engage a wedge sled 90, which in turn can push staple drivers 92 upwardly through staple cavities 68 formed in the staple cartridge 60. Upward movement of the staple drivers 92 applies an upward force on each of the plurality of staples 70 within the cartridge 60 to thereby push the staples 70 upwardly against the anvil surface 58 of the upper jaw 54 and to create formed staples 70'.

In addition to causing the firing of staples, the E-beam 86 can be configured to facilitate closure of the jaws 52, 54, spacing of the upper jaw 54 from the staple cartridge 60, and/or severing of tissue captured between the jaws 52, 54. In particular, a pair of top pins 87 and a pair of bottom pins 89 can engage one or both of the upper and lower jaws 52, 54 to compress the jaws 52, 54 toward one another as the firing bar 84 advances through the end effector 50. Simultaneously, a knife 81 extending between the top and bottom pins 87, 89 can be configured to sever tissue captured between the jaws 52, 54.

In use, the surgical stapler 10 can be disposed in a cannula or port and disposed at a surgical site. A tissue to be cut and stapled can be placed between the jaws 52, 54 of the surgical stapler 10. Features of the stapler 10 can be maneuvered as desired by the clinician to achieve a desired location of the jaws 52, 54 at the surgical site and the tissue with respect to the jaws 52, 54. After appropriate positioning has been achieved, the clamping trigger 22 can be pulled toward the stationary handle 20 to actuate the clamping system. The trigger 22 can cause components of the clamping system to operate such that the closure tube 82 advances distally through at least a portion of the shaft 14 to cause at least one of the jaws 52, 54 to collapse towards the other to clamp the tissue disposed therebetween. Thereafter, the trigger 24 can be pulled toward the stationary handle 20 to cause components of the firing system to operate such that the firing bar 84 and/or the E-beam 86 are advanced distally through at least a portion of the end effector 50 to effect the firing of staples 70 and optionally to sever the tissue captured between the jaws 52, 54.

Figure 6:
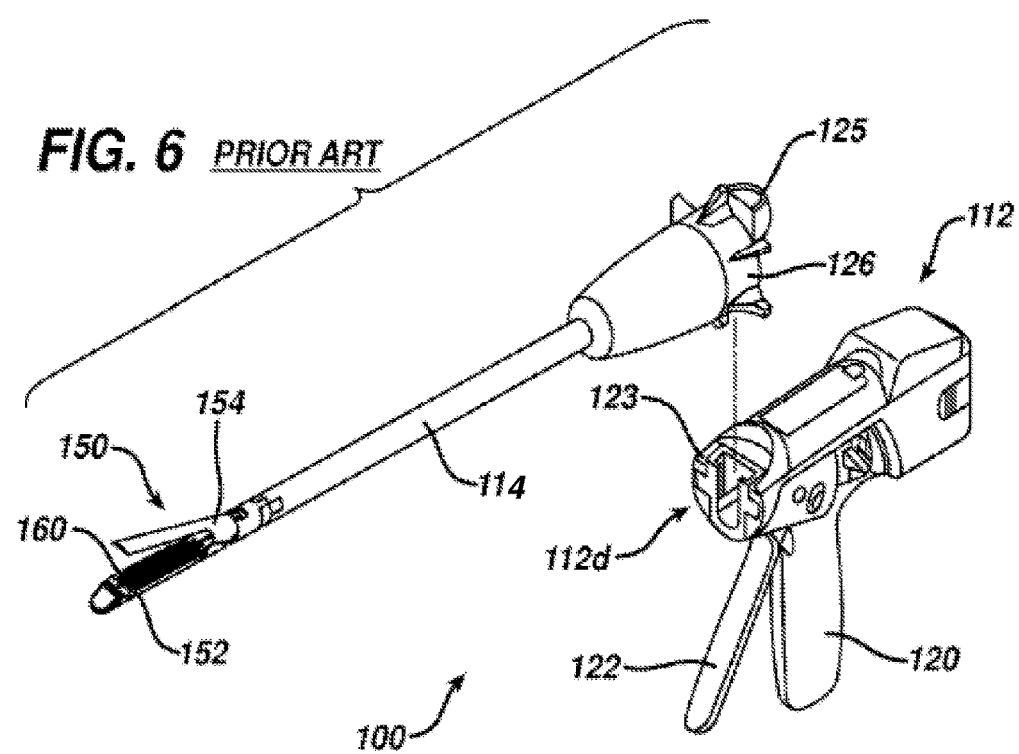
FIG. 6 is a perspective view of another prior art surgical instrument which can be used with one or more adjunct materials.

Another embodiment of a surgical instrument 100 is illustrated in FIG. 6. Like surgical instrument 10, surgical instrument 100 includes a handle assembly 112 with a shaft 114 extending distally therefrom and having an end effector 150 on a distal end thereof for treating tissue. Upper and lower jaws 154, 152 of the end effector 150 can be configured to capture tissue therebetween, staple the tissue by firing of staples from a cartridge 160 disposed in the lower jaw 154, and/or to create an incision in the tissue. In this embodiment, an attachment portion on a proximal end of the shaft 114 can be configured to allow for removable attachment of the shaft 114 and the end effector 150 to the handle assembly 112. In particular, mating features 125 of the attachment portion can mate to complementary mating features 123 of the handle assembly 112. The mating features 123, 125 can be configured to couple together via, e.g., a snap fit coupling, a bayonet type coupling, etc., although any number of complementary mating features and any type of coupling can be used to removably couple the shaft 114 to the handle assembly 112. Although the entire shaft 114 of the illustrated embodiment is configured to be detachable from the handle assembly 112, in some embodiments the attachment portion can be configured to allow for detachment of only a distal portion of the shaft 114. Detachable coupling of the shaft 114 and/or the end effector 150 can allow for selective attachment of a desired end effector 150 for a particular procedure, and/or for reuse of the handle assembly 112 for multiple different procedures.

The handle assembly 112 can have one or more features thereon to manipulate and operate the end effector 150. By way of non-limiting example, a rotation knob 126 mounted on a distal end of the handle assembly 112 can facilitate rotation of the shaft 114 and/or the end effector 150 with respect to the handle assembly 112. The handle assembly 112 can further include clamping components as part of a clamping system actuated by trigger 122 and firing components as part of a firing system that can also be actuated by the trigger 122. Thus, in some embodiments, movement of the trigger 122 toward a stationary handle 120 through a first range of motion can actuate clamping components to cause opposed jaws 152, 154 to approximate toward one another to a closed position. Further movement of the trigger 122 toward the stationary handle 120 through a second range of motion can actuate firing components to cause the ejection of staples from the staple cartridge 160 and/or the advancement of a knife to sever tissue captured between the jaws 152, 154.

Figure 7:
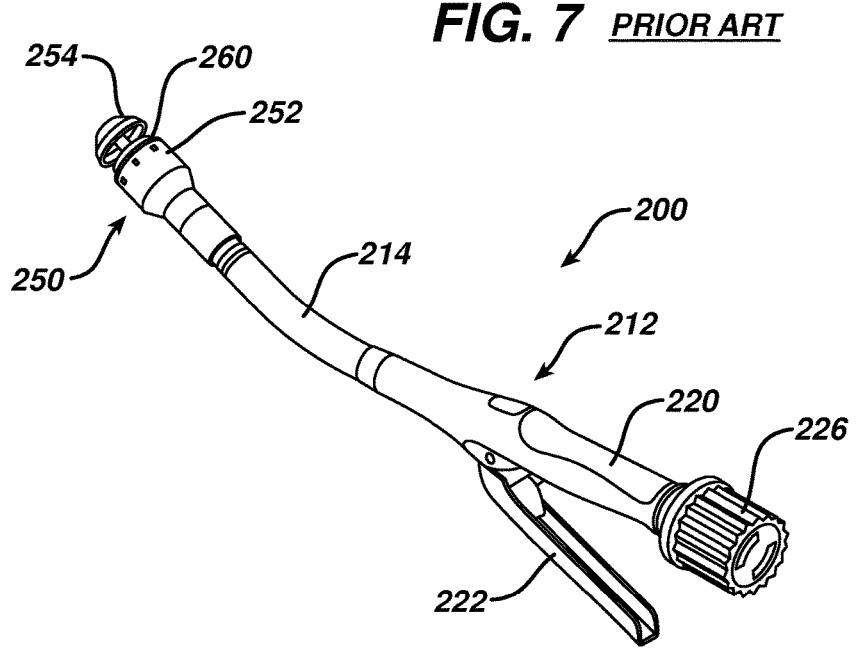
FIG. 7 is a perspective view of another prior art surgical instrument which can be used with one or more adjunct materials.

Yet another embodiment of a surgical instrument 200 is illustrated in FIG. 7. Like surgical instruments 10 and 100, surgical instrument 200 includes a handle assembly 212 with a shaft 214 extending distally therefrom and having an end effector 250 on a distal end thereof for treating tissue. The end effector 250 can include a cartridge assembly 252 and an anvil 254, each having a tissue-contacting surface that is substantially circular in shape. The cartridge assembly 252 and anvil 254 can be coupled together via a shaft extending from the anvil 254 to the handle assembly 212 of the stapler 200, and manipulating an actuator 222 on the handle assembly 220 can retract and advance the shaft to move the anvil 254 relative to the cartridge assembly 252. In one embodiment, the shaft can be formed of first and second portions (not shown) configured to releasably couple together to allow the anvil 254 to be detached from the cartridge assembly 252, allowing greater flexibility in positioning the anvil 254 and the cartridge assembly 252 in a body. For example, the first portion of the shaft can be disposed within the cartridge assembly 252 and extend distally outside of the cartridge assembly 252, terminating in a distal mating feature. The second portion of the shaft 214 can be disposed within the anvil 254 and extend proximally outside of the cartridge assembly 252, terminating in a proximal mating feature. In use, the proximal and distal mating features can be coupled together to allow the anvil 254 and cartridge assembly 252 to move relative to one another. The anvil 254 and cartridge assembly 252 can perform various functions and can be configured to capture tissue therebetween, staple the tissue by firing of staples from a cartridge assembly 252 and/or can create an incision in the tissue. In general, the cartridge assembly 252 can house a cartridge containing the staples and can deploy staples against the anvil 254 to form a circular pattern of staples around a circumference of a tubular body organ.

The handle assembly 212 of the stapler 200 can have various actuators disposed thereon that can control movement of the stapler. For example, the handle assembly 212 can have a rotation knob 226 disposed thereon to facilitate positioning of the end effector 250 via rotation, and/or a trigger 222 for actuation of the end effector 250. Movement of the trigger 222 through a first range of motion can actuate components of a clamping system to approximate the jaws, i.e. move the anvil 254 toward the cartridge assembly 252. Movement of the trigger 222 through a second range of motion can actuate components of a firing system to cause the staples to deploy from the staple cartridge assembly 252 and/or cause advancement of a knife to sever tissue captured between the cartridge assembly 252 and the anvil 254.

The illustrated embodiments of surgical stapling instruments 10, 100, and 200 provide only a few examples of many different configurations, and associated methods of use, that can be used in conjunction with the disclosures provided herein. Although the illustrated embodiments are all configured for use in minimally invasive procedures, it will be appreciated that instruments configured for use in open surgical procedures, e.g., open linear staplers as described in U.S. Pat. No. 8,317,070, can be used in conjunction with the disclosures provided herein. Greater detail on the illustrated embodiments, as well as additional exemplary embodiments of surgical staplers, components thereof, and their related methods of use, that can be used in accordance with the present disclosure include those devices, components, and methods provided for in U.S. Publication No. 2013/0256377, U.S. Pat. No. 8,393,514, U.S. Pat. No. 8,317,070, U.S. Pat. No. 7,143,925, U.S. patent application Ser. No. 14/074,884, entitled "Sealing Materials for Use in Surgical Procedures, and filed on Nov. 8, 2013, U.S. patent application Ser. No. 14/074,810, entitled "Hybrid Adjunct Materials for Use in Surgical Stapling," and filed on Nov. 8, 2013, U.S. patent application Ser. No. 14/075,438, entitled "Positively Charged Implantable Materials and Method of Forming the Same," and filed on Nov. 8, 2013, U.S. patent application Ser. No. 14/075,459, entitled "Tissue Ingrowth Materials and Method of Using the Same," and filed on Nov. 8, 2013, U.S. patent application Ser. No. 14/074,902, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, each of which is incorporated by reference herein in its entirety.

Exemplary Compositions for Adjunct Materials

Regardless of the configuration of the surgical instrument, the embodiments described herein can provide for the use of implantable materials, e.g., synthetic and/or biological materials, collectively "adjunct materials," in conjunction with instrument operations. As explained in more detail below, adjunct materials as disclosed herein can be releasably coupled to the lower and upper jaw members 52, 54 in a variety of manners to allow the adjunct materials to separate from the jaw members upon actuation of the end effector 50. More particularly, the adjunct materials can be captured by staples 70 along with tissue disposed between the jaw members 52, 54. The adjunct materials can remain in the patient when the stapler removed from the patient. While a number of devices and methods for attaching adjunct materials to an end effector of a surgical instrument are described below, others can be found in U.S. Pat. Pub. No. 2013/0256377 and U.S. Pat. Pub. No. 2013/0153641, incorporated herein by reference in their entirety.

Adjunct material used in conjunction with the disclosures provided for herein can have any number of configurations and properties. Generally, they can be made from a bioabsorbable material, a biofragmentable material, and/or a material otherwise capable of being broken down, for example, such that the adjunct material can be absorbed, dissolved, fragmented, and/or broken down during the healing process. In at least one embodiment, the adjunct material can be configured to degrade over time to form a gel, e.g., a sealant, to assist in wound healing. In other embodiments, the adjunct material can include a therapeutic drug that can be configured to be released over time to aid the tissue in healing, for example. In further various embodiments, the adjunct materials can include a non-absorbable and/or a material not capable of being broken down, for example.

Some particularly advantageous adjunct materials can include porous polymer scaffolds that can be configured to be broken down, for example by exposure to water such that the water attacks the linkage of a polymer of the material. The degraded material can be configured to gel over a wound site to thereby coat the wounded tissue, e.g., wounded soft tissue, which can aid in compressing, sealing and/or generally creating an environment at the wound site that promotes healing of the tissue. In particular, such degradable polymers can allow for the tissue itself to become the weight-bearing component. In some embodiments, the degraded material can include chemoattractant agents that attract natural healing compounds to the wound site. The polymer scaffolds can be configured to have a desired rate of degradation, for example within minutes to hours after attachment to tissue, to thereby assist in the healing process almost immediately after attachment. For more details on porous polymer scaffolds as described herein, see Q. Chen et al., Elastomeric biomaterials for tissue engineering, Progress in Polymer Science 38 (2013) 584-671, incorporated herein by reference in its entirety.

In some embodiments, the porous polymer scaffolds described herein can be physically crosslinked, which can allow for shaping of the polymer into various complicated three-dimensional shapes, e.g., fibers, sheets, films etc., having any desired porosity, surface-to-volume ratio, and mechanical properties. The scaffold can be shaped into a desired form via a number of methods, for example by extrusion, wet spinning, electrospinning, thermally induced phase separation (TIPS), salt leaching/freeze-drying, etc. Where the scaffold is formed into a film or sheet, the film or sheet can have any desired thickness, for example in a range of about 50 to 750 µm or in a range of about 1 to 3 mm, depending on the desired application.

One embodiment of a porous polymer scaffold includes multiple layers, each of which can perform different wound healing functions. In an exemplary embodiment, the scaffold includes three layers. The first layer can be made from polyester carbonate urethane urea (PECUU), the second layer can be made from poly(ester urethane) urea (PEUU), and the third layer can be made from poly(carbonate urethane) urea (PCUU) lysine triisocyanate (LTI) or hexamethylene diisocyanate (HDI). A person skilled in the art will appreciate that the properties of each layer can be optimized to achieve desired results and performance. In some embodiments, the desired properties of the scaffold can be achieved by blending or copolymerizing the material of the third layer or copolymerized with various polymers or copolymers. By way of non-limiting examples, the material of the third layer can be blended with a polyester copolymer, for example polycaprolactone (PCL), polyglycolic acid PGA, poly(D,L-lactic acid) (PDLLA), PGA, and/or polyethylene glycol (PEG). Where the material of the third layer is blended with both the polyester copolymer and the PEG, a ratio of the polyester to the PEG in the third layer can be about 50:50. In another exemplary embodiment, the PCL can be present in a range of about 60-70% weight/volume, the PGA can be present in a range of about 20-30% weight/volume, the PEG can be present in a range of about 50% weight/volume, and the PDLLA can be present in a range of about 10% weight/volume.

The three-layered film can be configured to degrade almost immediately upon attachment to tissue, for example within about 1 to 2 hours after attachment, although each of the three layers can be configured to degrade differently to have different healing benefits. The order, number, and thickness of each of the layers can vary, and can be tailored to create desired degradation and/or compression ratios. In some embodiments, the first, second, and third layers can be formed on top of a base material or substrate, for example on top of PCL, which can be configured to aid in mechanical compression of the wounded tissue.

Another exemplary embodiment of a porous polymer scaffold can be synthesized from polyhydroxyalkanoate (PHA). In an exemplary embodiment, the PHA can be naturally produced from a variety of microorganisms, e.g., Gram-negative or Gram-positive bacteria, or it can be synthesized, e.g., similar to the production of Biopol®, available from Zeneca of London, United Kingdom. Because PHAs are very quick to dissolve, scaffolds made from PHA can begin to degrade within 20 to 30 minutes after attachment to tissue via contact with heat and/or water. Where the PHA scaffold has a higher molecular weight, the degradation time can be higher, for example in a range of about 30 minutes to about 10 hours. The PHA can be formed into a very thin film, for example a film having a thickness of less than 0.1 mm, e.g., in a range of between 50 to 750 µm. In some embodiments, the PHA can be copolymerized and/or blended with one or more additional materials. By way of non-limiting example, the PHA can be copolymerized with hydroxlvalerate (HV), hydroxylbutyrate (HB), and/or hydroxylhexanoate (HH), which can reduce a level or crystallinity and/or brittleness of the PHA. In other embodiments, the PHA can be blended with one or more thermoplastics, e.g., poly(lactic acid) (PLA), PGA, PCL, starch, etc., to thereby customize a molecular weight and resultant mechanical properties of the scaffold. In certain aspects, one or more of the polymers can be a thermoplastic polymer.

In other embodiments, the scaffold can be synthesized from poly(polyol sebacate) (PPS), e.g., from poly(glycerol-sebacate) (PGS). Such scaffolds can be particularly biocompatible and can provide an additional advantage of reducing a risk of infection in addition to promoting healing. Other exemplary embodiments can be synthesized from xylitol-based elastomers, for example polyxylitol sebacates (PXSs), which can offer structural stability over a clinically required period and/or can enter the metabolic pathway slowly without causing rapid fluctuations of blood glucose levels. Scaffolds made from PXS's can be formed into a thicker film to thereby provide greater compression to the wound site, and can be configured to degrade within a range of about 10 hours to 8 days after attachment. Still other exemplary embodiments can be synthesized from poly(glycerol sebacate-co-acrylate) (PGSA), which can promote tissue ingrowth into the scaffold, particularly when formed as a fiber, and/or can serve as an anti-bacterial agent. PGSA scaffolds can be useful as a replacement for traditional surgical sutures and staples, and/or can serve as a waterproof sealant for hollow organ anastomoses (e.g., ducts, intestine, etc.), 2D mesh grafts (e.g., treatment of hernias, ulcers, burns, etc.), and/or wound dressings (e.g., hemostatic patches, etc.). The PGSA can be combined with glycerol, which can allow the scaffold to last longer in situ, for example up to 20 days.

In yet another embodiment, the scaffold can be made from poly(ε-caprolactone) (PCL), which can be blended with silk fibroin (SF) and which can be formed into a very thin film. The PCL/SF blend can have highly biocompatible properties and/or can improve cell attachment and/or proliferation to the scaffold. For example, when implanted onto tissue, the scaffold can release fibroin into the tissue to thereby promote faster healing, nearly immediate hemostasis, and/or to attract fibroblasts in greater numbers. The PCL component can further assist in the healing process by providing mechanical compression of the wounded tissue. A higher PCL content can provide better mechanical properties, while a higher SF content can provide better degradation properties. In general, the PCL content can be in a range of about 50 to 90% weight/volume and the SF content can be in a range of about 10 to 50% weight/volume. More details on the properties and manufacturing methods for scaffolds made from PCL and SF can be found in Jun Sik Lim et al., Fabrication and Evaluation of Poly(epsilon-caprolactone)/Silk Fibroin Blend Nanofibrous Scaffold, Biopolymers 97: 265-275 (2012), incorporated herein by reference in its entirety.

In still further embodiments, the scaffold can include PCL coated with a gelatin. The scaffold can be arranged in one or more layers, for example with the PCL serving as a substrate. The PCL can function to increase a mechanical strength of the scaffold and/or can support fibroblast adhesion and cell proliferation. More details on the properties and manufacturing methods for scaffolds made from gelatin-coated PCL can be found in Pengcheng Zhao et al., Biodegradable fibrous scaffolds composed of gelatin coated poly (ε-caprolactone) prepared by coaxial electrospinning, J. Biomed Mater Res 83A: 372-382 (2007), incorporated herein by reference in its entirety.

Table 1 below outlines exemplary molecular weight ranges, approximate absorption times, and average dimensions of films made from the aforementioned porous polymer scaffold materials. It will be appreciated by a person skilled in the art that the ranges provided in Table 1 are not intended to be limiting, and that a molecular weight of any of the polymers described herein can be altered to obtain the desired degradation properties.

TABLE 1

| Film | Average molecular weight in Daltons | Approximate absorption times | Average thickness | Average length | Average width |
|---|---|---|---|---|---|
| Polyester carbonate urethane urea (PECUU) | 5,000 to 80,000 | 14 to 60 days | 10 µm to 1 mil | 25.4 to 100 mm | 10.3 to 12.7 mm |
| Poly(ester urethane)urea (PEUU) | 5,000 to 80,000 | 14 to 60 days | 10 µm to 1 mil | 25.4 to 100 mm | 10.3 to 12.7 mm |
| Poly(carbonate urethane)urea (PCUU) | 10,000 to 200,000 (preferably 15,000 to 50,000) | 14 to 60 days | 100 µm to 1 mil | 25.4 to 100 mm | 10.3 to 12.7 mm |
| Polyhydroxyalkanoate (PHA) | $2.107 \times 10^{29}$ | 7 to 60 days | 100 µm to 1 mil | 25.4 to 100 mm | 10.3 to 12.7 mm |

TABLE 1-continued

| Film | Average molecular weight in Daltons | Approximate absorption times | Average thickness | Average length | Average width |
|---|---|---|---|---|---|
| Poly(polyol sebacate) (PPS) | to $2.589 \times 1029$ 89,000 and 124,000 | 7 to 60 days | 100 μm to 1 mil | 25.4 to 100 mm | 10.3 to 12.7 mm |
| Polyxylitol sebacates (PXS's) | $1.47 \times 1027$ to $3.73 \times 1027$ | 7 to 60 days | 100 μm to 1 mil | 25.4 to 100 mm | 10.3 to 12.7 mm |
| Poly(glycerol sebacate-co-acrylate) (PGSA) | $5.8 \times 1026$ to $7.5 \times 1026$ | 7 to 60 days | 10 μm to 1 mil | 25.4 to 100 mm | 10.3 to 12.7 mm |
| Poly(ε-caprolactone); silk fibroin; scaffold (PCL/SF) Blend PCL/SF (50/50) | 25,000 to 325,000 (SF) $4.21 \times 1028$ to $4.81 \times 1028$ (PCL) | 21 to 60 days (SF) 2 to 3 years (PCL) | 10 μm to 1 mil | 25.4 to 100 mm | 10.3 to 12.7 mm |
| Gelatin coated PCL (poly (ε-caprolactone) | $3.01 \times 1028$ to $1.98 \times 1029$ (gelatin) $4.21 \times 1028$ to $4.81 \times 1028$ (PCL) | 7 days (gelatin) 2 to 3 years (PCL) | 100 μm to 1 mil | 25.4 to 100 mm | 10.3 to 12.7 mm |

Other suitable adjunct materials can include absorbable polyurethanes, e.g., polyurethanes derived from aromatic absorbable isocyanates that can be similar to methylene bis(phenyl isocyanate) (MDI) and chain extender diols. The absorbable polyurethanes can be configured to hydrolytically degrade into safe and biocompatible products upon hydrolysis. Non-limiting examples of hydrolysable aromatic isocyanates that can be used to form the absorbable polyurethanes include glycolate-diisocyanate, caprolactone-diisocyanate, glycolate-ethylene glycol-glycolate, glycolate-diethylene glycol-glycolate, lactate-diethylene glycol-lactate, trimester of gycolic acid with trimethylpropane, and tetraester of glycolic acid with pentaerythritol.

Another particularly advantageous adjunct material that can be used in conjunction with the disclosures provided herein are the materials that form the multilayered dressings disclosed in U.S. Publication No. 2006/0257458, incorporated herein in its entirety, which are particularly suited to absorb and retain fluids when compressed, e.g., by the application of staples. Other exemplary, non-limiting examples of synthetic materials that can be used in conjunction with the disclosures provided for herein, e.g., as a buttress, include biodegradable synthetic absorbable polymer such as a polydioxanone film sold under the trademark PDS® or with a Polyglycerol sebacate (PGS) film or other biodegradable films formed from PGA (Polyglycolic acid and various forms thereof, marketed under the trademarks Vicryl, Dexon, and/or Neoveil), PCL (Polycaprolactone), PLA or PLLA (Polylactic acid), PHA (polyhydroxyalkanoate), PGCL (poliglecaprone 25, sold under the trademark Monocryl), PANACRYL (Ethicon, Inc., Somerville, N.J.), Polyglactin 910, Poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), polydioxanone (PDO) and various forms thereof (e.g., marketed under the trademark PDS) or a blend or copolymerization of any of the above. Blends and/or copolymerizations of any of the aforementioned materials can be tailored to have a desired molecular weight and/or degradation rate.

Some non-limiting examples of biologic derived materials that can be used in conjunction with the disclosures provided for herein, e.g., as a sealant material, include platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized regenerated cellulose, regenerated cellulose, mussel-based adhesive, poly (amino acid), agarose, polyetheretherketones, amylose, hyaluronan, hyaluronic acid, whey protein, cellulose gum, starch, gelatin, silk, Progel®, available from Davol Inc. of Warwick, R.I., TachoSil®, available from Baxter of Deerfield, Ill., or other material suitable to be mixed with biological material and introduced to a wound or defect site, including combinations of materials, or any material apparent to those skilled in the art in view of the disclosures provided for herein. Biologic materials can be derived from a number of sources, including from the patient in which the biologic material is to be implanted, a person that is not the patient in which the biologic material is to be implanted, or other animals.

Additional disclosures pertaining to synthetic or polymer materials and biologic materials that can be used in conjunction with the disclosures provided herein can be found in U.S. Pat. No. 7,772,352, PCT Publication No. WO 2014/016819, U.S. Patent Application Publication No. 2006/0257458, U.S. Patent Application Publication No. 2012/0080335, U.S. Patent Application Publication No. 2012/0083835, U.S. Patent Application Publication No. 2013/0256372, U.S. Patent Application Publication No. 2013/0256365, U.S. Patent Application Publication No. 2013/0256376, U.S. patent application Ser. No. 13/710,931, entitled "Electrosurgical End Effector with Tissue Tacking Features," and filed on Dec. 11, 2012, and U.S. patent application Ser. No. 13/763,192, entitled "Multiple Thickness Implantable Layers for Surgical Stapling Devices," and filed on Feb. 8, 2013, each of which is incorporated by reference herein in its entirety.

In use, the adjunct material can come pre-loaded onto the device and/or the staple cartridge, while in other instances the adjunct material can be packaged separately. In instances in which the adjunct material comes pre-loaded onto the device and/or the staple cartridge, the stapling procedure can be carried out as known to those skilled in the art. For example, in some instances the firing of the device can be enough to disassociate the adjunct material from the device and/or the staple cartridge, thereby requiring no further action by the clinician. In other instances any remaining connection or retention member associating the adjunct material with the device and/or the staple cartridge can be removed prior to removing the instrument from the surgical site, thereby leaving the adjunct material at the surgical site. In instances in which the adjunct material is packaged separately, the material can be releasably coupled to at least one component of the end effector, e.g., the staple cartridge, prior to firing the device. The adjunct material may be refrigerated, and thus removed from the refrigerator and the related packaging, and then coupled to the device using a connection or retention member as described herein or otherwise known to those skilled in the art. The stapling procedure can then be carried out as known to those skilled in the art, and if necessary, the adjunct material can be disassociated with the device as described above.

Crown-Side Staple-Specific Adjuncts

Figure 8:
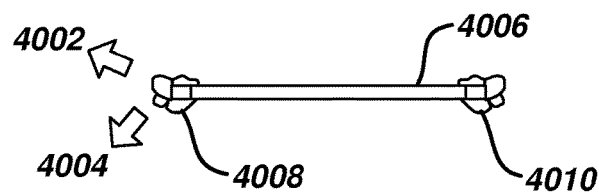
FIG. 8 is a top view of tissue damage that can occur near staple legs.

As mentioned above and shown in FIG. 8, punctures formed by staples fired from a surgical stapler may result in the leakage of blood, air, or other fluids depending on the type of tissue being stapled. More particularly, tissue can stretch in any of a variety of directions 4002, 4004 after a staple 4006 is implanted therein, thereby stretching punctures 4008, 4010 formed by the staple legs. In some cases, bleeding or other leakage through staple punctures can be present even though a stapled end of a vessel or other body lumen is successfully sealed.

One advantage of tissue adjuncts is their propensity to prevent or minimize leaks, such as fluid or gas leaks. Tissue adjuncts can perform this function by one or more of the following mechanisms: plugging holes or tears that occur at the staple puncture sites; restricting movement of tissue around staple puncture sites to prevent an increase in the size of staple holes and/or to prevent tissue tears; and minimizing strain gradients that occur between constrained tissues within the staple line and free tissue adjacent to the staple line.

Embodiments of the devices and methods described herein can address leakage from these punctures by providing one or more adjuncts that are coupled to a staple and configured to plug or seal the punctures 4008, 4010. As described above, the adjuncts can be formed from viscous coatings (e.g., bio-absorbable urethane, etc.) disposed in staple cavities of a cartridge body containing staples. Upon ejection from the cartridge body, the adjunct coatings can become plugs that fill punctures 4008, 4010 formed by the staple legs. The plugs can be compressed when the staples are formed through tissue, and as the adjunct material is compressed it can expand and fill any defects in the tissue that could create leak paths. The adjunct plugs can also serve to distribute pressure applied by the staple, thereby reducing the possibility of a staple pulling through the tissue and failing to fasten the tissue as intended (so-called "cheese wiring"). Still further, a viscous coating used as an adjunct material can also include other healing properties, as described above (e.g., antimicrobial properties, hemostats, etc.) or other features to help with the formation of staples (e.g., lubricants, etc.).

Figure 9A:
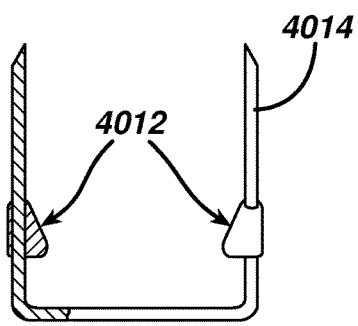
FIG. 9A is a side view of one embodiment of adjuncts coupled to a staple.

FIG. 9A illustrates one embodiment of adjuncts 4012 disposed about legs of a surgical staple 4014. The illustrated adjuncts 4012 are in the form of plugs disposed about each leg of the staple, that is, they have a tapered cylindrical shape configured to wedge into a puncture created by a staple leg as it passes through tissue. The adjuncts 4012 can be formed at any point along the legs of the staple 4014 and, in some embodiments, can be configured to slide along the legs, as described in more detail below.

Figure 9B:
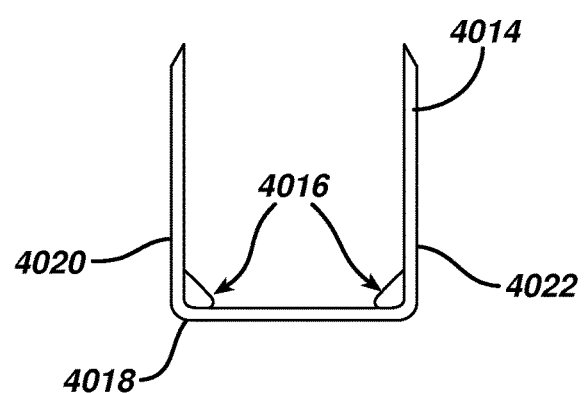
FIG. 9B is a side view of an alternative embodiment of adjuncts coupled to a staple.

In the embodiment shown in FIG. 9B, adjuncts 4016 can be positioned at a junction between a crown 4018 of the staple 4014 and each staple leg 4020, 4022. The adjuncts 4016 can again have a shape that tapers from the crown 4018 toward a distal end of the staple legs 4020, 4022 such that the adjunct forms a plug configured to be received within a puncture in tissue. The adjuncts 4016 can further be formed from a flowable material, e.g., a hydrogel, which can retain its shape prior to implantation but can become more flowable upon implantation in tissue to fill a puncture or other defect in the tissue. In other embodiments, a swellable material can be employed, i.e., a material that increases in volume upon contact with water or other bodily fluid.

Figure 10:
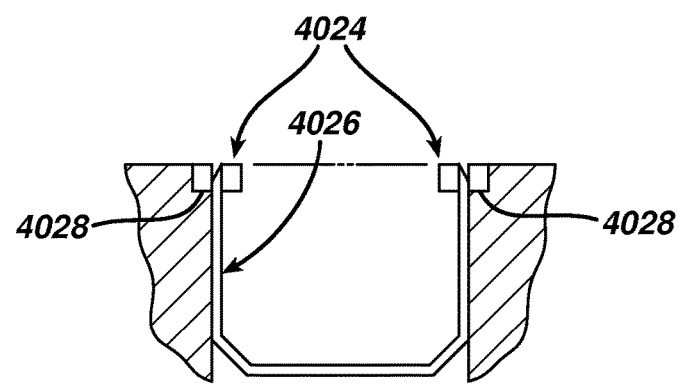
FIG. 10 is a cross-sectional view of one embodiment of adjuncts coupled to a staple.
Figure 11:
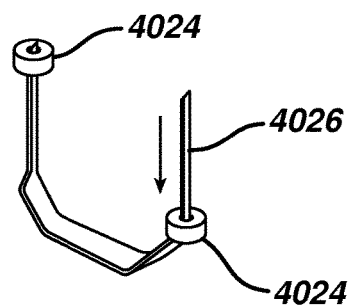
FIG. 11 is a perspective view of the adjuncts and staple of FIG. 10.

FIG. 10 illustrates an alternative embodiment of adjuncts 4024 disposed around legs of staple 4026. In this embodiment, the staple 4026 is housed within a staple cavity of a surgical stapler's cartridge body 4028. Adjunct plugs 4024 are disposed around each leg of the staple 4026 at a distal end thereof. In some embodiments, the adjuncts 4024 can be seated in small cut-outs or shelves formed in the cartridge body 4028 (compare to FIG. 12). The adjuncts 4024 can be configured to slide over the legs of staple 4026, as shown in FIG. 11.

In use, as shown in FIG. 12, tissue 4030 can be clamped between the cartridge body 4028 and an anvil 4032 and the staple 4026 can be ejected out of the cartridge body through the tissue and into the anvil. The adjuncts 4024 can abut against the tissue 4030 and begin to slide over the legs of the staple 4026 as it is ejected from the cartridge body (see FIG. 11). Ultimately the adjuncts 4024 can end up compressed between the tissue 4030 and a crown of the staple 4018. Because the adjuncts 4024 can be formed from a material that becomes flowable upon contact with water or other bodily fluid, or under compressive forces, the cylindrically-shaped adjuncts 4024 shown in FIG. 11 can flow into punctures in the tissue 4030, as shown in FIG. 12.

Viscous coatings and other flowable or swellable materials can be suitable choices for an adjunct material because they can adapt to varying forces experienced by tissue at different locations within the body. FIGS. 13A and 13B illustrate that such adjunct materials can be used to effectively seal staple leg punctures that expand inward toward one another, as can be the case when the tissue is under compression, as well as staple leg punctures that expand outward away from one another, as can be the case when the tissue is under tension. By way of example, tissue under tension can often be found in the thoracic cavity, e.g., lung tissue and/or cardiovascular tissue (FIG. 13B), while tissue under compression can often be found outside of the thoracic cavity (FIG. 13A).

Figure 14A:
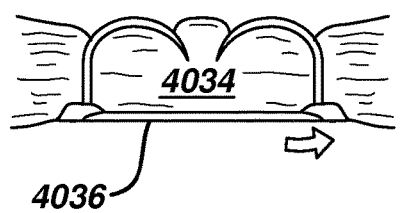
FIG. 14A is a side view of one embodiment of adjunct operation in tissue.
Figure 14B:
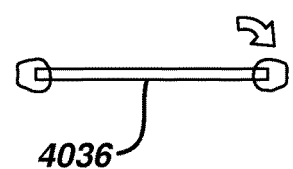
FIG. 14B is a top view of the adjunct operation shown in FIG. 14A.

FIGS. 14A and 14B provide alternative views of the configuration shown in FIG. 13B. Tissue 4034 that is under tension can cause staple leg punctures to expand outward from the staple 4036. Accordingly, flowable adjunct plugs 4038 in the form of gel plugs disposed around each leg of the staple 4036 can be pushed outward by compression between the crown of the staple and the tissue 4034 into the punctures. The gel can seal the expanded punctures, thereby preventing any leakage therethrough.

Figure 15:
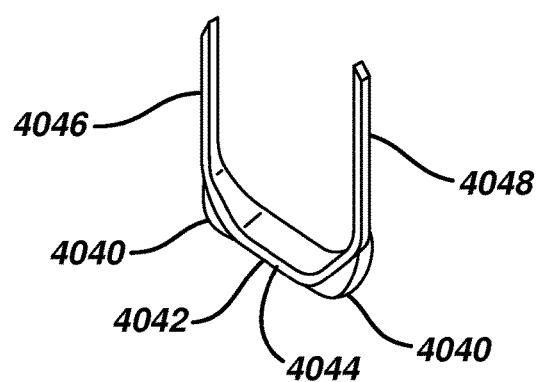
FIG. 15 is a perspective view of one embodiment of adjuncts coupled to a staple.

As noted above, FIGS. 9A-14B show adjunct material disposed around legs of a surgical staple or formed at an inner junction between a crown of the staple and the staple legs. In an alternative embodiment shown in FIG. 15, adjunct material 4040 can be coupled to an outer surface of the staple 4042 at the junction between a crown 4044 of the staple and each staple leg 4046, 4048. The adjunct material 4040 can be a flowable or swellable material in some embodiments, such as a hydrogel. Such a material can expand outward upon contact with tissue and fill the punctures formed by the staple legs 4046, 4048. The adjunct material 4040 in FIG. 15 is in the shape of a cylindrical plug, however any of a variety of other shapes are also possible. As mentioned above, other possible shapes can include taper along a leg of the staple, or entirely different shapes can be utilized, such as a cube, hexagonal extrusion, etc.

A shape of the staple 4042 can be modified to accommodate the adjunct material 4040, as shown in FIG. 16. In some embodiments, for example, right-angle corners of the staple 4014 shown in FIGS. 9A and 9B can be chamfered to provide attachment surfaces for the adjunct material 4040. The crown 4044 of the staple 4042 also has a broader, flat shape, as opposed to the cylindrical rod or square cross-sectional shape of the staple 4014 in FIG. 9. In addition, both the staple 4042 and the adjunct material 4040 can have any of a variety of sizes. FIGS. 17A-17C illustrate embodiments of staples 4050, 4052, and 4054 that have a same width and leg length, but accommodate increasing amounts of adjunct material 4056, 4058, 4060.

Figure 18A:
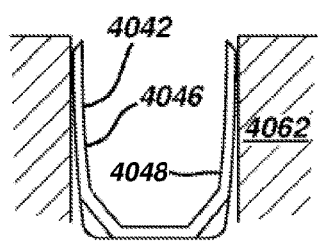
FIG. 18A is a cross-sectional view of the staple of FIG. 15 in a staple cartridge.
Figure 18B:
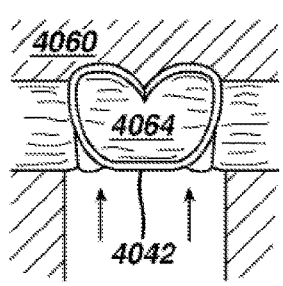
FIG. 18B is a cross-sectional view of the staple of FIG. 15 ejected into tissue.
Figure 18C:
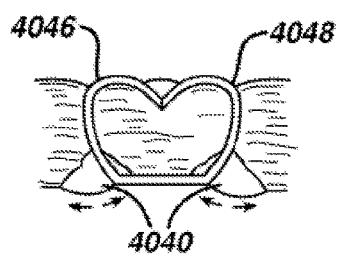
FIG. 18C is a cross-sectional view of the adjuncts sealing the staple of FIG. 15 in tissue.

FIGS. 18A-18C illustrate the implantation of the staple 4042 shown in FIG. 15 in a patient's lung. The staple 4042 can be initially stored within a staple cavity of a surgical stapler cartridge body 4062. Once tissue 4064 is disposed between the cartridge body 4062 and an anvil 4066, the staple 4042 can be ejected from the staple cavity through the tissue and into the anvil. Upon contact with the lung tissue 4064, the hydrogel adjunct material 4040 can expand to fill any gaps or defects surrounding the punctures formed by the staple legs 4046, 4048.

Figure 19A:
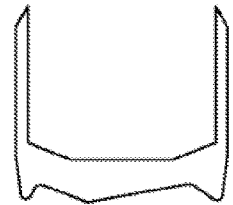
FIG. 19A is a side view of an alternative embodiment of a staple.
Figure 19B:
FIG. 19B is a side view of an alternative embodiment of a staple.

The flattened-crown staple of FIG. 15 is just one embodiment of a staple that can accommodate attachment of adjunct material thereto. FIGS. 19A and 19B illustrate still other alternative staple geometries that can have adjunct material coupled thereto, e.g., disposed about a leg thereof, or coupled to an outer or inner surface of a crown. U.S. patent application Ser. No. 14/138,516, filed on Dec. 23, 2013, the entirety of which is incorporated herein by reference, discloses still further staple geometries that can be combined with the adjunct materials disclosed herein. Regardless of the particular staple geometry or attachment mechanism for an adjunct material, the adjunct material can be configured to fill and seal individual punctures formed by the staple legs.

FIG. 20 illustrates an alternative embodiment of an adjunct in the form of a pledget 4066 that is configured to seal around both a first leg and a second leg of a surgical staple 4068. The pledget 4066 is shown pressed against a crown (not shown) of the staple 4068 and can be formed from a flowable and/or swellable material, such as a hydrogel or other gel, as discussed above. The gel can be configured to retain its shape when disposed within a surgical stapler cartridge body, as shown in FIG. 21A, but to become more flowable in all directions upon contact with tissue, water, or other fluid, as shown in FIG. 21B.

Figure 22A:
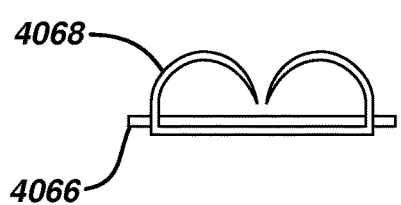
FIG. 22A is a side view of the staple of FIG. 20.
Figure 22B:
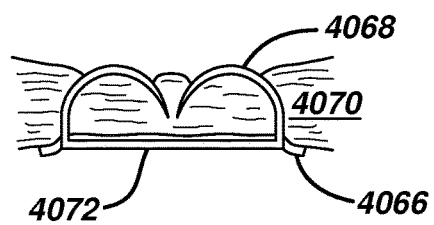
FIG. 22B is a cross-sectional view of the staple of FIG. 20 in tissue.

FIGS. 22A and 22B show the surgical staple 4068 and adjunct pledget 4066 from a side view before and after implantation. As shown in FIG. 22B, the pledget 4066 has expanded outward and flowed into tissue 4070 upon contact therewith. The gel material of the pledget 4066 can thereby seal the punctures formed by the staple 4068, as well as distribute pressure applied to the tissue by the a crown 4072 of the staple 4068.

Figure 23:
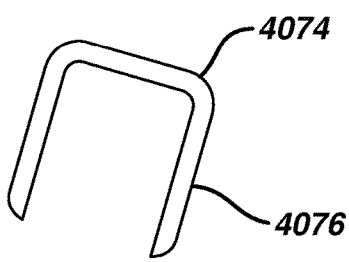
FIG. 23 is a perspective view of an alternative embodiment of an adjunct coupled to a staple.
Figure 24:
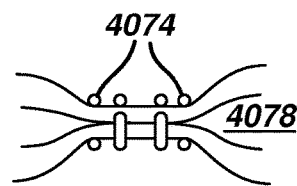
FIG. 24 is a side view of the staple of FIG. 23 in tissue.

In still other embodiments, adjunct material can be in the form of a coating disposed over all or a portion of a surgical staple, as shown in FIGS. 23 and 24. In particular, staple 4074 of FIG. 23 includes a coating 4076 of an adjunct material disposed over an entire outer surface thereof. The adjunct material employed in the coating 4076 can be configured to swell upon contact with tissue or bodily fluid, such that once the staple 4074 is implanted in tissue the coating will expand away from the staple and fill any gaps that may be present. FIG. 24 illustrates a side cross-sectional view of tissue 4078 having multiple rows of staples 4074 disposed therein. The staples 4074 can seal the tissue 4078 together at the center of the figure, such that fluid cannot pass and the tissue could be transected between the staples 4074.

Figure 25:
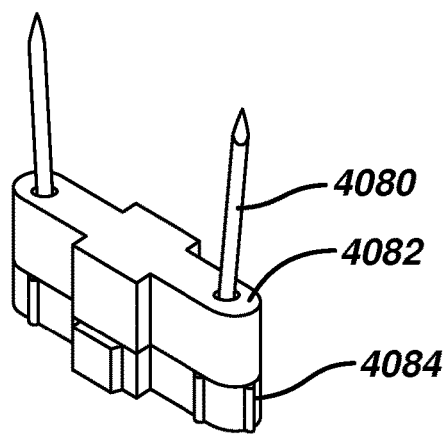
FIG. 25 is a perspective view of still another alternative embodiment of an adjunct coupled to a staple.

Other non-flowable materials can also be employed as adjuncts in some embodiments. For example, a compressible foam can be used as an adjunct material in combination with a gel or other flowable material, or on its own. FIG. 25 illustrates one embodiment of a staple 4080 having a foam adjunct 4082 disposed around both legs of the staple. Attempts to utilize foam in combination with staples may sometimes encounter a problem wherein the foam rotates about a crown of the staple during implantation. The staple 4080 addresses this problem, and minimizes this possibility, by incorporating an additional pledget 4084 between a crown of the staple and the foam adjunct 4082. The pledget 4084 can provide support to the foam adjunct 4082 during implantation to prevent it from rotating about the crown of the staple. The pledget 4084 can be formed from a rigid biocompatible material, or can be formed from a flowable material as described above. In the latter embodiment, a gel or other flowable material can retain its shape prior to implantation so as to provide the necessary support for the foam adjunct 4082, and subsequently flow into defects in tissue after implantation. U.S. Pat. Pub. No. 2011/0192882 to Hess et al., the entirety of which is incorporated herein by reference, discloses additional techniques for coupling staples to rigid pledgets and incorporating them into a cartridge body that can be combined with the adjunct materials disclosed herein.

In some embodiments, it can be desirable to prevent any adjunct material from coming into contact with the cartridge body of the surgical stapler during implantation of a staple. If there is contact between the cartridge body and adjuncts, it is possible that the adjunct material can be scraped off the staple as it is ejected from the cartridge body. In embodiments where the adjunct material is a hydrogel or other flowable and/or swellable material, it is further possible that the adjunct material could interfere with ejection of a staple if it was, for example, scraped off into a staple cavity and left to expand there or flow into neighboring portions of the surgical stapler. Accordingly, in certain embodiments sealing adjuncts disposed within a staple cavity of a surgical stapler cartridge body can be configured to be ejected therefrom along with a staple without contacting the cartridge body.

There are a number of ways to ensure that the adjuncts do not contact the cartridge body. In one embodiment, adjunct material can be coupled to a staple such that the staple shields the adjunct from contact with the cartridge body during ejection. The staple shown in FIG. 15 is one example of a staple that shields adjunct material from contact with the cartridge body because the adjunct material is essentially behind the staple as it is ejected from the cartridge body. In other embodiments, adjunct material can be tucked into an area extending between the legs of a staple, such as in the staple shown in FIG. 9B. This configuration can also shield the adjunct material from contacting the cartridge body during ejection from a staple cavity.

Figure 26:
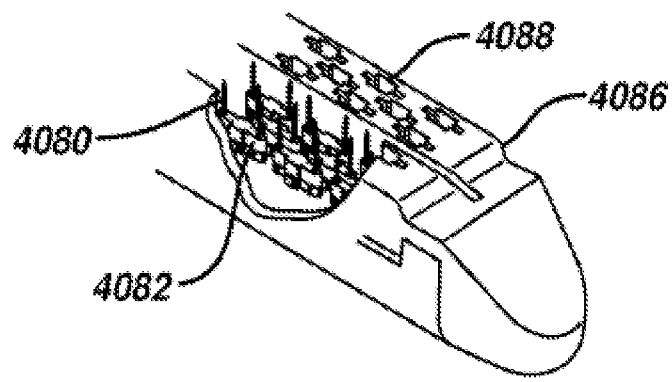
FIG. 26 is a perspective view of one embodiment of a staple cartridge housing a plurality of staples having adjuncts coupled thereto.

In other embodiments, the staple cavity openings in the cartridge body can be shaped to accommodate passage of at least one sealing adjunct coupled to a surgical staple. FIG. 26 illustrates one embodiment of a cartridge body 4086 that includes a plurality of staple cavities 4088 having openings shaped to accommodate the staple 4080 and foam adjunct 4082 shown in FIG. 25.

Figure 27:
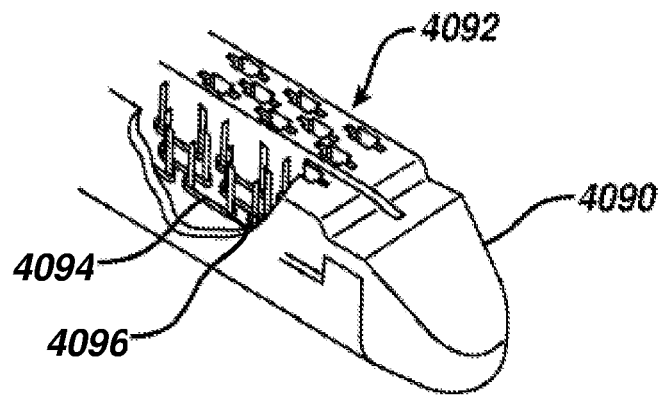
FIG. 27 is a perspective view of an alternative embodiment of a staple cartridge housing a plurality of staples having adjuncts coupled thereto.
Figure 28A:
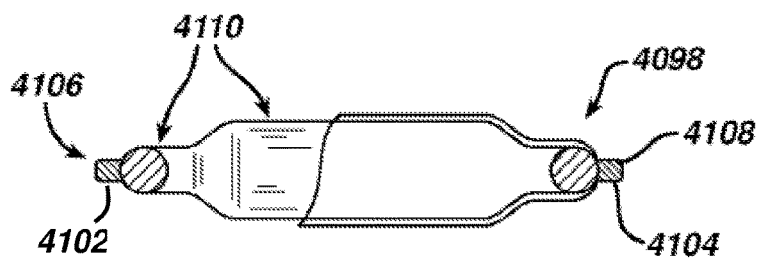
FIG. 28A is a top view of one embodiment of a staple cartridge ejection slot that accommodates a staple having an adjunct coupled thereto.
Figure 28B:
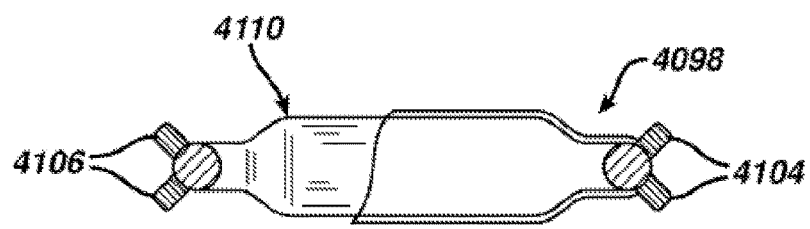
FIG. 28B is a top view of an alternative embodiment of a staple cartridge ejection slot that accommodates a staple having an adjunct coupled thereto.
Figure 28C:
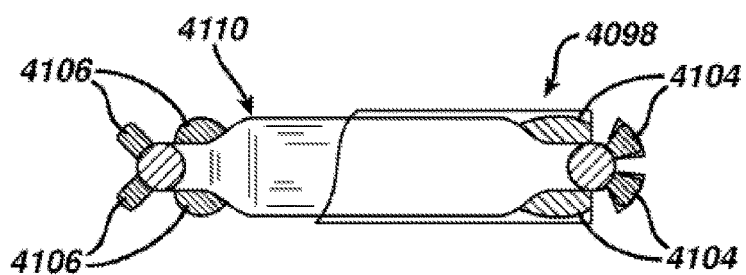
FIG. 28C is a top view of still another alternative embodiment of a staple cartridge ejection slot that accommodates a staple having an adjunct coupled thereto.

FIG. 27 illustrates an alternative embodiment of a cartridge body 4090 having a plurality of staple cavities 4092 shaped to accommodate a staple 4094 having a plurality of adjuncts 4096 coupled to an outer portion of each staple leg. FIGS. 28A-28C illustrate various embodiments of staple cavity openings that are configured to allow for passage of one or more adjuncts coupled to a surgical staple. In the top view of FIG. 28A, for example, a deck 4098 of the cartridge body is shown having an opening formed therein. The opening can include cut-outs 4102, 4104 formed at opposite ends thereof that are sized to accommodate sealing adjuncts 4106, 4108 that are coupled to a flat form staple 4110 that is similar to the staple shown in FIG. 15. In the alternative embodiments of FIGS. 28B and 28C, additional cut-outs are provided surrounding the legs of the staple 4110 to accommodate different configurations of adjunct material coupled thereto.

Anvil-Side Segmented Adjuncts

Certain embodiments of the methods and devices described herein include one or more adjunct segments disposed on an anvil-side of a surgical stapler, that is to say on an opposite side of staple tissue from the crown-side adjuncts described above. These anvil-side adjuncts can be used in addition to the crown-side adjuncts. While the crown-side adjuncts serve to prevent leakage caused by tissue deformation around the staple legs, the anvil-side adjuncts described below can prevent tissue damage from strain caused by the staple and the staple-line as a whole.

Adjunct segments disposed on the anvil-side of a surgical stapler can include sheets of biocompatible or bioresorbable material, discrete adjunct segments each designed to interact with legs of an individual staple, discrete adjunct segments each designed to interact with legs of multiple staples, discrete adjunct segments attached to each other, or any suitable combination thereof. In some embodiments, each adjunct can be of a size that when placed adjacent the anvil-side of a surgical stapler, each adjunct spans only a single staple-forming opening. Further, in some embodiments, each adjunct can be of a size that when placed adjacent the anvil-side of a surgical stapler, each adjunct spans multiple single staple-forming openings.

In addition to preventing damage from the staple in the stapled tissue, adjunct segments disposed on the anvil-side of a surgical stapler can serve to hold together staples that do not interact with tissue during a stapling procedure, that is to say excess staples. For example, in embodiments where the anvil-side adjuncts include sheets of material, adjunct segments that are each designed to interact with the legs of multiple staples, or adjunct segments that are attached to each other, a surgical stapler can be fitted across a segment of tissue, such as a portion of intestinal tissue or a vessel, whose diameter is shorter than the length of the staple line created by the surgical stapler. In that case, there will be staples that do not pass through tissue. Removal of those excess staples that are not securing tissue from the patient is facilitated if they remain attached to the tissue through the adjunct segments. The surgeon or stapler operator can then sever select adjuncts to detach the excess staples and he or she can remove all of the excess staples while minimizing the potential for loss of an excess staple inside the patient.

Though, as described in more detail below, some embodiments of the segmented adjuncts described herein can be used on a cartridge, adjunct segments can be deposited to the anvil-side of the surgical stapler in the staple shaping depressions in the anvil-side of the surgical stapler as a liquid that hardens over time or after exposure to curing radiation. Adjuncts can also be supplied as discrete adjuncts attached to a sheet. The sheet can be a connective film, such as continuous film. The sheet can be a woven mesh. In some embodiments, a plurality of discrete adjuncts can be connected through a plurality of connecting branches, through a plurality of threads, or other suitable means for connecting the adjuncts with biocompatible or bioresorbable material that does not impede the functioning of the staples or irritate the tissue once the staples are applied. When the adjuncts used are connected through a plurality of connecting branches, the surgical stapler can include one or more features to sever the connecting branches as the staples are deployed into tissue.

Figure 29:
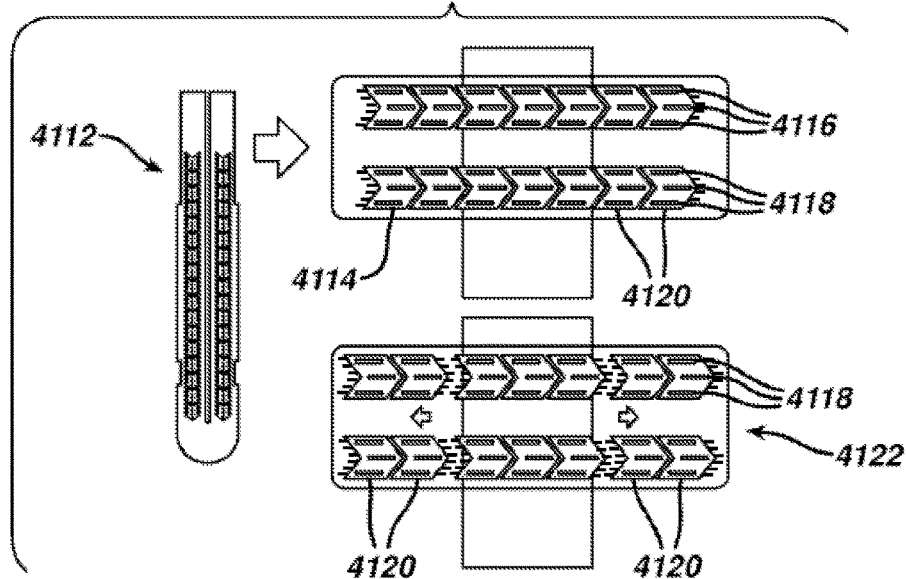
FIG. 29 is a top view of one embodiment of a plurality of adjunct segments coupled to one another.

FIG. 29 shows a top view of one embodiment of a plurality of adjunct segments coupled to one another 4112, such as might be seated in a cartridge for use with a surgical stapler or seated directly in a surgical stapler. The individual adjunct segments 4114 are shown to span a plurality of staple forming openings 4116, and when applied to tissue, as seen in the top portion of the figure on the right, there can be excess adjunct segments 4120 that do not attach to tissue. The individual adjunct segments 4114 are joined together through branches 4118. The branches 4118 can be made of a similar material as the adjuncts, but made thinner than the adjuncts and of a diameter that allows for the branches 4118 to be broken 4122 by the application of force. In this way, excess adjunct segments 4120 can be removed.

Figure 30:
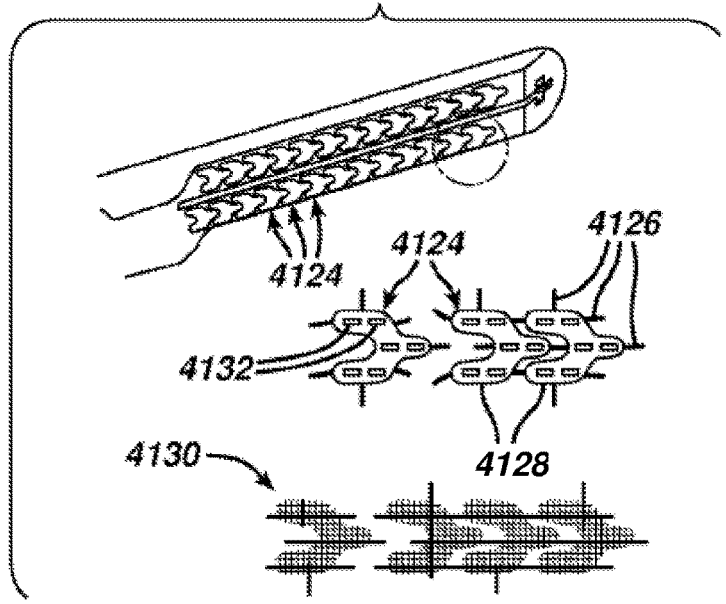
FIG. 30 is a perspective view of an alternative embodiment of a plurality of adjunct segments.

FIG. 30 shows a perspective view of an alternative embodiment of a plurality of adjunct segments 4124 applied on the anvil-side of a surgical stapler. The plurality of adjunct segments 4124 shown are held together by connecting threads of filaments 4126 between individual adjunct segments 4128. Each adjunct segment 4128 is configured to span a plurality of staple forming openings 4132.

A film that may include a woven material 4130 can overlay the individual segmented adjuncts 4128. The film, optionally including a woven material 4130, can help to mitigate the damage to stapled tissue by distributing forces.

Figure 31A:
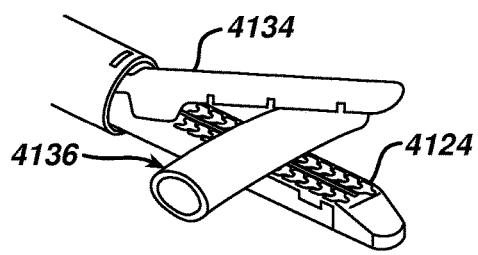
FIG. 31A is a perspective view of one embodiment of a surgical end effector having a plurality of adjunct segments accepting a vessel.
Figure 31B:
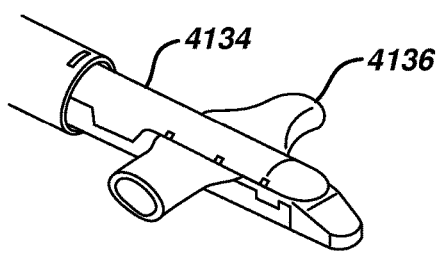
FIG. 31B is a perspective view of the surgical end effector of FIG. 31A stapling and transecting the vessel.
Figure 31C:
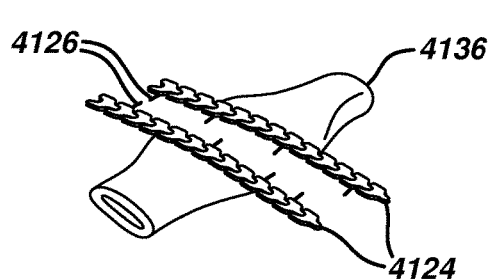
FIG. 31C is a perspective view of the vessel and adjuncts of FIG. 31A after transection.
Figure 31D:
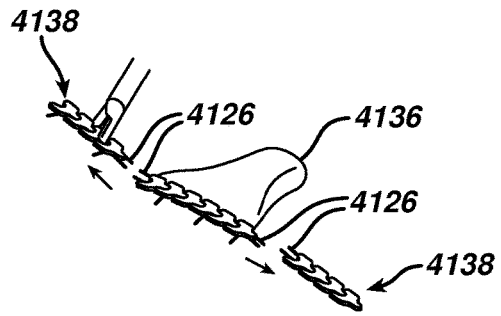
FIG. 31D is a perspective view of the vessel and adjuncts of FIG. 31A after excess adjuncts are removed.

FIG. 31A shows a view of one embodiment of surgical end effector 4134 having a plurality of adjunct segments 4124. The surgical end effector 4134 is shown accepting a vessel 4136. In FIG. 31B, the surgical end effector 4134 is shown transecting the vessel 4136, causing staples to engage with the adjunct segments 4124 of FIG. 31A. FIG. 31C shows the vessel 4136 and adjuncts 4124 after transection of the vessel 4136. Filaments or threads 4126 can connect the adjuncts 4124, and the filaments or threads 4126 can aid in the application of the plurality of adjuncts 4124 to the surgical end effector 4134. Yet the filaments or threads 4126 can be torn when separating the ends of the transected vessel 4136. The filaments or threads 4126 can hold excess adjunct segments 4138 in place until removed by a surgeon.

Figure 32:
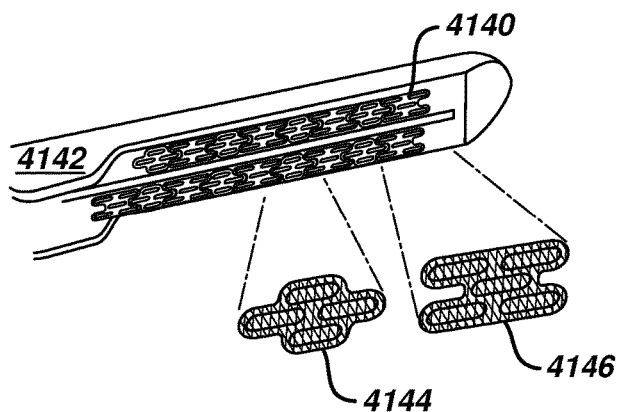
FIG. 32 is a perspective view of an alternative embodiment of a plurality of adjunct segments.

FIG. 32 shows another embodiment of segmented adjuncts 4140 disposed on the anvil-side of a surgical stapler 4142. Each individual adjunct segment 4144, 4146 spans multiple staple forming openings. As shown, each adjunct segment 4144, 4146 can have a distinct configuration from that of the adjunct segments adjacent to it. However, each adjunct segment 4144, 4146 interlocks with its neighbors. In this way, it may be possible to have some degree of adhesion between adjacent adjunct segments 4144, 4146 so that no filaments or branches are needed, and so that no filaments or partial branches will be exposed after the excess adjunct segments are removed from stapled tissue. Additionally, the adjuncts are shown as including a woven material.

Figure 33:
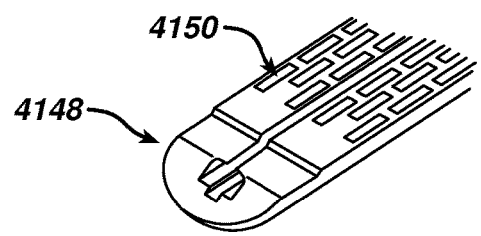
FIG. 33 is a perspective view of one embodiment of a surgical stapler anvil having a plurality of staple forming openings filled with a viscous sealant.
Figure 34:
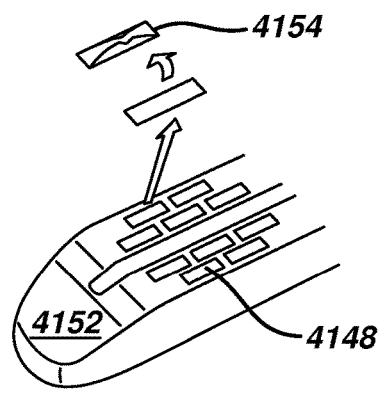
FIG. 34 is a perspective view of an alternative embodiment of a surgical stapler anvil having a plurality of staple forming openings filled with a viscous sealant.
Figure 35:
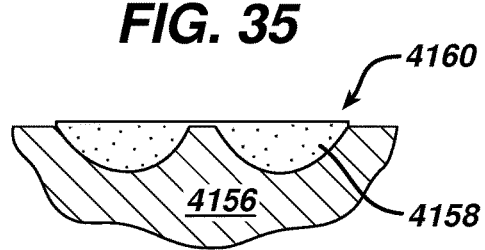
FIG. 35 is a cross-sectional view of one embodiment of a staple forming opening having a viscous sealant disposed therein and retained by a film.
Figure 36A:
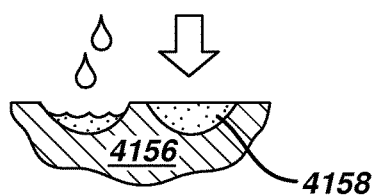
FIG. 36A is a cross-sectional view of one embodiment of a staple forming opening with a viscous sealant.
Figure 36B:
FIG. 36B is a cross-sectional view of the staple forming opening of FIG. 36A prior to curing.
Figure 36C:
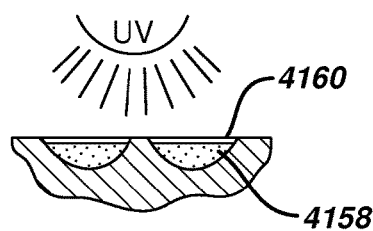
FIG. 36C is a cross-sectional view of the staple forming opening of FIG. 36A after partial curing.

FIG. 33 shows a portion of a surgical staple anvil 4148 with a plurality of staple forming openings filled with a viscous sealant material 4150. Some of the ways in which the material arrives in the staple forming openings of the staple anvil 4148 are shown in FIGS. 34-36D. FIG. 34 shows a surgical stapler anvil 4152 with staple forming openings in which pre-formed sealing gel 4154 is placed, as described in greater detail below. FIG. 35 is a cross sectional view of an anvil 4156 with staple forming openings filled with a sealing liquid or gel 4158. The sealing liquid or gel 4158 has a film or layer 4160, above the bulk of the sealing material, that is flush with the surface of the anvil 4156. FIG. 36A shows the addition of the sealing material 4158 in a liquid or gel state to staple forming openings on an anvil 4156. FIG. 36B shows the staple forming openings filled with sealing liquid or gel, and FIG. 36C shows the creation of the film or layer 4160. A light source, such as a UV light source, provides lights at an energy level sufficient to cause partial curing of the sealing material 4158 to form the film or layer 4160.

Figure 36D:
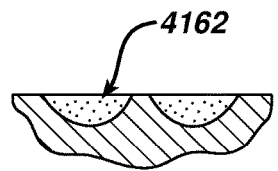
FIG. 36D is a cross-sectional view of the staple forming opening of FIG. 36A after complete curing.
Figure 37:
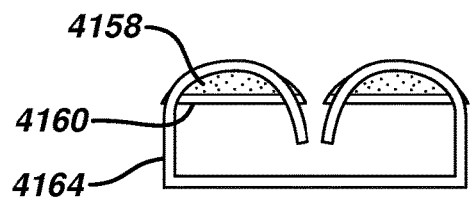
FIG. 37 is a side view of a surgical staple coupled to the adjunct of FIG. 35.

In some embodiments, the staple forming openings of an anvil can contain completely cured sealing material 4162, as shown in FIG. 36D. Fully cured sealing material 4162 can have different materials properties than the partially cured material shown in FIG. 35A. FIG. 37 shows a staple 4164 that was shaped using a surgical stapler with partially cured sealing material in the staple forming openings of the stapler anvil. The staple 4164 has legs that pass through the cured layer 4160, into the uncured sealing material 4158, and back through the cured layer 4160, and in some embodiments, the end of each leg of the staple 4164 can end in tissue. The sealing material helps to prevent any passage of fluids through tissue, adjacent to the staple, as well as preventing undesirable deformation or damage to the tissue.

Figure 38:
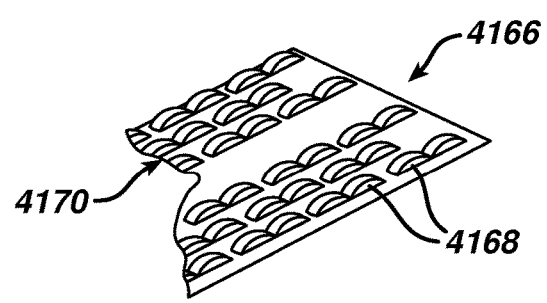
FIG. 38 is a perspective view of one embodiment of a film connecting a plurality of adjuncts.

FIG. 38 shows an alternate way of delivering adjuncts for the anvil-side of surgical staples 4166 that includes multiple adjuncts 4168 that fit into staple forming openings on the anvil of a surgical stapler and a thin connecting film 4170. The thin connecting film 4170 can be a continuous film that allows for easy transport and placement of multiple adjuncts 4168 at once.

Figure 39:
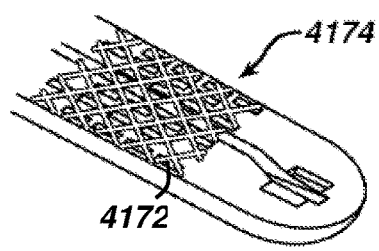
FIG. 39 is a perspective view of one embodiment of a weave connecting a plurality of adjuncts.
Figure 40:
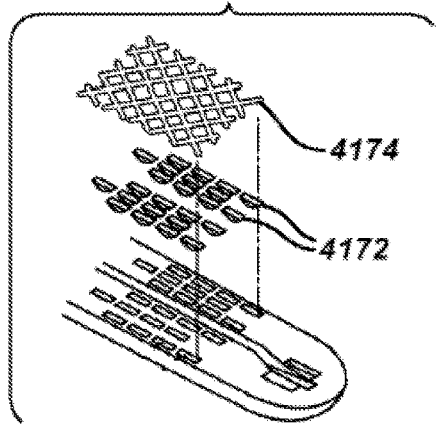
FIG. 40 is an exploded view of the weave and adjuncts of FIG. 39.
Figure 41A:
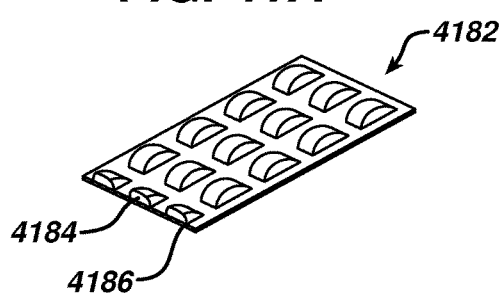
FIG. 41A is a perspective view of one embodiment of a plurality of adjuncts coupled to one another by a film of cured adjunct material.
Figure 41B:
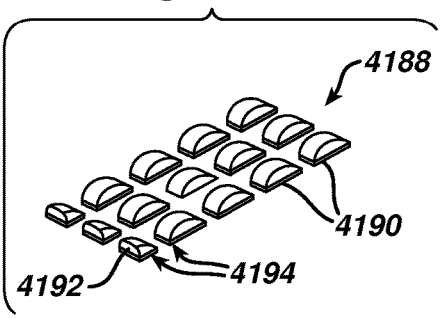
FIG. 41B is a perspective view of an alternative embodiment of a plurality of adjuncts separated from one another and including a layer of cured adjunct material.

FIG. 39 is a perspective view of showing adjuncts 4172 with 4174 mesh material. FIG. 40 shows an exploded view of the view of FIG. 39. FIGS. 41A and 41B show adjuncts 4184 that are cured with a film above the adjuncts 4186, in which the film connects the adjuncts 4186, as well as discrete adjuncts which are not connected 4190 to each other. In the system of discrete adjuncts 4188, each adjunct 4190 has un-cured seal material that fits the within the staple forming openings of the anvil of a surgical stapler. Each adjunct also has a layer of cured material 4194 above the uncured sealing material 4192.

Figure 42:
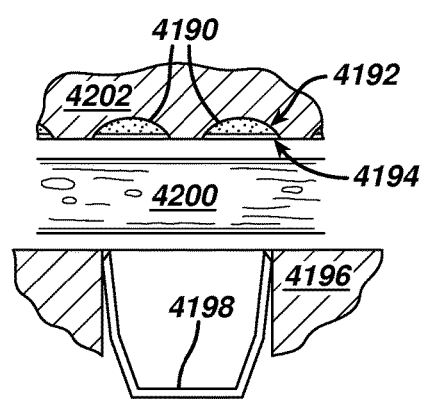
FIG. 42 is a cross-sectional view of one embodiment of a staple in a staple cartridge, tissue, and an adjunct disposed in a staple forming opening of an anvil.

FIG. 42 shows a cross-sectional view of a surgical staple 4198 in a cartridge 4196 that is opposite the anvil 4202 of a surgical stapler. In the figure, tissue 4200 is between the cartridge 4196 and the anvil 4202. The anvil 4202 is shown to have multiple staple forming openings 4190, each opening filled with uncured sealing material 4192 and having a layer of cured sealing material 4194 over each staple forming opening 4190.

Figure 43:
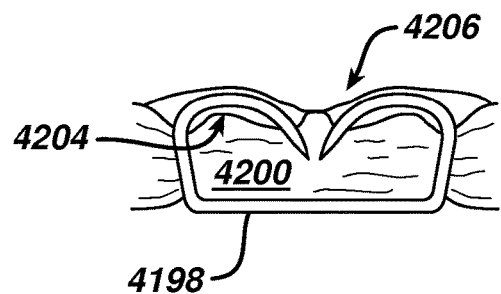
FIG. 43 is a cross-sectional view of a staple and the adjunct of FIG. 35 disposed in tissue.
Figure 44:
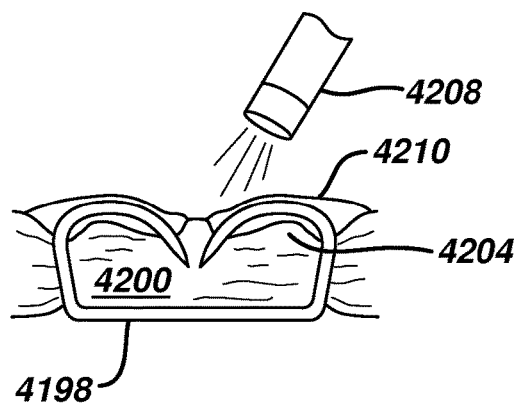
FIG. 44 is a cross-sectional view of the staple and adjunct of FIG. 43 being cured after implantation in tissue.

FIG. 43 is a cross-section view of a surgical staple 4198 inserted in tissue 4200 with an adjunct that includes both cured and uncured sealing material present on the free-ends of the legs of the staple. The legs of the staple have passed through the tissue, through a cured portion of the adjunct material 4204, through a portion of un-cured adjunct material 4206 and then back into the tissue 4200. FIG. 44 shows curing of the un-cured adjunct material 4206 in FIG. 43 so that it becomes a cured, conforming material 4210. A light source 4208 provides the appropriate radiation to cure the liquid or gel setting material 4206 after the material has spread to conform to the surface of the tissue 4200.

Figure 45:
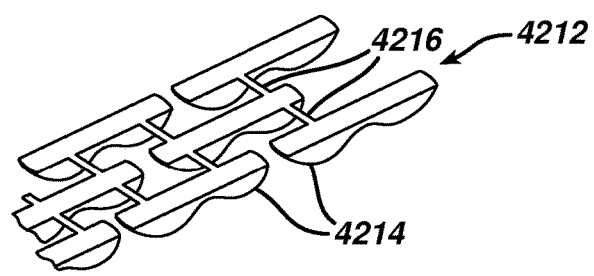
FIG. 45 is a perspective view of one embodiment of a plurality of adjuncts coupled by a plurality of connecting branches of adjunct material.
Figure 46:
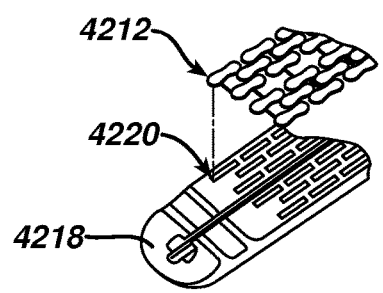
FIG. 46 is an exploded view of the plurality of adjuncts of FIG. 45 disposed in a plurality of staple forming openings of a surgical stapler anvil.

FIG. 45 shows a grouping 4212 of discrete adjunct segments 4214 that are joined by a plurality of connecting branches of adjunct material 4216. The adjunct segments 4214 in the grouping 4212 can be partially or fully cured, such that the grouping 4212 can be stored for long periods of time. FIG. 46 shows the adjunct grouping 4212 of FIG. 45 fitting over staple forming openings, or anvil pockets, 4220 on a surgical stapler anvil 4218.

Figure 47:
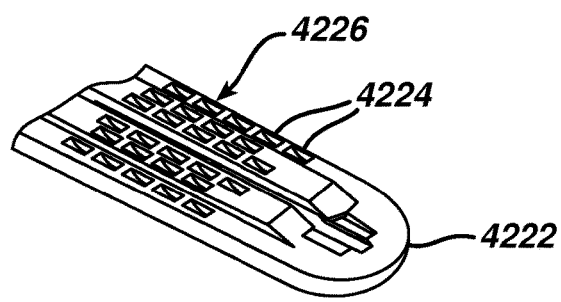
FIG. 47 is a perspective view of one embodiment of a surgical stapler anvil having features to destroy connecting branches extending between a plurality of adjuncts.
Figure 48:
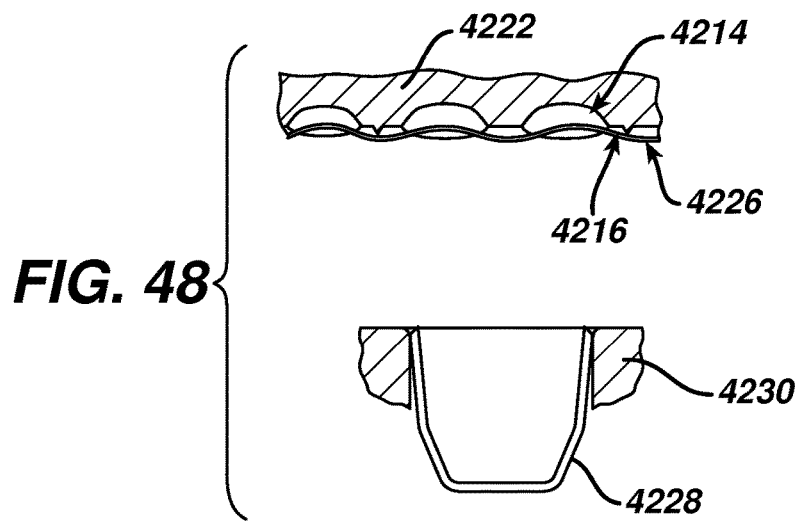
FIG. 48 is a cross-sectional view of one embodiment of a surgical stapler including a staple disposed in a staple cartridge and a plurality of adjuncts coupled to the anvil of FIG. 47.
Figure 49:
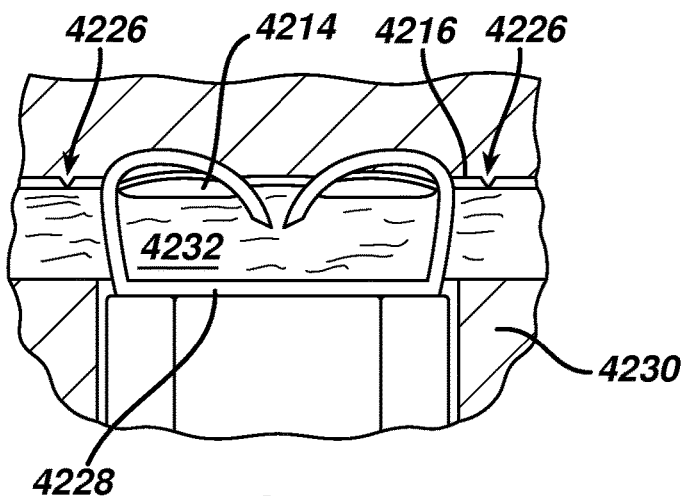
FIG. 49 is a cross-sectional view of the stapler of FIG. 48 ejecting a staple through tissue and into a staple forming opening of the anvil.
Figure 50:
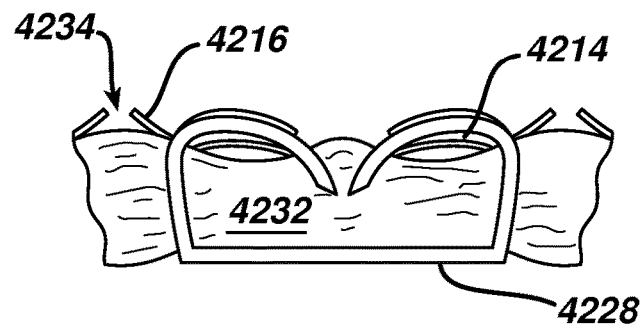
FIG. 50 is a cross-sectional view of the staple of FIG. 48 implanted in tissue.

FIG. 47 shows an anvil 4222 with adjunct-separating features 4226 between the staple forming openings 4224. FIG. 48 shows a side view of an embodiment of a surgical stapler that includes a staple 4228 in a staple cartridge 4230 and a plurality of adjunct segments 4214 coupled to the anvil 4222. The plurality of adjunct segments 4214 are joined by branches 4226. The branches 4226 are severed by the sharp features 4216 when the staple 4228 is inserted into the tissue (4232 in FIG. 49). FIG. 49 shows the staple 4228 as it is formed by actuation of the surgical staple, and FIG. 50 show the staple 4228 after it is fully implanted in the tissue 4232, with the branches 4226 severed, making breaks 4234 in the branches, and with the adjunct segments 4214 between a portion of the ends of the legs of the staple 4228 and the tissue 4232.

FIG. 51 is a cross-sectional view of an embodiment of a retainer 4238 to hold adjunct material 4240 in place against a surgical stapler anvil 4236. FIG. 52A is a cross-sectional view of the retainer 4238 and anvil 4236 shown in FIG. 51, with adjunct material 4240 between the anvil and the retainer. FIG. 52B is a variation of the embodiment shown in FIG. 52A in which the adjunct material is present only as discrete adjuncts 4240, without any connecting material.

Figure 53:
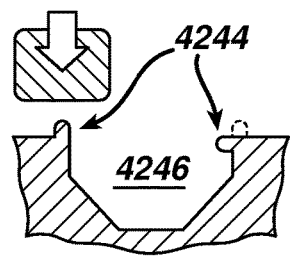
FIG. 53 is a cross-sectional view of one embodiment of a staple forming opening having a retainer formed thereon.
Figure 54:
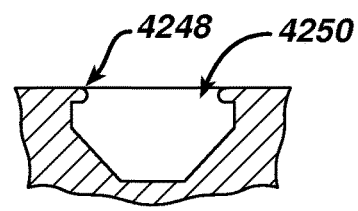
FIG. 54 is a cross-sectional view of the staple forming opening of FIG. 53 holding adjunct material therein.
Figure 55:
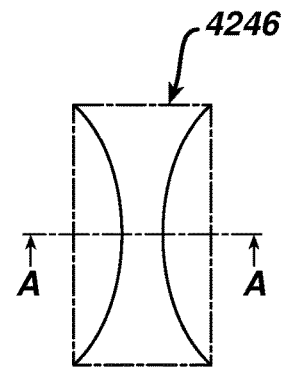
FIG. 55 is a top view of the staple forming opening of FIG. 53.

FIG. 53 is a cross-sectional view of an embodiment of a staple forming opening 4246 with bulge tabs 4244. The tabs 4244 are shaped during manufacturing into retainer features. FIG. 54 shows the staple forming opening 4246 of FIG. 53 filled with a plug element 4250, or adjunct material, and the bulge tabs 4244 shaped into trapping features 4248. FIG. 55 is a top view of the staple forming opening 4246 shown in FIG. 53. The line A-A is that along which the cross-sectional views are taken.

Figure 56:
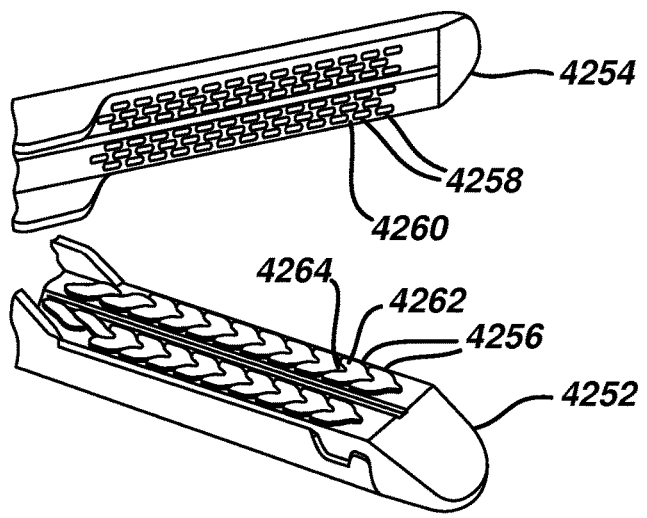
FIG. 56 is a perspective view of one embodiment of a surgical stapler anvil and staple cartridge having adjunct segments coupled thereto.

FIG. 56 shows a perspective view of one embodiment of a surgical stapler with adjunct segments 4256, 4258 associated with both the anvil 4254 and staple cartridge 4252. In this embodiment, the adjunct segments 4258 on the anvil 4254 have branches of adjunct material or filaments 4260 between the adjunct segments 4258. The adjunct segments 4256 on the staple cartridge 4252 interlock with each other, such that a notch 4262 in one adjunct segment receives a protrusion 4264 from its neighboring adjunct segment. In this way, additional means of holding together the adjuncts 4256 on the staple cartridge 4252, which is on the crown-side of the staples, are needed. Further, the adjuncts 4256 on the staple cartridge 4252 span more than one staple, so that two or more staples will be connected by each adjunct.

Figure 57:
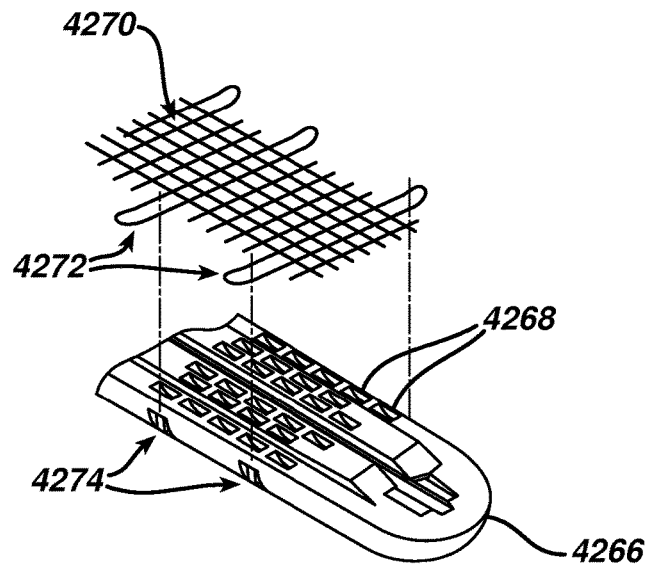
FIG. 57 is an exploded view of one embodiment of attachment and alignment features of a surgical stapler anvil.
Figure 58:
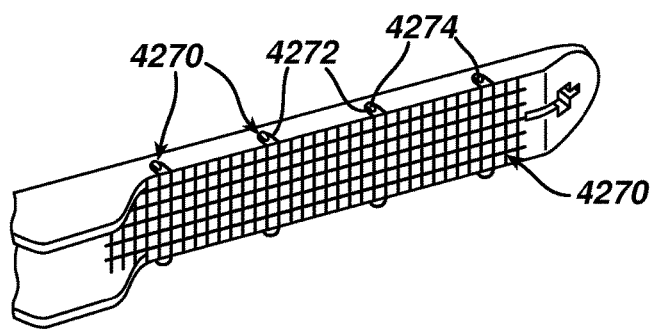
FIG. 58 is a perspective view of the anvil of FIG. 57.

FIGS. 57 and 58 show an embodiment of a surgical stapler with an anvil 4266 that includes attachment 4272 and alignment features 4274 for adjunct material 4270. FIG. 57 is an exploded view of the anvil 4266 with staple forming openings 4268 and features 4274 on the side of the anvil for anchoring or interfacing with loops 4272 on a sheet of adjunct material 4270. FIG. 58 shows the adjunct material 4270 flush against the anvil 4266 with the loops 4272 attached to the features 4274 which are shown to be tabs or pegs that attach to the loops. Such features 4274 can be present on a staple cartridge and used with a similar type of adjunct material instead of or in addition to being used on the anvil 4266 of a surgical stapler.

Figure 59:
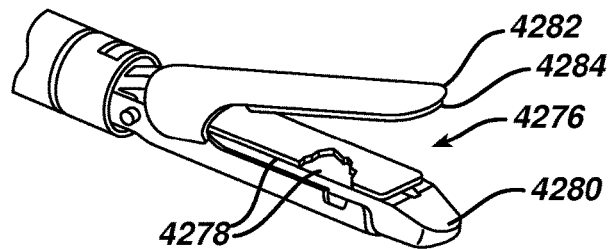
FIG. 59 is a perspective view of one embodiment of a surgical stapler having a plurality of adjunct segments coupled thereto and connected to one another by a film.
Figure 60:
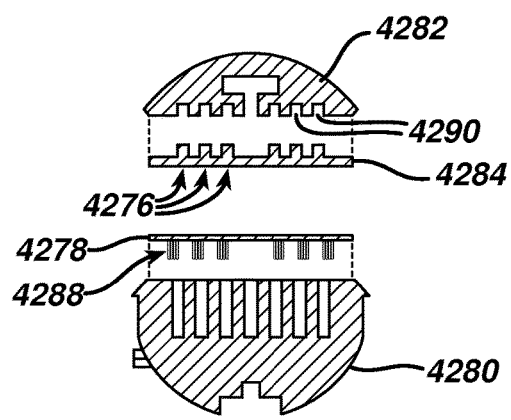
FIG. 60 is an exploded cross-sectional view of the surgical stapler of FIG. 59.

FIGS. 59-61 show an embodiment of a surgical stapler 4276 with adjunct assemblies 4284, 4278 coupled to both the anvil 4282 and the staple cartridge 4280 of the stapler. The adjunct assemblies 4284, 4278 are shown to include adjunct segments 4286, 4288 that are joined by a sheet of adjunct material. On the anvil 4282, there are a plurality of staple forming openings 4290 which can accept adjunct segments 4286. FIG. 61 shows the relative thickness of an adjunct segment 4286 to that of the sheet of adjunct material. The adjunct segments 4286 on the stapler anvil 4282 can include partially cured or fully cured sealing material, as described above. The adjunct material 4278 for use with the staple cartridge 4280 has adjunct segments 4288 which can fit over the ends of the staples in the cartridge 4280, either in contact with or above the staple legs. In practice, using such a surgical stapler 4276 would insert staples into tissue in with adjunct material both at the crown of each staple and at the anvil-side of each staple, thus potentially reducing leaking and tissue damage caused by the staple.

FIG. 62 shows a cross-sectional view of one embodiment of a plurality of adjunct segments 4288 (e.g., micro-fingers) connected to one another by a film 4278. These adjunct segments 4288 may not correspond to individual features on a stapler anvil or a staple cartridge, but instead may serve to act as a cushion or a light-weight, highly conformable and compressible material. FIGS. 63A and 63B show cross-sectional views of a surgical stapler, similar to that shown in FIG. 59, with a staple 4294 in a cartridge 4292 with an adjunct material 4296 that includes a plurality of adjunct segments 4292 that can act as a light-weight, conformable and compressible material 4296. The anvil 4300 shown in FIG. 63A has staple forming openings 4302 in which include adjunct segments 4304 that are attached to a sheet of adjunct material 4306. FIG. 63B shows the staple 4294 after the stapler has been actuated on tissue 4308. The tissue 4308 contacts adjunct material with micro-fingers 4298 near the crown of the staple and thicker, continuous adjunct material 4304 at the anvil-side of the staple.

Figure 64A:
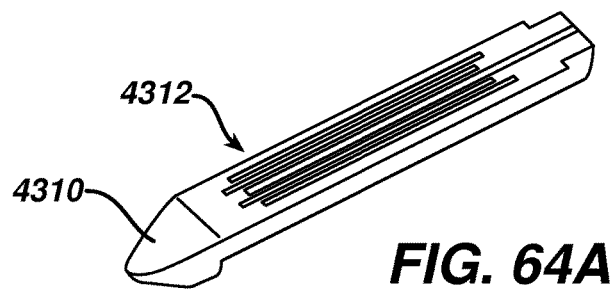
FIG. 64A is a perspective view of one embodiment of a surgical stapler having a plurality of adjunct segments of differing thicknesses.
Figure 64B:
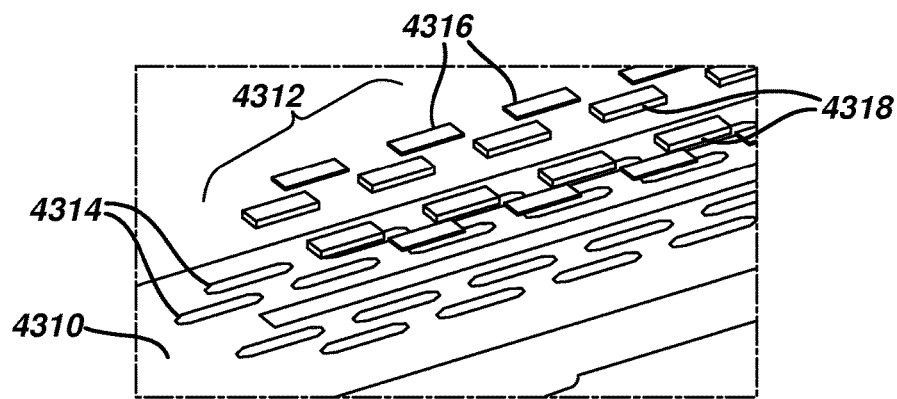
FIG. 64B is a close exploded view of the surgical stapler of FIG. 64A.

FIGS. 64A and 64B show an embodiment of a surgical stapler component 4310 that includes adjunct segments of varying thickness 4312. Each adjunct segment is discrete and spans only one staple. FIG. 64B shows that adjunct segments of greater thickness 4318 are located nearest the centerline of the stapler component 4310, and that the thinner adjunct segments 4316 correspond to staples further away from the centerline, where a cut in stapled tissue would be made.

Figure 65:
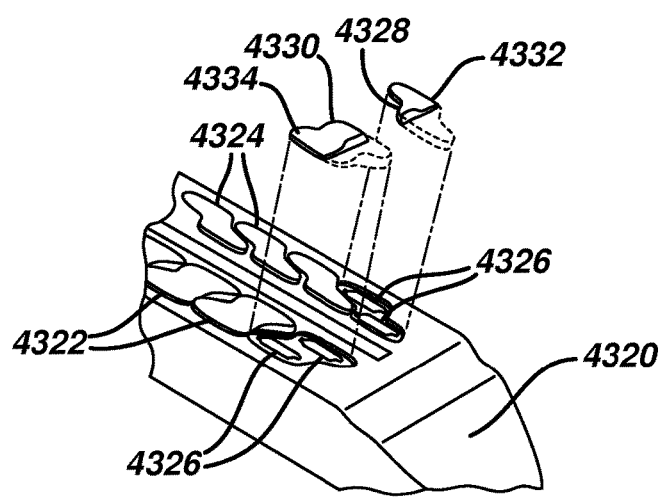
FIG. 65 is an exploded perspective view of an alternative embodiment of a surgical stapler having a plurality of adjunct segments of differing thicknesses.

FIG. 65 shows another embodiment of adjunct segments 4322, 4326 on one part of a surgical stapler. The adjunct segments 4322, 4324 are not of uniform thickness. Each adjunct segment has a thick side, 4328, 4330, and a thin side 4332, 4334. Each adjunct segment 4322, 4324 spans more than one staple 4326 location shown in the exemplary staple cartridge 4320. The adjunct segments are shown with their thick sides 4328, 4330 towards the center of the staple cartridge 4320. When the surgical stapler cuts through tissue after stapling the tissue, it will cut the tissue through the center of the cartridge, between the thick sides 4328, 4330 of the adjunct segments. In this way, the adjunct segments 4322, 4324 provide more support to the staples nearest the free ends of the tissue.

Figure 66:
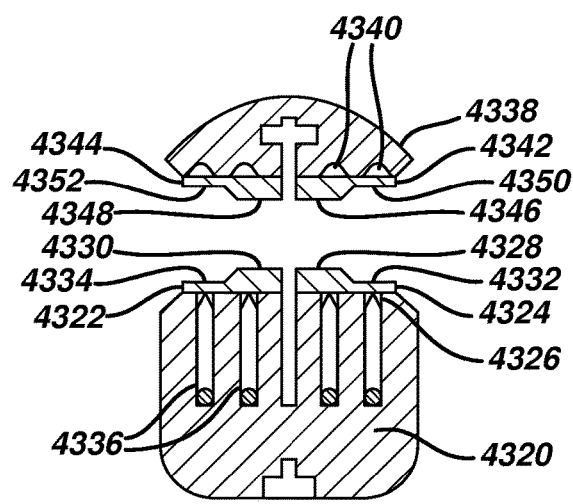
FIG. 66 is a cross-sectional view of the surgical stapler of FIG. 65.

FIG. 66 shows a cross-sectional view of the stapler of FIG. 65. The staple cartridge 4320 holds staples 4336. Over the staples 4336 are adjunct segments 4334 and 4324 which have their thick sides 4330, 4328 near the center of the cartridge and their thin sides 4324, 4322 toward the outer edges of the cartridge 4320, over the outermost staples. The stapler anvil 4338 has staple forming openings 4340, over which are adjunct segments 4342, 4344. The anvil-side adjunct segments 4342, 4344, are shown to have their thick sides 4346, 4348 near the venter of the anvil, corresponding to the innermost staples. The thin sides 4350, 4352 of the anvil-side adjuncts 4342, 4344 are located toward the edges of the anvil such that the thin sides are associated with the outermost staples once the stapler is actuated.

Figure 67:
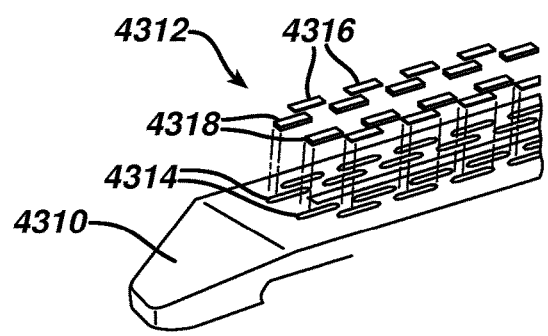
FIG. 67 is a perspective view of an alternative embodiment of a surgical stapler having a plurality of adjunct segments of differing thicknesses.

FIG. 67 shows an embodiment of a surgical stapler component 4310 that includes adjunct segments of varying thickness 4312. Each adjunct segment is discrete and spans only one staple. Adjunct segments of greater thickness 4318 are located nearest the centerline of the stapler component 4310, and that the thinner adjunct segments 4316 correspond to staples further away from the centerline, where a cut in stapled tissue would be made. These adjunct segments are discrete, not interlocking as those shown in FIG. 65.

FIGS. 68A and 68B show a multi-material adjunct 4354 that includes a film 4356 with openings 4360 and a base layer 4358 with connecting features 4362. The base layer 4358 can be a layer of elastomeric material. The connecting features 4362 can be shaped to fit through the openings 4360, for example the connecting features 4362 shown are columns and the openings 4360 are circular holes. The connecting features 4362 and openings 4360 can be any suitable shape, symmetrical or asymmetrical, as in when a particular orientation between the base layer 4358 and the film 4356 is desired. FIGS. 69A and 69B show the adjunct of FIGS. 68A and 68B in context, with a staple 4364 shown. FIG. 69A shows the staple prior to insertion into the adjunct 4354. The staple 4364 is shown as aligned with the connecting features 4362 so that each leg of the staple moves through a connecting feature 4362 when stapling tissue. FIG. 69B shows the staple 4364 after being moved toward an anvil of a surgical stapler.

Figure 70:
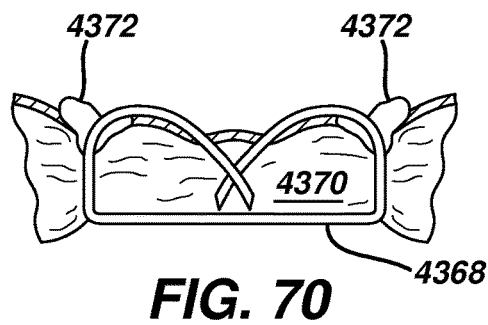
FIG. 70 is a cross-sectional view of one embodiment of a surgical staple and adjunct formed in tissue.
Figure 71:
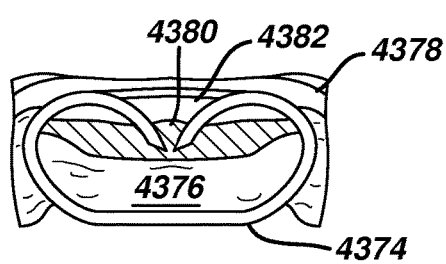
FIG. 71 is a cross-sectional view of an alternative embodiment of a surgical staple and adjunct formed in tissue.
Figure 72:
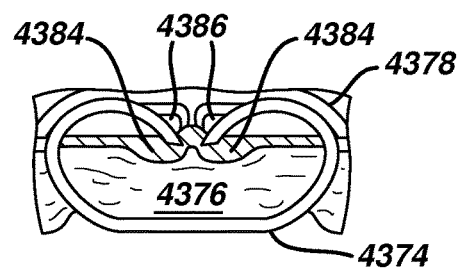
FIG. 72 is a cross-sectional view of still another embodiment of a surgical staple and adjunct formed in tissue.

FIGS. 70-72 show different embodiments of a surgical staple and adjunct in tissue, with the legs of the surgical staple shaped to retain the tissue in a particular configuration. FIG. 70 shows a staple 4368 in tissue 4370 with adjunct material 4372 near the anvil-side of the staple, such that the adjunct material 4372 acts as a seal to avoid leaking from the tissue 4370. FIG. 71 shows a staple 4374 in tissue 4376 with an adjunct on the anvil-side of the staple 4374. The adjunct includes a film 4378, a depression in the film 4382, and a thicker area in the adjunct 4380 into which the ends of the legs of the staple 4374 move when the staple forms. In FIG. 72, the staple 4374 is used with an adjunct with a film 4378, multiple depressions in the film per staple 4386, and a pair of thicker areas in the adjunct 4380 into which the ends of the legs of the staple 4374 move when the staple forms, one pair of thicker areas per staple.

Figure 73A:
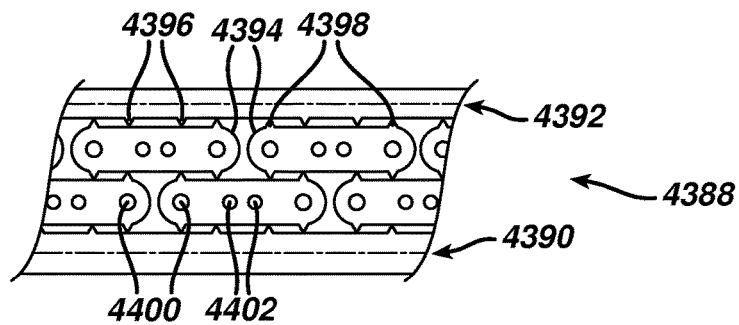
FIG. 73A is a top view of one embodiment of a plurality of adjuncts coupled to a surgical stapler anvil.
Figure 73B:
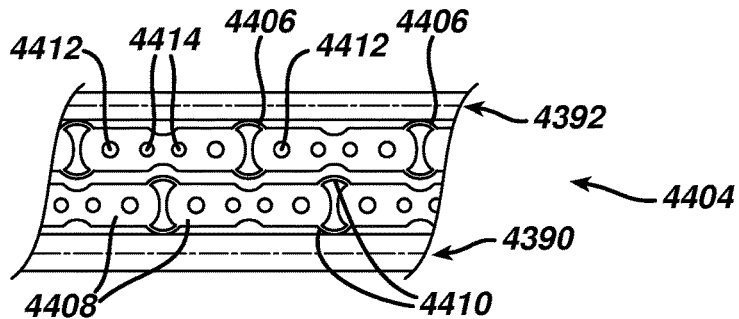
FIG. 73B is a top view of an alternative embodiment of a plurality of adjuncts coupled to a surgical stapler anvil.
Figure 73C:
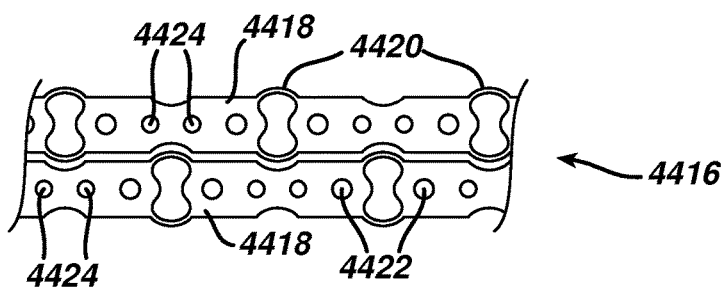
FIG. 73C is a top view of still another embodiment of a plurality of adjuncts coupled to a surgical stapler anvil.
Figure 73D:
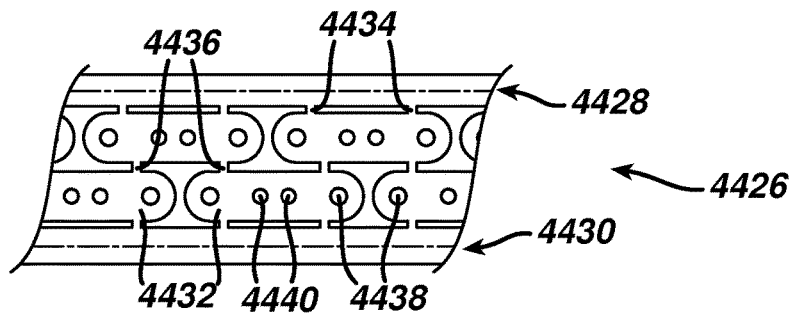
FIG. 73D is a top view of yet another embodiment of a plurality of adjuncts coupled to a surgical stapler anvil.
Figure 73E:
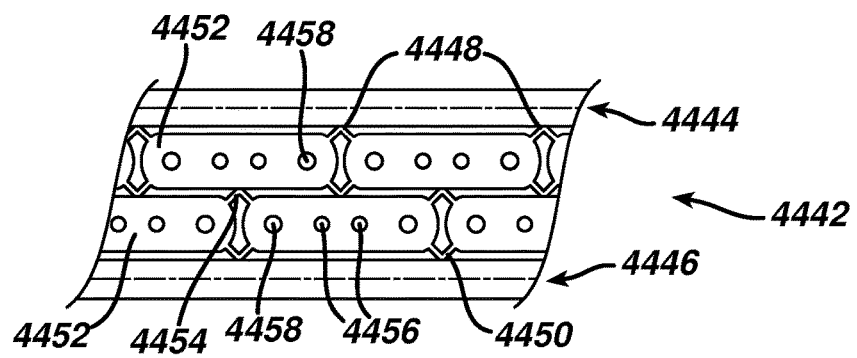
FIG. 73E is a top view of still another embodiment of a plurality of adjuncts coupled to a surgical stapler anvil.

FIGS. 73A-73E show different embodiments for a plurality of adjuncts coupled to a surgical stapler anvil. The adjunct array 4388 shown in FIG. 73A includes portions near the anvil edge 4392, portions near the anvil centerline 4390, and multiple adjunct segments 4394. The adjunct segments shown include openings 4400 for staple legs to pass through as they move toward the anvil and openings 4402 for staple legs to pass through as they move away from the anvil during staple forming. The adjunct segments 4394 connect to each other and to the portions of the adjunct array near the anvil edge 4392 and anvil centerline 4390 through branches of adjunct material 4398. The edge 4392 and centerline 4390 portions also have branches 4396 to connect to the adjunct segments 4394. FIG. 73B shows an adjunct assembly 4404 that is similar to that shown in FIG. 73A. The adjunct array 4404 shown in FIG. 73B includes portions near the anvil edge 4392, portions near the anvil centerline 4390, and multiple adjunct segments 4408. The adjunct segments shown include openings 4412 for staple legs to pass through as they move toward the anvil and openings 4414 for staple legs to pass through as they move away from the anvil during staple forming. The adjunct segments 4408 connect to each other and to the portions of the adjunct array near the anvil edge 4392 and anvil centerline 4390 through branches of adjunct material 4406. Unlike the adjunct array 4388 in FIG. 73A, the adjunct array 4404 has no connectors between rows of adjunct segments. The adjunct array 4416 of FIG. 73C is similar to that of FIG. 73B, in that there are no connectors between the rows of adjunct segments, only connectors 4420 between each adjunct segment 4418 and its neighboring segment. Each segment has openings 4422 for staple legs to pass through as they move toward the anvil and openings 4424 for staple legs to pass through as they move away from the anvil during staple forming. The adjunct array 4426 shown in FIG. 73D includes portions near the anvil edge 4428, portions near the anvil centerline 4430, and multiple adjunct segments 4432. The adjunct segments shown include openings 4438 for staple legs to pass through as they move toward the anvil and openings 4440 for staple legs to pass through as they move away from the anvil during staple forming. The adjunct segments 4432 connect to each other and to the portions of the adjunct array near the anvil edge 4428 and anvil centerline 4430 through branches of adjunct material 4434, 4436. The adjunct array 4442 shown in FIG. 73E is different from that shown in FIG. 73D and includes portions near the anvil edge 4444, portions near the anvil centerline 4446, and multiple adjunct segments 4452. The adjunct segments shown include openings 4458 for staple legs to pass through as they move toward the anvil and openings 4456 for staple legs to pass through as they move away from the anvil during staple forming. The adjunct segments 4452 connect to each other and to the portions of the adjunct array near the anvil edge 4444 and anvil centerline 4446 through branches of adjunct material 4448, 4454, 4450.

Figure 74:
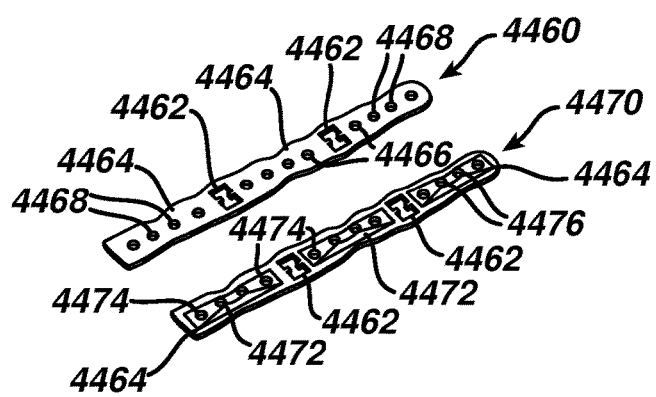
FIG. 74 is a perspective view of one embodiment of a plurality of adjuncts.

FIG. 74 shows a first side 4460 and a second side 4470 of a plurality of adjuncts 4464 that are connected in a row. The first side view 4460 show the adjunct segments 4464, their connectors 4462, the openings 4466 in the adjunct segments for when the legs move towards the stapler anvil during staple forming, and the openings 4468 in the adjunct segments for when the legs move away from the stapler anvil during staple forming. The second side view 4470 shows elements of the first side view 4460, but there is additional material on this side of the adjuncts 4464. Through this additional material, there are openings 4474 in the adjunct segments for when the legs move towards the stapler anvil during staple forming, and the openings 4472 in the adjunct segments for when the legs move away from the stapler anvil during staple forming.

Figure 75:
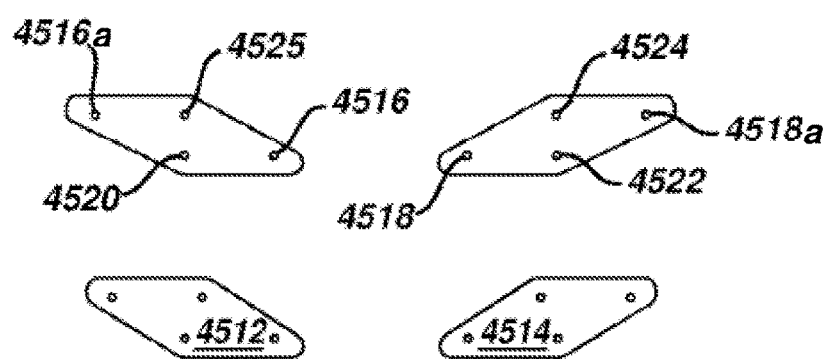
FIG. 75 is a top view of one embodiment of adjunct segment shapes.
Figure 76:
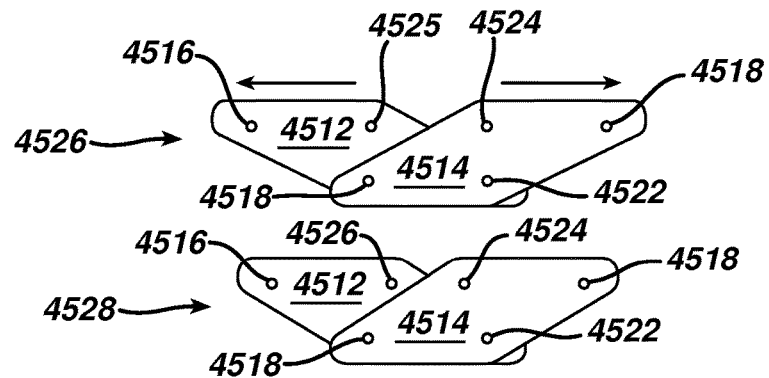
FIG. 76 is a top view of the adjuncts of FIG. 75 coupled to one another.
Figure 77:
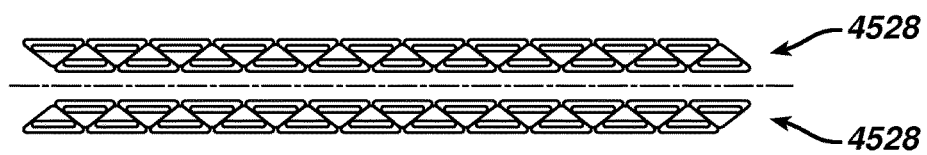
FIG. 77 is a top view of one embodiment of a sheet of adjunct segments coupled to one another.
Figure 78:
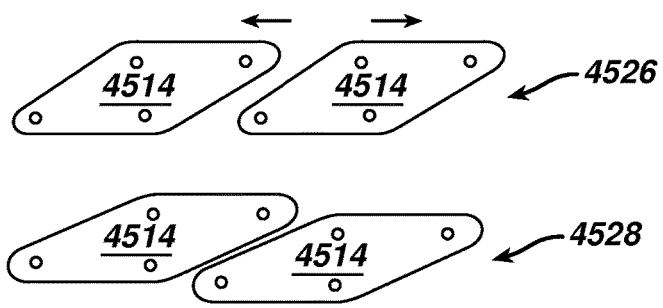
FIG. 78 is a top view of an alternative embodiment of adjunct segment shapes.
Figure 79:
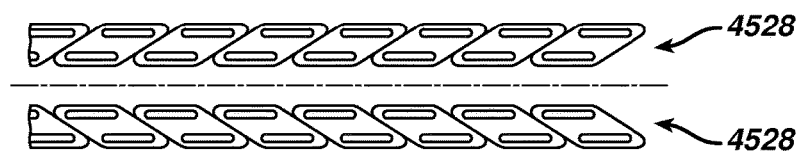
FIG. 79 is a top view of the adjuncts of FIG. 78 coupled to one another.

FIGS. 75-79 show embodiments of adjuncts segments that overlap and interlock to some degree when in use with surgical staples. The configurations shown can be used to accommodate for movement in the tissue, such as expansion on contraction after stapling. In FIG. 75, there are two configurations of adjunct segments, 4512, 4514. The adjunct segments shown 4512, 4514 are mirror images of each other. Each adjunct segment spans two staples. For example, as in FIG. 77, each adjunct segment is shown with two staple crowns in contact with each segment. However, it should be noted that in the configuration shown in FIGS. 76 and 77 each staple, aside from the staples at the end of the row, contacts two overlapping adjunct segments. In FIG. 76, the two adjunct segments 4512 and 4514 are seen in an extended configuration 4526 and in a compact configuration 4528. Openings are shown in the adjunct segments through which staple legs pass as staples are formed by moving from the staple cartridge toward the anvil in a surgical stapler. As can be seen, when the adjunct 4512, 4514 are overlaid, some of the openings overlap and align to allow a staple leg to pass through. Opening 4516 aligns with opening 4522, and opening 4520 aligns with opening 4518 at the bottoms of the adjunct segments. Opening 4518*a* is shown as not aligning with any other opening, but opening 4518*a* may align with opening 4525 of another adjunct segment that is similar to 4512. Similarly, opening 4524 is not shown aligning with any other opening, but it may align with opening 4516*a* of another adjunct segment that is similar to 4512. FIG. 76 shows that in an extended configuration 4526, adjacent openings on the top portions of the adjunct segments, 4525 and 4524, are further apart than in a compact configuration 4528. FIG. 78 shows the relative position of two adjacent adjunct segments that are similarly oriented 4514. In an extended configuration 4526 there is a gap or space between the adjunct segments 4514. In a compact configuration 4528 the adjacent adjunct segments 4514 are very close, in some instance touching, and in some instances slightly overlapping. FIG. 79 shows a compact configuration 4528 in which only half of the adjunct segments are visible, such as when the adjunct segments are opaque and only the topmost adjunct segments are visible.

Figure 80A:
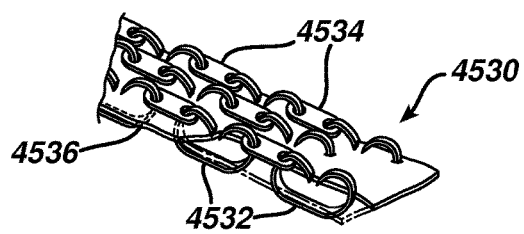
FIG. 80A is a perspective view of one embodiment of adjunct segments extending between adjacent surgical staples.
Figure 80B:
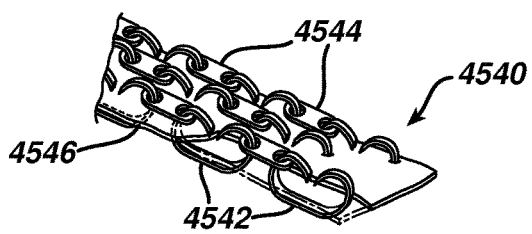
FIG. 80B is a perspective view of an alternative embodiment of adjunct segments extending between adjacent surgical staples.
Figure 80C:
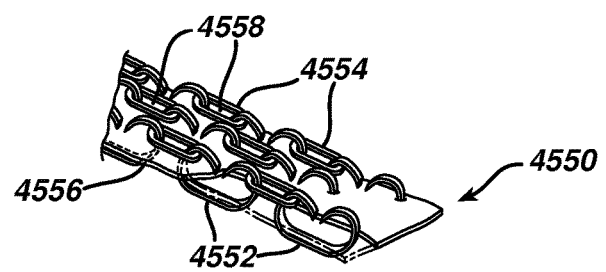
FIG. 80C is a perspective view of another embodiment of adjunct segments extending between adjacent surgical staples.

FIGS. 80A-80C show embodiments of adjunct segments that connect adjacent surgical staples. FIG. 80A shows rows 4530 of surgical staples 4532 that are connected the next staple in the row via an adjunct segment 4534. The adjunct segments 4534 are shown as being in or on a supporting layer or film 4536. Such configurations, adjunct segments with supporting layers or films, are described in greater detail herein elsewhere. The adjunct segments 4534 shown in FIG. 80A are located near the anvil-side of the staples once the staples are deployed in tissue. FIG. 80B shows row 4540 of surgical staples 4542 in use with adjunct segments 4544 and a supporting film 4546. As in FIG. 80A, the adjunct segments 4544 are located near anvil-side of the staples 4542. However the adjunct segments 4544 of FIG. 80B are shaped differently from those in FIG. 80A, in that the openings for accepting staple legs are larger in FIG. 80B. This increased size can allow for slight contraction or expansion of the tissue and the corresponding motion of the staples. FIG. 80C shows another embodiment in which rows 4550 of surgical staples 4552 with adjunct segments 4554 and a support film 4556 are used together. The adjunct segments 4554 in FIG. 80C are different from those in FIGS. 80A and 80B because the adjunct segments 4554 are rings, allowing the maximum amounts of motion of the staple legs within the center 4558 of the adjunct segments 4554. This allows even greater motion of the each surgical staple with regards to its neighbor, and thus the stapled tissue can accommodate greater expansion and contraction.

Figure 81:
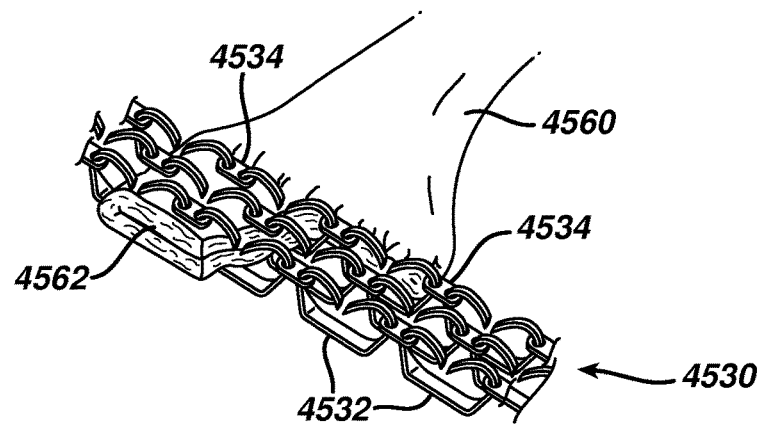
FIG. 81 is a perspective view of the adjuncts and surgical staples of FIG. 80A disposed in tissue.
Figure 82:
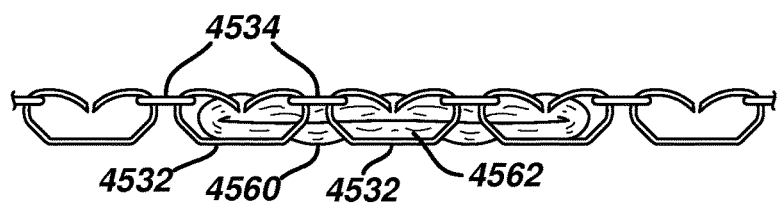
FIG. 82 is a cross-sectional view of the adjuncts and surgical staples of FIG. 81.

FIGS. 81 and 82 show the adjunct segments 4534 and surgical staples 4532 of FIG. 80A. In FIG. 81, an artery 4560 has staples 4532 and adjunct segments 4543 seal a portion of the artery 4562. FIG. 82 shows the artery 4560, staples 4532, and adjuncts 4534. In both FIGS. 81 and 82, each staple 4532 is shown connected to its neighbor through opposite ends of an adjunct segment.

Figure 83:
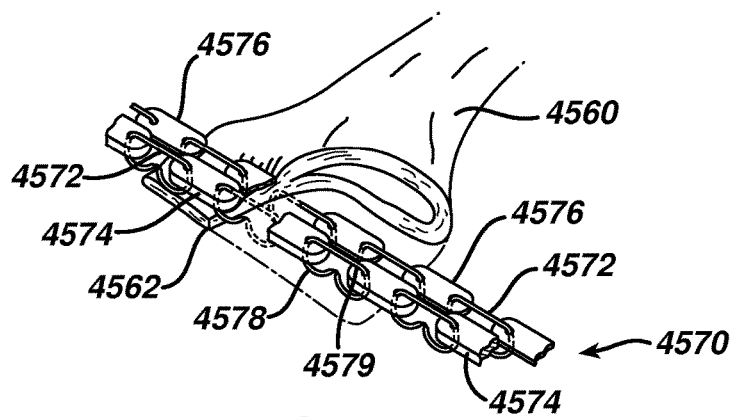
FIG. 83 is a perspective view of an alternative embodiment of surgical staples and adjuncts in tissue.
Figure 84:
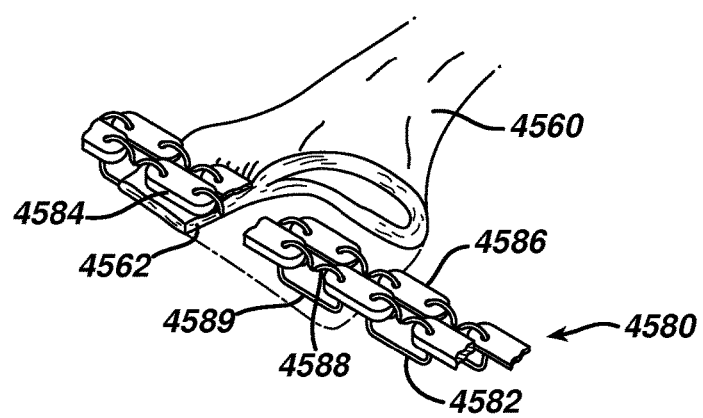
FIG. 84 is a perspective view of another embodiment of surgical staples and adjuncts in tissue.
Figure 85:
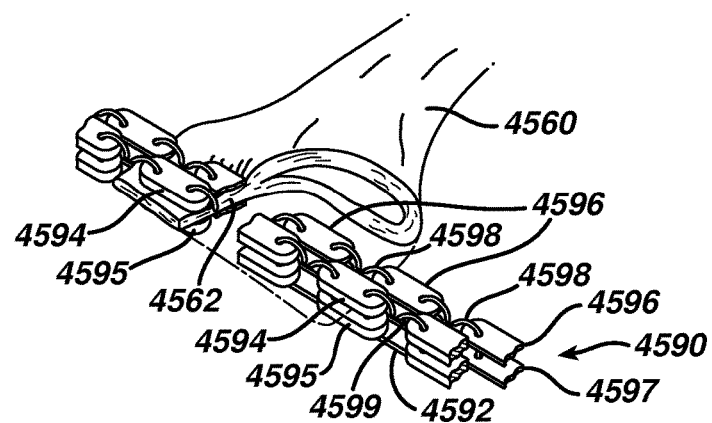
FIG. 85 is a perspective view of still another embodiment of surgical staples and adjuncts in tissue.

FIGS. 83-85 are similar to FIG. 81, except that each shows a different type or use of an adjunct segment. In FIG. 83, an artery or other type of tissue 4560 is sealed by two rows 4570 of staples 4572. The row of surgical staples 4572 at the free edge of the tissue 4562 has thick adjunct segments 4574. The row of surgical staples 4572 further away from the free edge of the tissue 4562 has thinner adjunct segments 4576. The adjunct segments 4574, 4576 connect each surgical staple 4572 to at least one neighboring staple. Also, the adjunct segments 4574, 4576 are near the crowns of the staples 4579 when the staples are deployed, as shown. Using different thickness adjunct segments 4574, 4576 can help to prevent tissue damage and can help to promote healing of the tissue 4560 after the stapling procedure. The embodiment of rows of staples 4580 shown in FIG. 84 is similar to that shown in FIG. 83, except that the adjunct segments 4584, 4586 are positioned near the anvil-side portions 4588 of the surgical staples 4582. The thickness of the adjunct segments 4584, 4586 are different, in that those adjunct segments nearest the free edge 4562 of the tissue are thicker adjunct segments 4584 and those away from are thinner 4586. FIG. 85 shows an embodiment of rows 4590 of surgical staples 4592 where thicker adjuncts 4594, 4595 are used closer to the free edge 4562 of the tissue 4560 and thinner adjuncts are used away from the free edge 4562 of the tissue 4560 to attach each staple 4592 to a neighboring staple along the length of the rows 4590. In the embodiment shown in FIG. 85, adjuncts 4594, 4595, 4596, 4597 are located near the crowns 4599 of the staples 4592, as well as near the anvil-side portions 4598 of the staples 4592.

Figure 86:
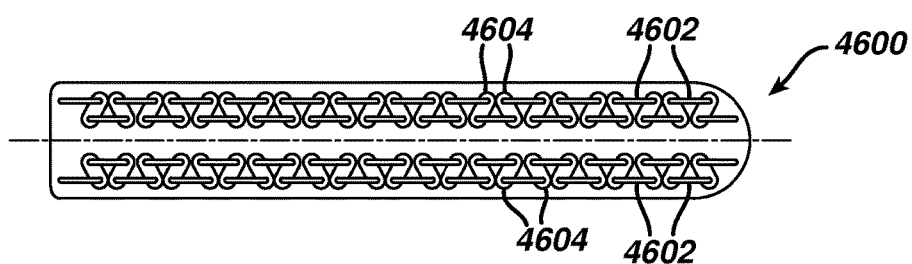
FIG. 86 is a top view of one embodiment of surgical staples and adjuncts extending between adjacent staples.
Figure 88A:
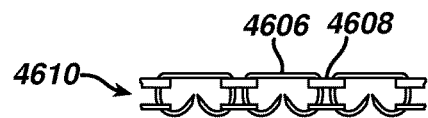
FIG. 88A is a side view of the surgical staples and adjuncts of FIG. 87 in a relaxed state.
Figure 88B:
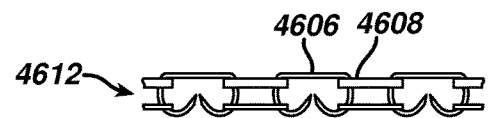
Figure 89:
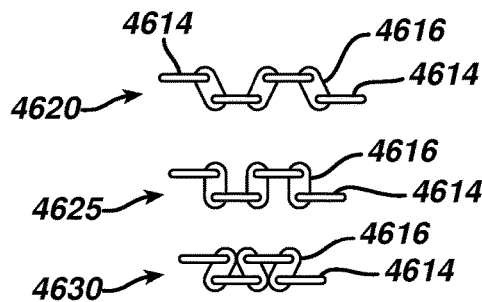

Staple lines that include a plurality of surgical staples and adjunct segments that connect two surgical staples together can exhibit a myriad of configurations that correspond to a range of contraction or expansion of the underlying tissue. FIGS. 86-89 show exemplary configurations adjunct segments and surgical staples in which each staple connects two adjunct segments. FIG. 86 shows a staple cartridge 4600 with adjunct segments 4604 that contact two staples 4602 when forming a staple line. The staple line includes two rows of staples that are applied parallel to the surgical cut, with the first row adjacent to a surgical cut and the second row further away from the surgical cut. The staples in the first row are offset from the second row. Each adjunct segment 4604 connects a staple from the first row with a staple from the second row. Because of the offset, the adjunct segments 4606 are applied in a position that is tilted when compared to a line perpendicular to the surgical cut, and in a relaxed state, as shown, the adjunct segments 4616 are as close together as they can be, touching or nearly touching. FIG. 89 shows the progression of the configuration changes from a tensioned state 4620 to a fully relaxed state 4630. In an extremely tensioned state 4620, the adjunct segments 4616 are at an angle in the range of about 0° to 90° in a position that so that the adjunct segments 4616 are further away from each other than in the relaxed state 4630. In the intermediate state 4625 shown in FIG. 89, the adjunct segments 4616 are perpendicular to the surgical cut. The relaxed state 4630 is similar to that shown in FIG. 86.

Figure 87:
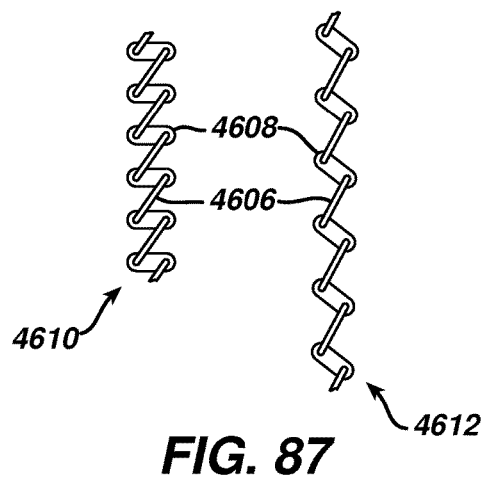
FIG. 87 is a top view of an alternative embodiment of surgical staples and adjuncts extending between adjacent staples.

FIG. 87 shows another configuration of adjunct segments 4608 and surgical staples 4606 in which the staples are applied along a surgical cut at an angle. In a relaxed state 4610, such as when first applied to tissue, the staples 4606 are between about 0° and 90° to the cut, such as at about 45° to the cut, and the adjunct segments 4608 are perpendicular to the cut. When the tissue stretches, the staples 4606 are at a different angle, such as about 30° from the cut. The adjunct segments 4608 move from a position substantially perpendicular to the surgical cut to one that is no longer perpendicular. FIG. 88A shows a side view of the relaxed configuration 4610, and FIG. 88B shows a side view of the tensioned configuration 4612 of staples 4606 and adjunct segments 4608.

Figure 90A:
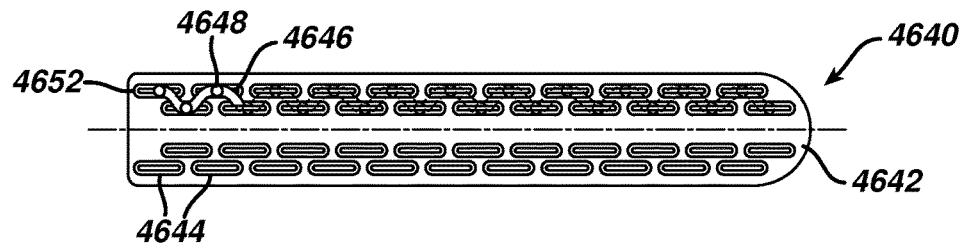
Figure 90B:

FIGS. 90A-90B show an embodiment 4640 of surgical staples and adjunct segments 4652 connected by a serpentine connector 4646 on an optional support layer 4642. The support layer 4642 can also include adjunct segments 4644 that are not connected. The serpentine connector 4646 is connected to the adjunct segments 4652 at connection points 4648. The support and adjunct segments 4652 shown include openings for staple legs.

Figure 91A:
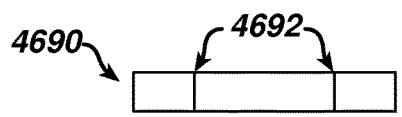
Figure 91B:
Figure 91C:
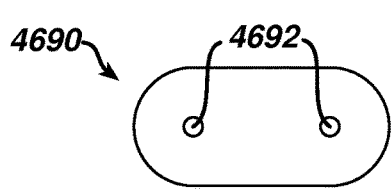
Figure 91D:
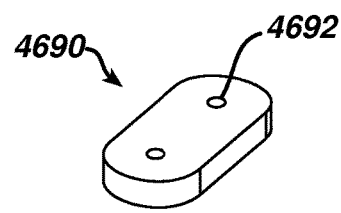
Figure 92A:
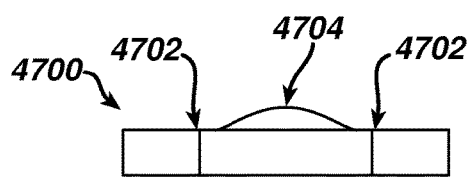
Figure 92B:
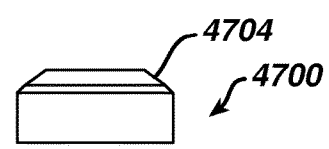
Figure 92C:
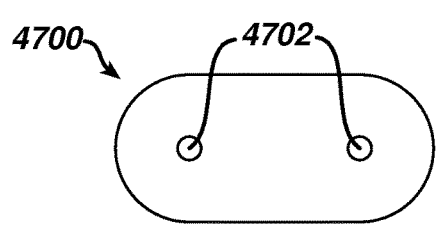
Figure 92D:
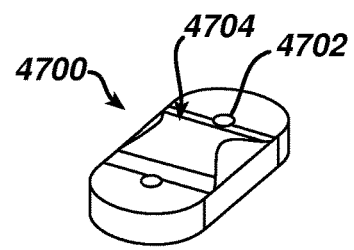

As shown in other figures described above, adjunct segments can have many configurations. FIGS. 91A-95D show four different configurations. FIGS. 91A-91D show an adjunct segment 4690 that is symmetric, such that the top view and the bottom view are similar. The adjunct segment 4690 includes openings 4692 for staple legs. FIG. 91A is a cross-sectional view of the adjunct segment 4690, FIG. 91B is an end view of the adjunct segment, FIG. 91C is a bottom view of the adjunct segment 4690, and FIG. 91D is a top perspective view of the adjunct segment 4690. FIGS. 92A-92D show an adjunct segment 4700 which includes a thicker portion 4704 in the center of the adjunct segment, between the openings 4702 for staple legs.

FIG. 93 shows an embodiment of a delivery configuration assembly 4710 for adjunct segments 4712. The adjunct segments 4712 can be made as individual components, not connected by branches or filaments, adhered to a compliant or removable backing 4714. The arrangement of the adjunct segments 4712 on the backing 4714 can be such that mating the delivery configuration assembly 4710 with a surgical stapler anvil or staple cartridge allows for perfect or near perfect alignment of the adjunct segments 4712 with the stapler features.

FIGS. 94A-94D show an embodiment for an adjunct segment 4715 that has a base portion 4717 and thicker portions 4716 with openings 4718. The openings 4718 go through the thicker portions 4716 as well as the base portion 4717. The thicker portions 4716 may be a different material than the base portion 4717 or the thicker and base portions may be of the same or similar materials. The thicker portions 4716 may prevent tissue damage from staple legs when the tissue expands or contracts. FIGS. 95A-95D show an adjunct segment 4720 that has a base portion 4722 with openings 4726 for staple legs and portions around the openings 4724. The openings portions around the openings 4724 may be of a different material than the base portion 4722, or they base 4722 and the portions surrounding the openings 4726 may be of the same material, but, because of their configuration, have different materials properties, such as they may act as cushions between the adjunct segment 4720 and a surgical staple or tissue.

Application of Adjunct Materials

Sealant materials can be applied to tissue that is treated with surgical staples directly, prior to or after being treated with a surgical stapler and endocutter as a film or a liquid as an alternative to being applied as an adjunct segment.

FIGS. 96-99C show an applicator for applying liquid or gel adjunct material 4899 directly to an anvil or a staple cartridge of a surgical stapler 4891. FIG. 96 shows an embodiment 4890 in which an adjunct material 4899 is applied from a tube 4896, through an applicator 4897 attached to the tube 4896. The adjunct material 4899 is shown on the anvil 4892. FIG. 97 shows a cross-sectional view of an applicator 4897 with gel adjunct material 4894 in contact with the anvil 4892 to fill staple forming openings 4893. FIG. 98 shows a view of an applicator 4897 with a squeegee feature 4898 to apply adjunct material 4894 to an anvil 4892 to fill staple forming openings 4893 with adjunct material. FIG. 99A shows an applicator 4909 for applying adjunct material 4906 from a reservoir 4908 to an anvil 4904 of a surgical stapler 4900. FIG. 99B shows an alternate type of applicator 4920 for applying adjunct material 4922 to an anvil 4914 of a surgical stapler 4910. The applied adjunct material 4922 is smoothed by the applicator 4920 into the staple forming openings 4916 to form adjuncts 4918. FIG. 99C shows the adjuncts 4918 in the staple forming openings 4916 in the anvil 4914.

FIGS. 100-104 show an applicator for applying an adjunct material directly to an anvil of a surgical stapler, in which the material is composed of two precursors or two materials which mix prior to application to the anvil or staple cartridge. FIG. 100 shows an embodiment 4930 of an applicator 4942 for an adjunct material from two materials 4936, 4940. The applicator 4942 includes a dual syringe set 4932 and a mixing nozzle 4944. The dual syringe set 4932 includes individual syringes 4934, 4938 that interface with the applicator nozzle 4946 through fittings, such as Luer fittings or threaded fittings. The individual syringes are shown as syringe A 4934, that can contain a first material 4936, such as fibrin; and syringe B 4938, that can contain a second material 4940, such as thrombin. A single plunger expels the first and second materials into the mixing nozzle 4994 before the adjunct material exits through the applicator nozzle 4946. FIG. 101 is a similar embodiment, but the diameters of the syringes 4952, 4954 in the syringe set 4950 are different, so that upon application of the plunger, a ratio of materials other than 1:1 exits the syringes and mixes in a common lumen, the mixing nozzle 4958, before exiting through the applicator nozzle 4959.

FIGS. 102A and 102B show the interface between a syringe or other container 4960 filled with an adjunct material 4962 and a portion of a mixing or applicator nozzle 4963. The interface includes a fitting between a threaded portion 4966 of the container 4960 of adjunct material 4962 and a threaded portion 4965 of the nozzle 4963. The container 4960 of adjunct material 4962 can include a seal 4961 that keeps the adjunct material 4962 within the container 4960 during shipping and storage. The nozzle 4963 includes a piercing feature 4964 to break the seal 4961 when the threaded portions 4965 and 4966 are fully engaged. When the threaded portions 4965 and 4966 are fully engaged the adjunct material 4962 flows from the container 4960 into the nozzle 4963. FIGS. 103 and 104 show a dual syringe set 4932 attached to a mixing nozzle 4944 and applicator nozzle 4946, as in FIG. 100, in use applying adjunct material 4969 to an anvil 4968 of a surgical stapler 4967.

FIGS. 105-110 show fittings and which can apply liquid or gel to a portion of a surgical stapler, either to the anvil or the staple cartridge and the resulting adjunct layer. In FIG. 105 and FIG. 106, the applicator nozzle 4977 is shown fitted over an anvil 4976. In FIG. 105, the adjunct material 4978 is a single adjunct material, that is to say that it is not a material that needed to be mixed immediately prior to application. The adjunct material 4979 shown in FIG. 106 includes two precursors or components that are mixed immediately prior to application of the adjunct material to the anvil. FIG. 107 shows an anvil 4980 with staple forming openings 4981 filled with adjunct material 4982 that was applied with a nozzle applicator, such as shown in FIG. 105 and FIG. 106.

Adjunct material can be applied to staple cartridges used with surgical staplers. FIG. 108 shows an applicator nozzle 4984 coupled to a staple cartridge 4983 to apply adjunct 4985 to staples 4986 loaded in the cartridge. FIG. 109 also shows an applicator nozzle 4988 fitted to a staple cartridge 4983. In FIG. 109, the adjunct material 4987 flowing over the staple 4986 is made of two constituents or components which are mixed immediately prior to application of the adjunct material to the cartridge. FIG. 110 provides a view of applied adjunct material 4989 on staples 4986 loaded in a stapler cartridge 4983.

FIG. 111 shows a surgical staple 4992 improperly situated inside of tissue 4991. Such a configuration 4990 can occur when no adjunct material is present to distribute forces from the staple on the tissue and prevent the staple from cutting through tissue or inappropriately compressing the tissue. FIG. 113 shows how the presence of adjunct material 4998 on the anvil-side of a staple 4997 can allow proper placement of the staple 4997 in tissue 4996.

FIG. 112 shows a stick of gel adjunct material 4994 that is applied to the anvil 4995 or staple cartridge of a surgical stapler 4993. This is an alternate embodiment for a method for applying, and an applicator of, adjunct material. In this way, a surgical stapler can be reloaded and prepared quickly, such as when a surgeon needs to use a single surgical stapler multiple times in a single procedure.

FIGS. 114A-114C show surgical staples 41010 used with adjuncts 41012 used with a surgical stapler 41000 to transect tissue 41002. In the surgical stapler 41000, the anvil 41004 can be loaded with adjunct segments 41012 which interact with the staples 41010 loaded in the staple cartridge 41006. The adjuncts 41012 in the anvil 41004 can hold staples 41010 that are not applied to tissue 41002, as shown in FIG. 114C.

Adjuncts for Anastomosis

Anastomosis is a process which requires creating a circular cut through a staple line in each end of the tissues to be connected. Cutting through a staple line can cause torn or partially cut staples. Dog ears of tissue at the corners of the staple line can have leaks or allow debris to collect, however, if it is not possible to eliminate dog ears altogether, then it sealing them to minimize leakage is desirable. Described below are adjunct assemblies for use with specific staple cartridge configurations that include seals for dog ears, as well as provide a minimal amount of staples through the area that is eventually cut by a circular cutting implement.

FIG. 115 shows an embodiment of a non-continuous adjunct 41020 for use in forming an anastomosis. The non-continuous adjunct 41020 includes a ring 41022, or washer, in the center of the adjunct. Attached on either side, 180.degree. apart, are suture filaments 41026. The suture filaments connect to sealing material 41024. Each portion of sealing material 41024 is configured to seal a dog ear portion of the staple line. The sealing material 41024 is configured to span multiple staples and once inserted into tissue, the staple can have the sealing material 41024 adjacent to the crown of the staple or adjacent to the anvil-side of the staple. In some embodiments, the sealing material 41024 is configured to be adjacent to the crown of staples deployed in tissue. Such sealing material can be complemented with sealing material, such as adjunct segments, on the anvil-side of the staple.

FIGS. 116 and 117 show a surgical staple cartridge 41028 and a staple pattern for use with the adjunct of FIG. 115. The staple pattern on the cartridge 41028 is shown to have areas of two or more rows of staples 41030 and areas with a single row of staples 41031. The single row of staples 41031 is intended to, or configured to, correspond to the portion of the tissue that will be cut through in forming a circular cut. The suture filament 41026 of the non-continuous adjunct 41020 is delivered parallel to this single row of staples 41030. The areas of two or more rows of staples 41030 correspond to where the dog ears in the tissue will be. The sealing material 41024 of the non-continuous adjunct 41020 is configured to be used with the two or more rows of staples 41030, as shown in FIG. 116.

In the staple cartridge 41028 shown in FIG. 116 and the staple pattern shown in FIG. 117, it can be seen that the single row of staples 41031 is centered with respect to the multiple rows of staples 41030 in the dog ear area. The suture filament 41026 of the non-continuous adjunct 41020 will not only be substantially parallel to the single row of staples 41031, but the suture filament 41026 will almost overlay the single row of staples 41031 once the adjunct 41020 is deployed with surgical staples into tissue. More than one non-continuous adjunct 41020 can be deployed at a time, and is shown in FIG. 116, in such situations, the non-continuous adjuncts 41020 can be substantially similar.

FIG. 118 is an illustration of an alternative embodiment of a non-continuous adjunct for use in forming an anastomosis. Shown are two non-continuous adjuncts 41040, 41050 that are mirror images of each other. The non-continuous adjuncts 41040, 41050 each have a washer 41046, 41056, attached to suture filaments 41044, 41054. The suture filaments 41044, 41054 are attached to sealing material 41042, 41052 that is configured to span multiple surgical staples in the dog ear area of the stapled tissue.

FIGS. 119-123 show a surgical stapler cartridge 41060 for use with the adjuncts of FIG. 118, as well as further views of the non-continuous adjuncts 41040, 41050 of FIG. 118. The stapler cartridge 41060 is symmetric about a centerline, where a cut through stapled tissue can be made. The cartridge 41060 has areas for a single row of staples 41064 and for multiple rows of staples 41062 on each half of the cartridge. The multiple rows of staples 41062 are at the ends of the staple line and are where the dog ear portion of the tissue will be. The single rows of staples 41064 are off-center with respect to the multiple rows of staples 41062, such that the single rows of staples 41064 are located towards the edges of the cartridge 41060. When the non-continuous adjuncts 41040, 41050 are overlaid onto the cartridge, the sealing material 41042, 41052 corresponds to the areas on the cartridge 41060 with multiple rows of staples 41062, the washers 41046, 41056 are each in the center of a single row of staples 41064, each on one half of the cartridge 41060. The suture filaments 41046, 41056 are substantially parallel to the single rows of staples 41064, but do not overlay them. FIG. 121 shows the relative positioning of the non-continuous adjuncts 41040, 41050 and staples, showing the unsealed staples 41066 of the single rows of staples. These unsealed staples 41066 can be cut through or removed when an anastomosis is formed. FIG. 122 shows the view of FIG. 121 overlaid on the view of FIG. 120. FIG. 123 includes depressions in the staple cartridge 41060 underneath the washers 41046, 41056.

FIG. 124 shows an embodiment of an adjunct washer 41066 before and during actuation of a surgical stapler. The washer 41066 can be one similar to any of the previously discussed washers, 41022, 41046, 41056. The washer 41066 is shown in a recess in a stapler cartridge 41064. Suture filaments 41068 connect to the washer 41066. When the adjunct is placed in the surgical stapler, before staple deployment, the washer 41066 is substantially circular in cross-section. During staple deployment, the washer 41066 compresses under pressure 41070 from the surgical stapler. The washer 41066 then has a substantially elliptical cross-section. Under pressure, the washer 41066 becomes flush, or nearly flush, with an upper portion of the staple cartridge while filling, or nearly filling, the recess.

FIG. 125 shows an embodiment of a surgical staple cartridge for use in forming an anastomosis. This side view allows a comparison for the tips of a standard staple cartridge 41072 and that of a LAR 41074. A person skilled in the art will appreciate that it could be useful in LAR procedures to reduce the length of the end effector distal to an articulation joint in the stapler. It is believed that reducing the distance from a distal most staple in the cartridge to the distal most location on the staple cartridge will enable this effort as shown in FIG. 125. A person skilled in the art will be able to ascertain the appropriate relative distances.

FIG. 126 shows a body lumen transected by a surgical stapler with an adjunct, such as the one shown in 118. The tissue 41076 is shown with non-continuous adjuncts 41040, 41050 in place. The washers 41046, 41056 align, and alongside each washer 41046, 41056 and the suture filaments 41044, 41054 connected to each washer is a single row of staples 41066 that is not sealed by adjunct material. Sealing material 41042, 41052 prevents leaks in the dog ear portions of tissue with multiple rows of staples.

FIGS. 127A-127C shows a cross-sectional view of the use of an adjunct 41050, such as the one shown in FIG. 118 and a circular stapler trocar 41078. FIG. 127A shows the non-continuous adjunct in tissue 41076 with the washer 41056 above a staple line that includes the unsealed, single row of staples 41066. FIG. 127B shows the trocar 41076 approaching the staple line 41066 and washer 41056 as it moves through a lumen in the tissue 41076. FIG. 127C shows the engagement of the trocar 41078 with the washer 41056. FIG. 128 shows the relative positioning of all of the components of the adjunct 41505 when the trocar 41078 is engaged with the washer 41056.

FIGS. 128-136 shows a circular stapler trocar 41078 passing through a washer portion of a non-continuous adjunct 41050. FIG. 129 shows the non-continuous adjunct 41050 with a washer 41056, suture filaments 41054, and sealing material 41052 at the dog ears of the tissue 41076. A circular staple and cutting implement 41080 is inside the tissue 41076. A trocar 41078 is at the center of the staple and cutting implement 41080. The trocar 41078 extends through the washer 41056 toward a shaft 41084 that is connected to an anvil 41082 in another portion of the tissue 41076 that has been cut and sealed along a staple line 41088. The anvil 41082 is shown above a buttonhole that is adjacent the shaft 41084.

FIG. 130 shows an embodiment similar to that shown in FIG. 129. In FIG. 130 the non-continuous adjuncts 41040, 41050 are shown each with a washer 41046,41056, suture filaments 41044, 41054, and sealing material 41042,41052 at the dog ears of the tissue 41076. A single row of staples 41066 surrounds each of the washers 41046, 41056 near the suture filaments. A circular staple and cutting implement is inside the tissue 41076, and the trocar 41078 extends through one washer 41056 towards a mating shaft that extends through the other washer 41046.

FIGS. 131-133 show cross-sectional views of the movement of the sections of tissue 41076 toward each other, so that the tissue can be stapled (FIG. 135) and cut FIG. 136 to create an anastomosis. FIG. 131 is a cross-sectional view of FIG. 129, but with the shaft 41084 attached to the anvil 41082 fitted over the trocar 41078 and in contact with the washer 41056. FIG. 132 is a closer view of the shaft 41084 connected to the anvil and the center portion of the adjunct 41050, particularly the washer 41056 and suture filaments 41054. As the shaft 41084 moves down, so that the two portions of the tissue 41076 move together, the shaft 41084 moves the suture filaments 41054 downward so that the sealing material 41052 on the dog ears move closer together, as shown in FIG. 133. FIG. 134 shows the movement of the sealing material 41052 on the dog ears toward the trocar 41078 as the shaft moves the washer 41056 downward. FIG. 135 shows the tissue sections attached with staples 41100. The adjunct 41050, with the washer 41056 pushed down by the shaft and the sealing material 41052 at the dog ear portion, are shown in the center of the stapling and cutting implement 41080. FIG. 136 shows the tissue 41076 after the circular cut has been made. The tissue is joined with three rows of staples 41100 in a circular configuration with the previously stapled tissue, including the non-continuous adjunct 41050, removed. The adjuncts 41020, 41040, 41050 described above can be used interchangeably or in combination in the methods for creating an anastomosis shown in FIG. 126-136.

Reprocessing

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument, which can include an adjunct material, is obtained and if necessary cleaned. The instrument can then be sterilized. In some embodiments, the instrument can be dried, e.g., in an oven, together with a desiccant item, which can have a greater affinity for moisture than the adjunct material. In one sterilization technique, the instrument is placed in a closed and sealed container, such as a plastic or TYVEK bag or a foil bag. The container and instrument are then placed in a field of radiation that can penetrate the container, such as gamma radiation, x-rays, or high-energy electrons. The radiation kills bacteria on the instrument and in the container. In another sterilization technique, the instrument is placed in a first container, such as a plastic or TYVEK bag, having a vapor permeable backing. The first container can then be packaged in a second container, e.g., a foil bag, which can be left open. The first and second containers, together with the instrument, can undergo ethylene oxide sterilization. The second container can then be sealed to prevent moisture exposure. Prior to sealing, a desiccant item may be included in at least one of the first and second containers to further prevent changes to one or more device components. In both techniques, the sterilized materials can then be stored in the sterile container(s) to keep the materials sterile until the container(s) is/are opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A staple cartridge assembly for use with a surgical stapler, comprising:
    a cartridge body configured to be disposed within a jaw of a surgical stapler, the cartridge body having a plurality of staple cavities, each staple cavity having a surgical staple disposed therein, each of the surgical staples having a pair of legs, each of the legs of the surgical staple having an adjunct that is disposed therearound prior to the cartridge body being disposed within the jaw and that is movable independent of the adjunct disposed around the other leg of the surgical staple, and each adjunct forming a fluid tight seal around the leg of the surgical staple around which the adjunct is disposed upon deployment of the surgical staple from the cartridge body.

2. The assembly of claim 1, wherein each of the plurality of adjuncts is in the form of a plug.

3. The assembly of claim 2, wherein, for each surgical staple, a first adjunct plug is disposed around a first leg of the surgical staple and a second adjunct plug is disposed around a second leg of the surgical staple such that the first and second adjunct plugs form a seal around the first and second legs of the surgical staple.

4. The assembly of claim 1, wherein each of the plurality of adjuncts is formed from a swellable material that expands upon contact with body fluids.

5. The assembly of claim 4, wherein the swellable material is a hydrogel.

6. The assembly of claim 1, wherein each of the plurality of adjuncts is formed from a foam.

7. The assembly of claim 1, wherein each of the plurality of adjuncts is positioned adjacent to a crown of the surgical staple prior to deployment from the cartridge body.

8. The assembly of claim 1, wherein each of the plurality of adjuncts is positioned at a distal end of the leg of the surgical staple around which the adjunct is disposed prior to deployment from the cartridge body, the distal end being opposite a crown of the surgical staple.

9. The assembly of claim 1, wherein each of the plurality of adjuncts is configured to slide over the leg around which the adjunct is disposed.

10. A staple cartridge assembly for use with a surgical stapler, comprising:
    a cartridge body having a plurality of staple cavities;
    a plurality of surgical staples disposed within the plurality of staple cavities and configured to be ejected therefrom into tissue; and
    a plurality of sealing adjuncts disposed within the plurality of staple cavities and each associated with one of the surgical staples, each of the sealing adjuncts being configured to slide along its associated one of the surgical staples during ejection of the associated one of the surgical staples from the cartridge body and then be ejected from the cartridge body, the sealing adjuncts each being formed from at least one flowable or swellable material.

11. The assembly of claim 10, wherein each of the plurality of sealing adjuncts is configured to expand in volume upon contact with tissue.

12. The assembly of claim 10, wherein each of the plurality of staple cavities is shaped to accommodate passage of the sealing adjunct disposed therein.

13. The assembly of claim 12, wherein each of the plurality of staple cavities includes at least one cut-out formed on opposing ends of the staple cavity to accommodate the sealing adjunct disposed therein.

14. The assembly of claim 10, wherein each of the plurality of sealing adjuncts is fully contained within the plurality of staple cavities prior to the ejection of its associated one of the surgical staples from the cartridge body.

15. A method for stapling tissue, comprising:
 engaging tissue between a cartridge assembly and an anvil of a surgical stapler, the cartridge assembly having disposed therein at least one staple having a sealing adjunct disposed around at least one leg of the at least one staple; and
 after the engagement of the tissue, actuating the surgical stapler to eject at least one staple from the cartridge assembly into the tissue and thereby form a puncture in the tissue, wherein the at least one leg of the at least one staple moves through the sealing adjunct during the ejection such that the sealing adjunct expands and forms a fluid tight seal of the puncture between the tissue and the at least one leg.

16. The method of claim 15, wherein the sealing adjunct is coupled to a distal end of the at least one leg of the at least one staple and actuating the surgical stapler causes the adjunct to slide toward a crown of the at least one staple and seal a hole formed in the tissue by the at least one leg.

* * * * *